United States Patent [19]

Hiyama et al.

[11] Patent Number: 5,436,655
[45] Date of Patent: Jul. 25, 1995

[54] ENDOSCOPE APPARATUS FOR THREE DIMENSIONAL MEASUREMENT FOR SCANNING SPOT LIGHT TO EXECUTE THREE DIMENSIONAL MEASUREMENT

[75] Inventors: Keiichi Hiyama, Akishima; Masahide Kanno, Hachioji; Shinichiro Hattori, Akishima, all of Japan

[73] Assignee: Olympus Optical Co., Ltd., Tokyo, Japan

[21] Appl. No.: 279,082

[22] Filed: Jul. 22, 1994

Related U.S. Application Data

[63] Continuation of Ser. No. 924,634, Aug. 4, 1992, abandoned.

[30] Foreign Application Priority Data

Aug. 9, 1991 [JP] Japan .................. 3-200873
Aug. 15, 1991 [JP] Japan .................. 3-205165
Aug. 16, 1991 [JP] Japan .................. 3-205936
Aug. 21, 1991 [JP] Japan .................. 3-209575
Aug. 21, 1991 [JP] Japan .................. 3-209576
Aug. 23, 1991 [JP] Japan .................. 3-212176
Aug. 23, 1991 [JP] Japan .................. 3-212177
Dec. 2, 1991 [JP] Japan .................. 3-317970

[51] Int. Cl.6 .................. A61B 1/04; A61B 1/06
[52] U.S. Cl. .................. 348/45; 348/68; 348/139; 348/195; 348/197
[58] Field of Search ............ 348/45, 65, 68, 139, 348/195, 197; H04N 7/18

[56] References Cited

U.S. PATENT DOCUMENTS

| | | | |
|---|---|---|---|
| 3,799,150 | 3/1974 | Bonnet | 128/6 |
| 4,300,167 | 11/1981 | Miller | 348/356 |
| 5,090,400 | 2/1992 | Saito | 348/67 |
| 5,103,497 | 4/1992 | Hicks | 385/117 |
| 5,243,399 | 9/1993 | Koop | 356/153 |

*Primary Examiner*—Howard W. Britton
*Attorney, Agent, or Firm*—Armstrong, Westerman, Hattori, McLeland & Naughton

[57] ABSTRACT

Arranged within a measuring-light generating unit of an endoscope apparatus for three dimensional measurement, according to the invention, are measuring means, a lamp for outgoing a normal illuminating light, and a laser for outgoing a measuring light. Connected to the measuring means is a signal line which is connected to a CCD. Further, an illuminating light outgone from the lamp is condensed by a condenser lens, and is incident upon an incident end surface of a light guide. Furthermore, the measuring light outgone from the laser is condensed by the condensing lens, and is incident upon the incident end surface of the image guide. Moreover, the incident end of the image guide is connected to scanning means formed by a piezo-electric element, a speaker (voice coil) or the like through a connecting element. The scanning means is operated whereby the incident end of the image guide is reciprocally moved in a direction perpendicular to an optical axis of the measuring light. The measuring light is a light having extension or spreading. However, a flux of light of the measuring light is extremely thin, and a spot light having minimum resolution that is a single glass fiber forming the image guide is projected onto the subject.

45 Claims, 63 Drawing Sheets

FIG.2
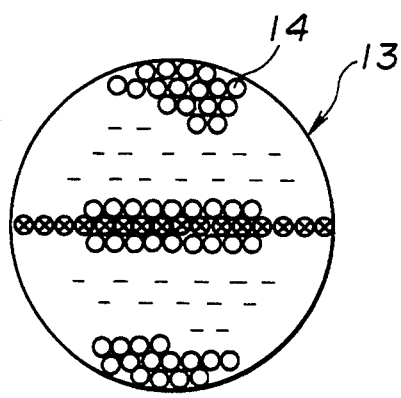
FIG.3(a)     FIG.3(b)
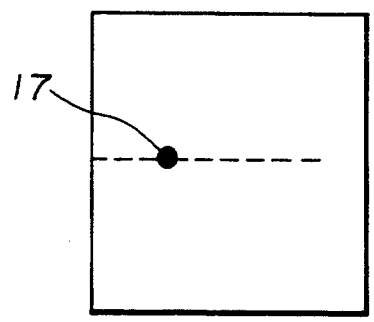
L-IMAGE
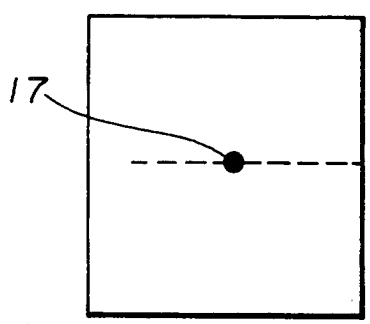
R-IMAGE

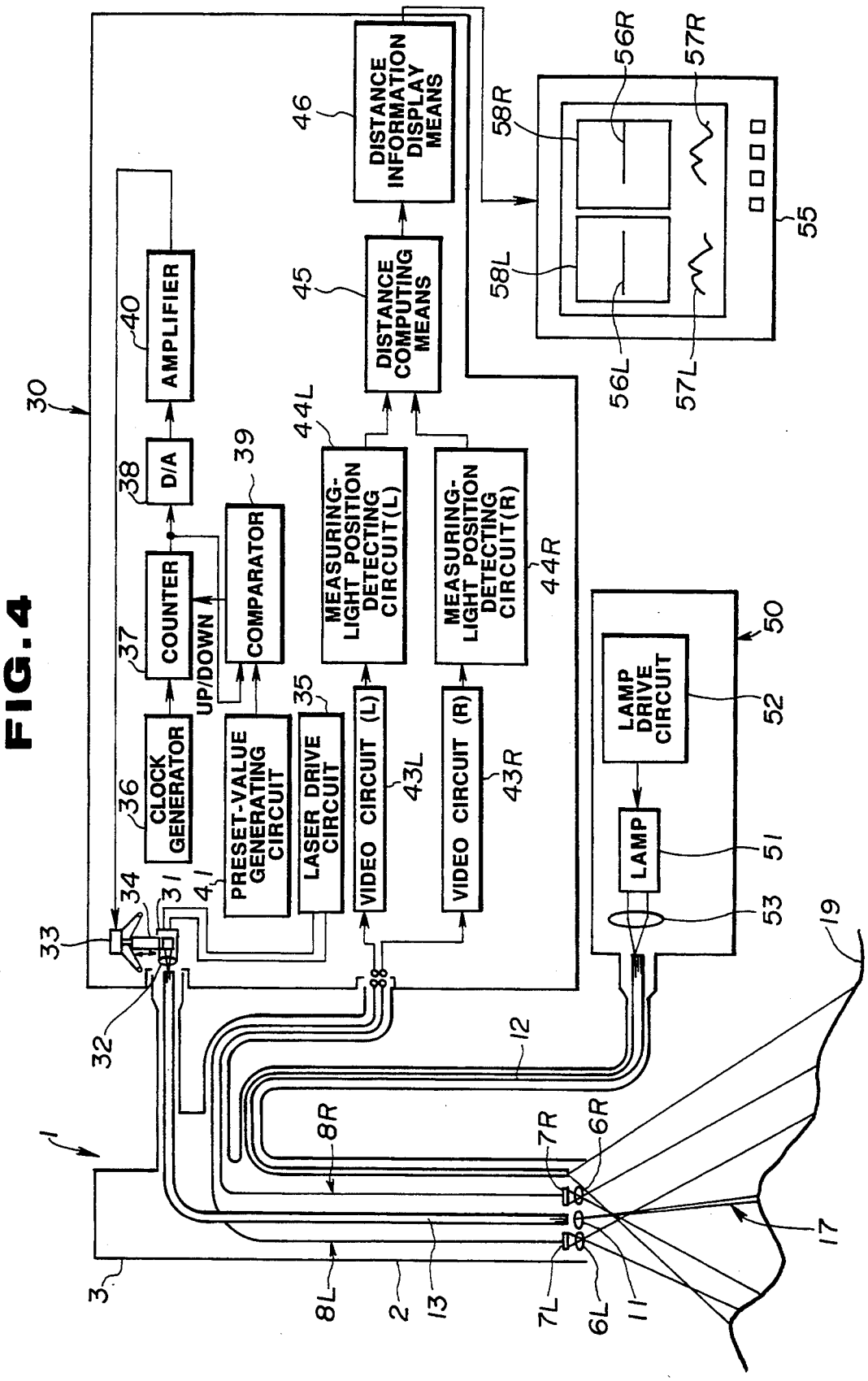

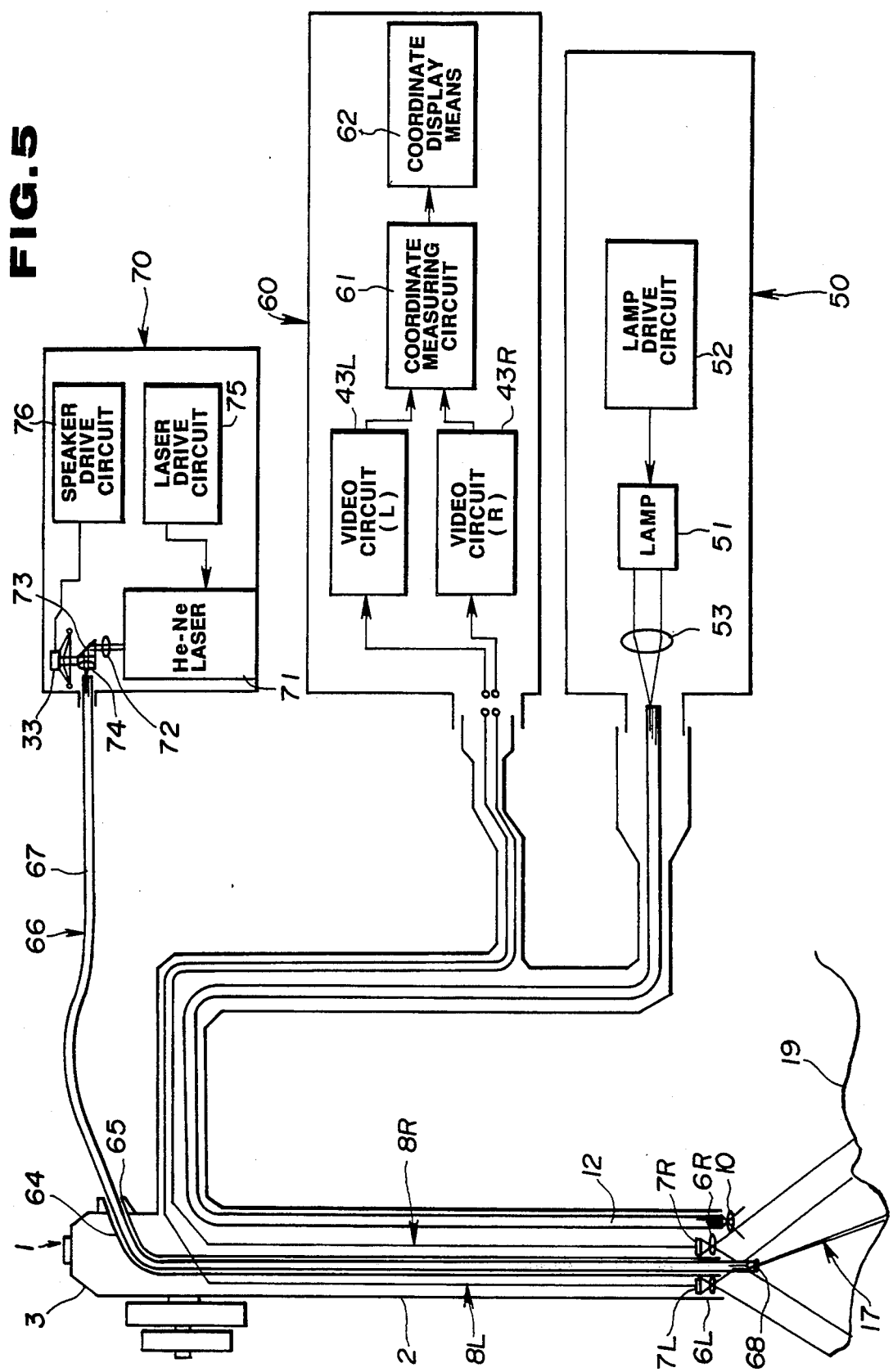

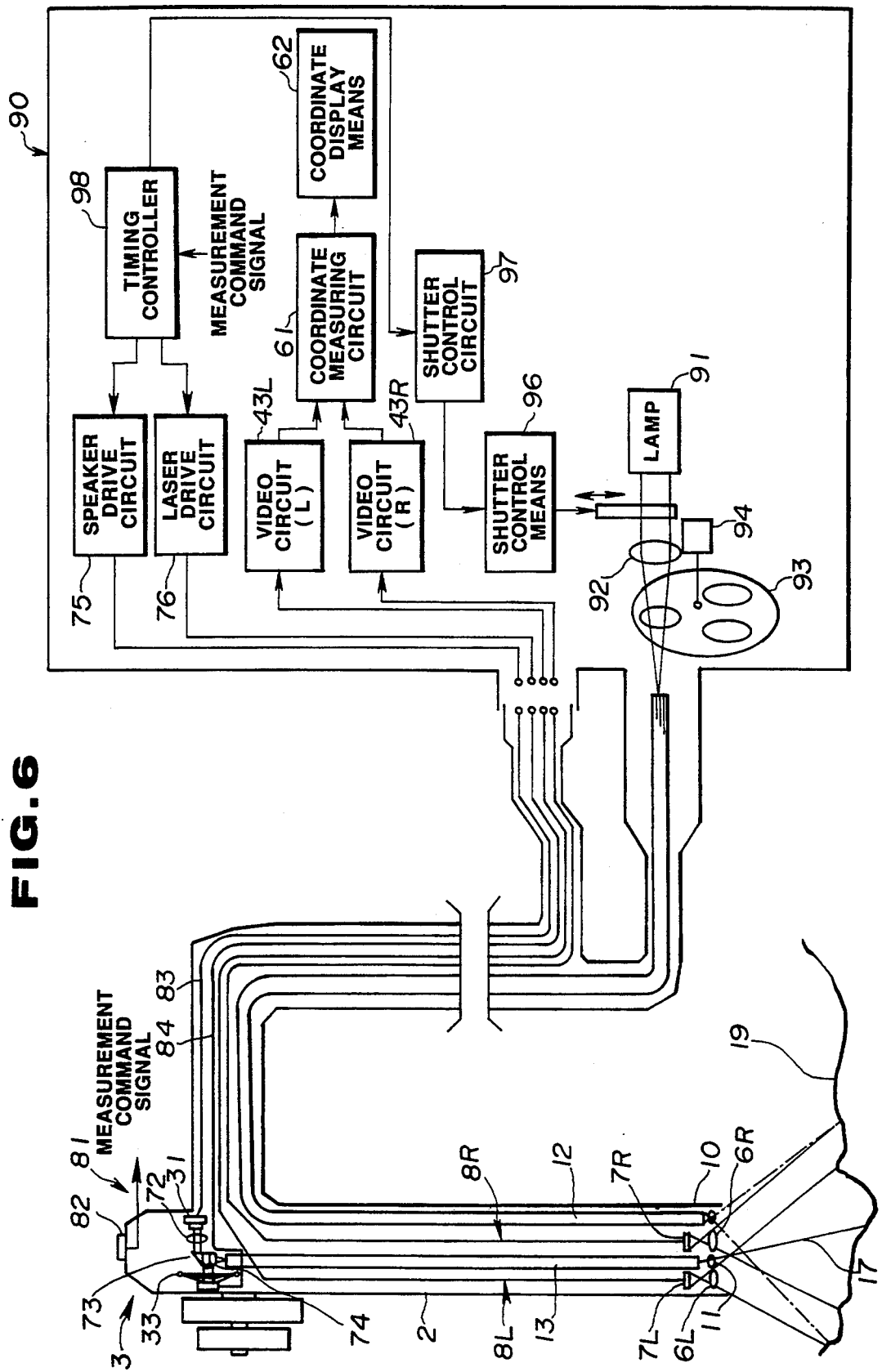

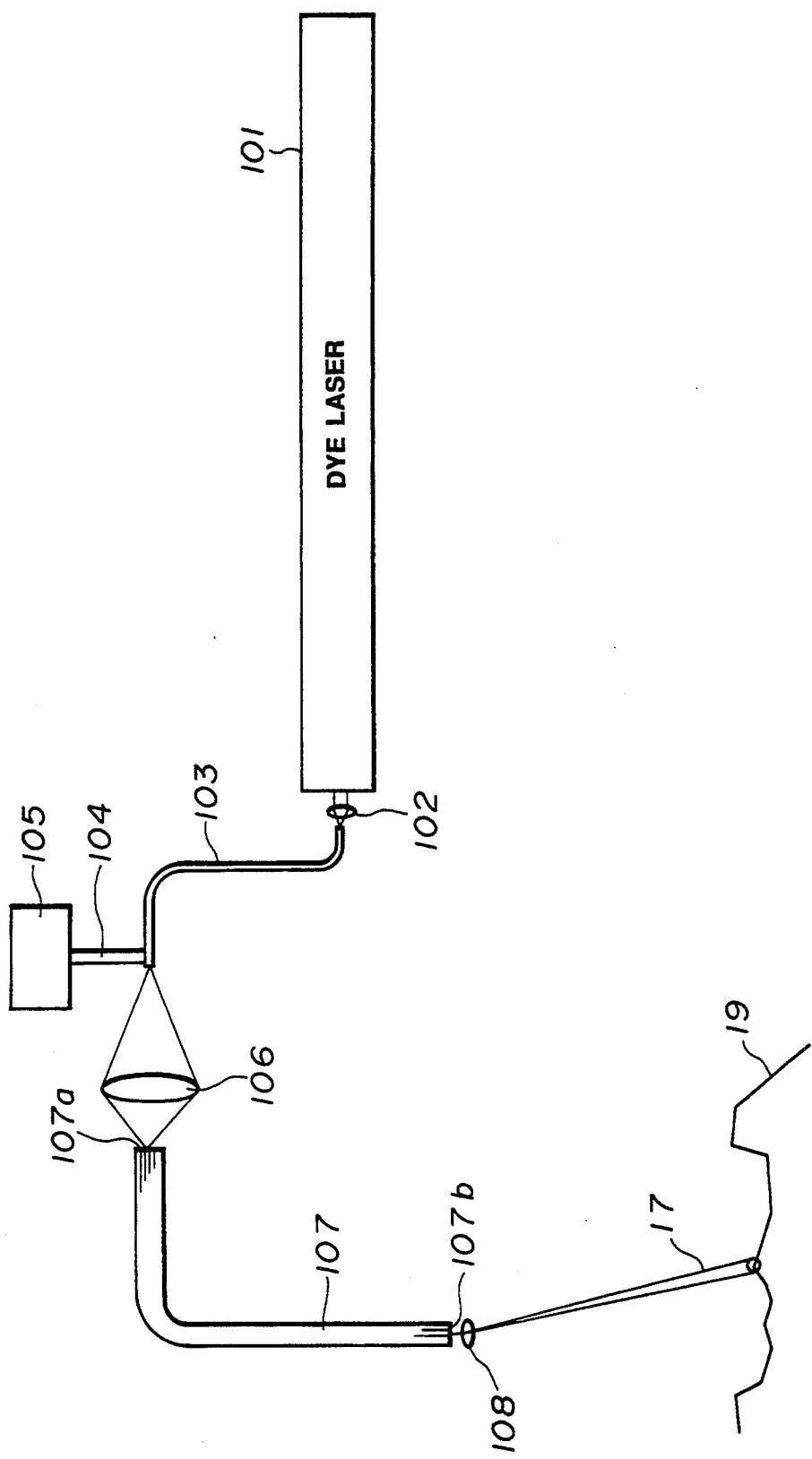

TO FORWARD END OF ENDOSCOPE

FIG. 14
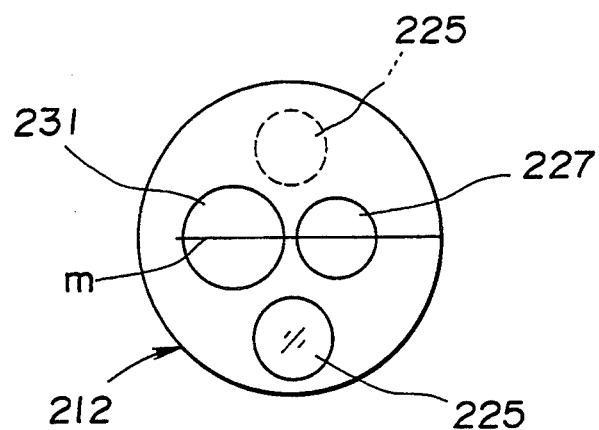
FIG.15(a) FIG.15(b)
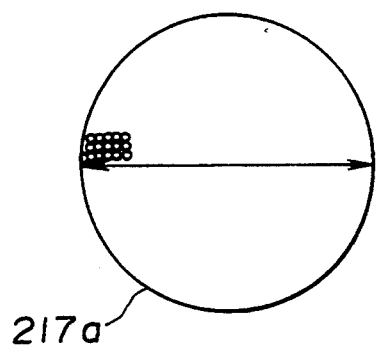 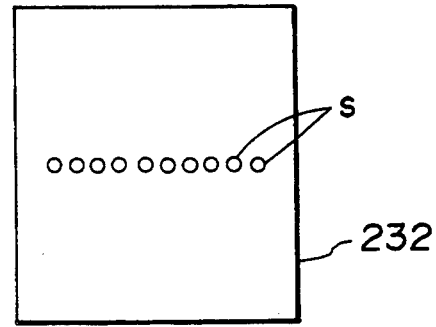
FIG.17
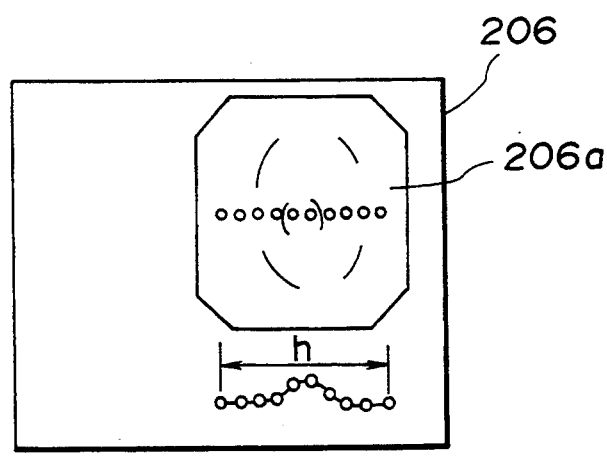

FIG. 20
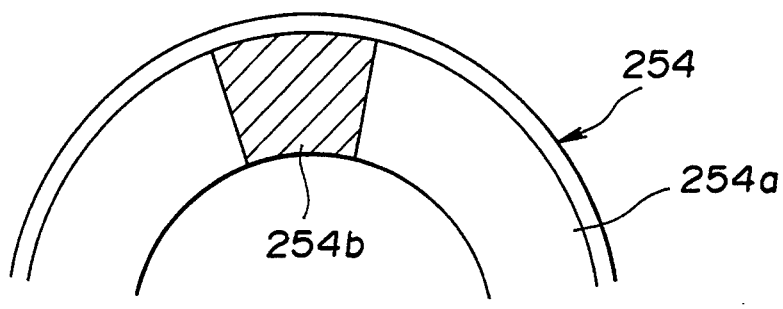
FIG. 22(a)  FIG. 22(b)
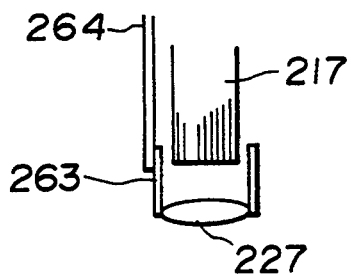 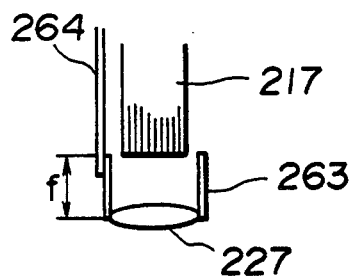
FIG. 24(a)  FIG. 24(b)
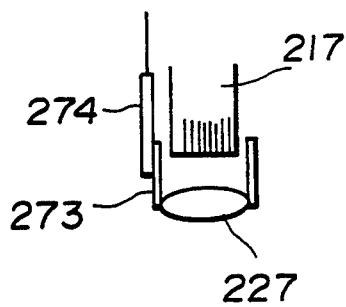 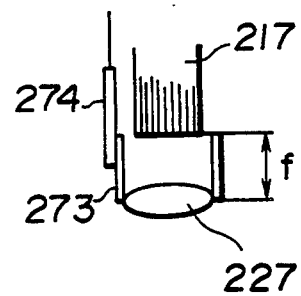

FIG. 49
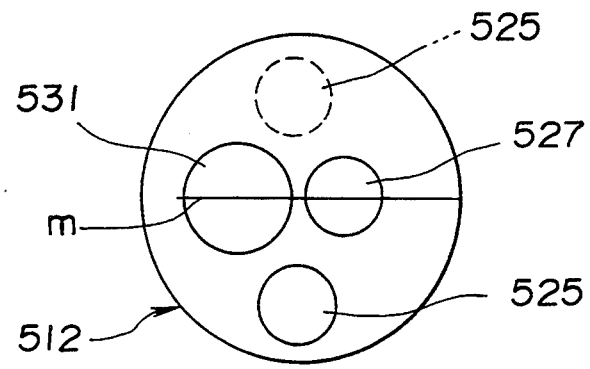
FIG. 50(a) FIG. 50(b)
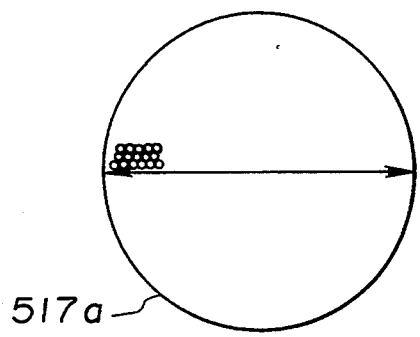 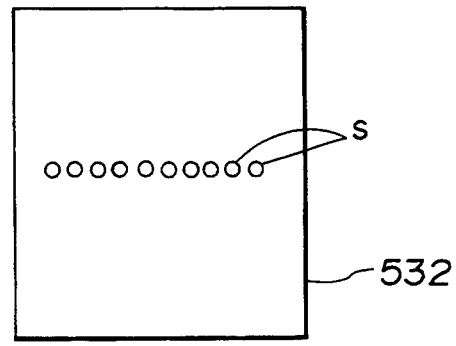
FIG. 51
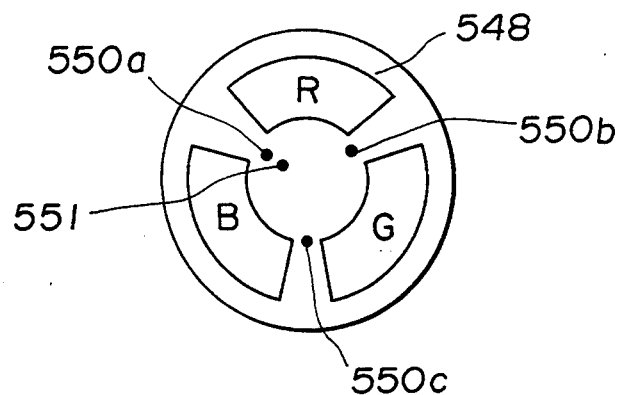

FIG.53
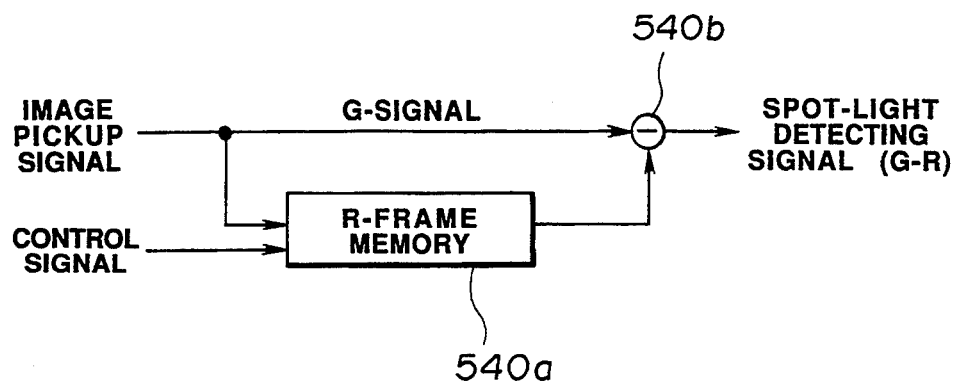
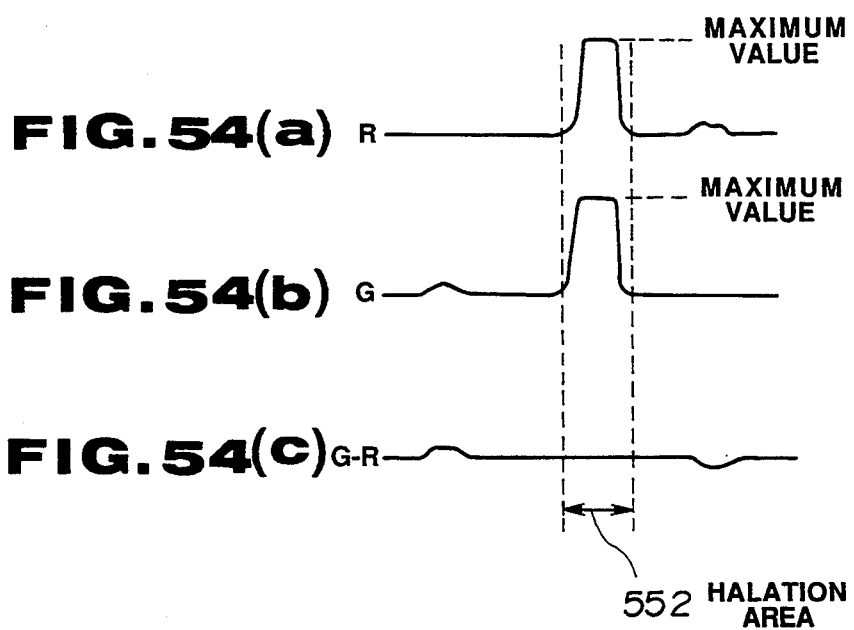

FIG. 55(a) R
FIG. 55(b) G
MAXIMUM VALUE
FIG. 55(c) G-R
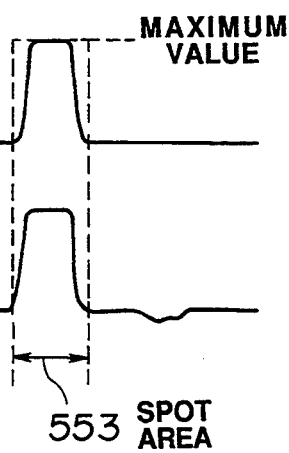
553 SPOT AREA
FIG. 56
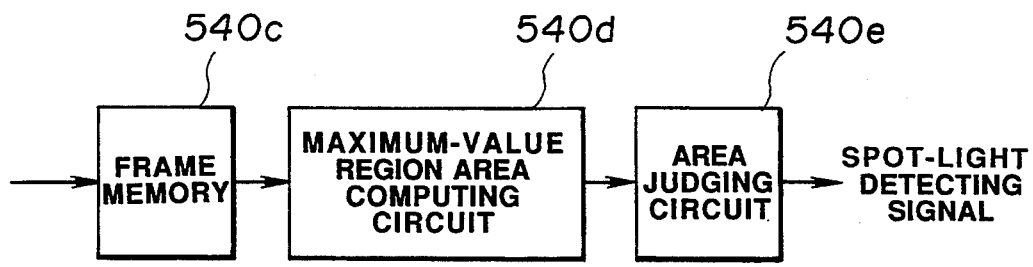

FIG. 59
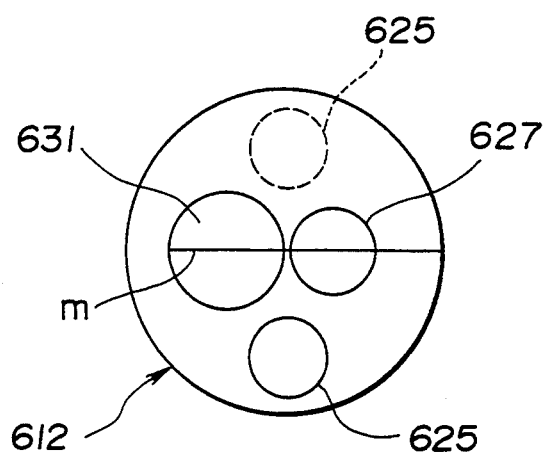
FIG. 60(a)   FIG. 60(b)
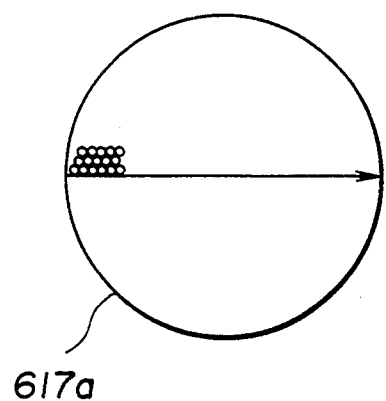
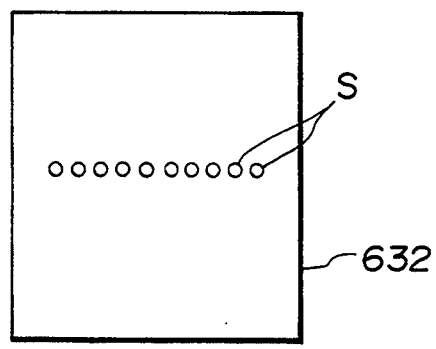

FIG.69(a)     FIG.69(b)
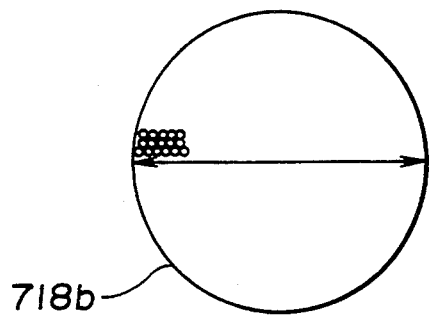
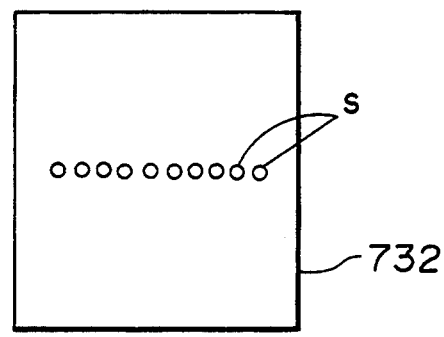
FIG.70
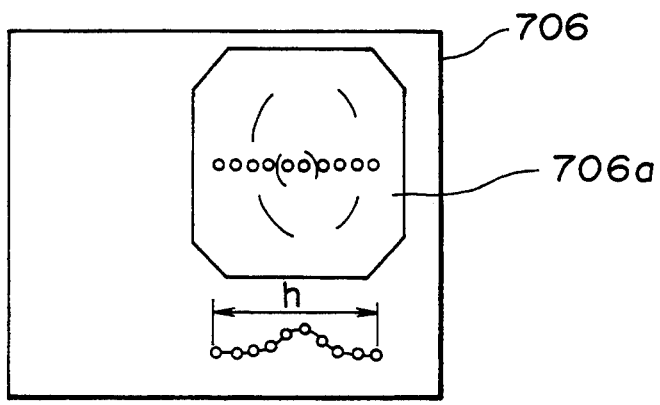
FIG.71(a)     FIG.71(b)
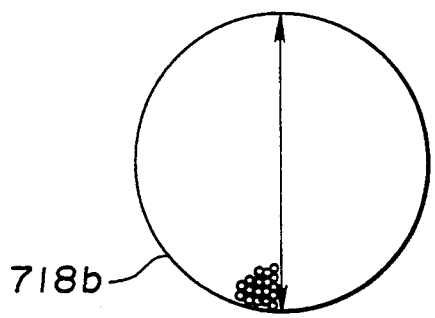
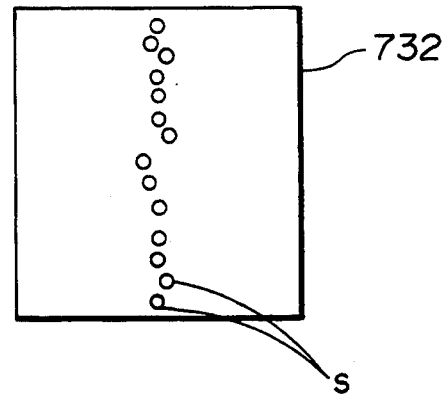

FIG.77
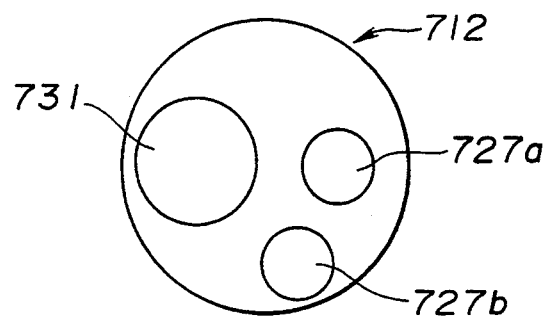
FIG.78
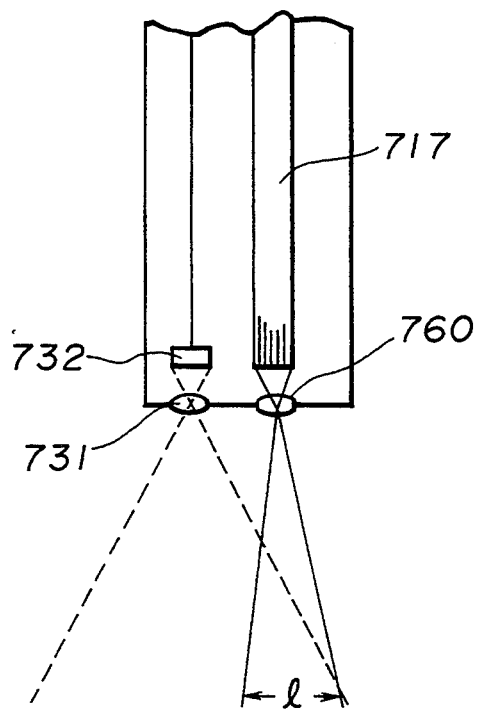
FIG.79(a)    FIG.79(b)
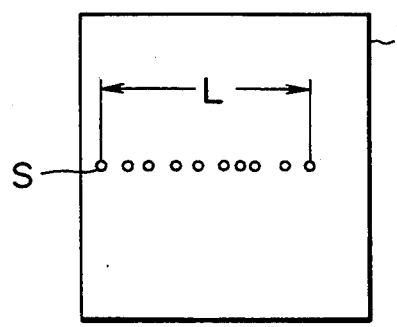 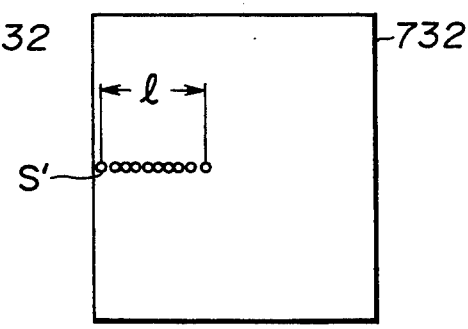

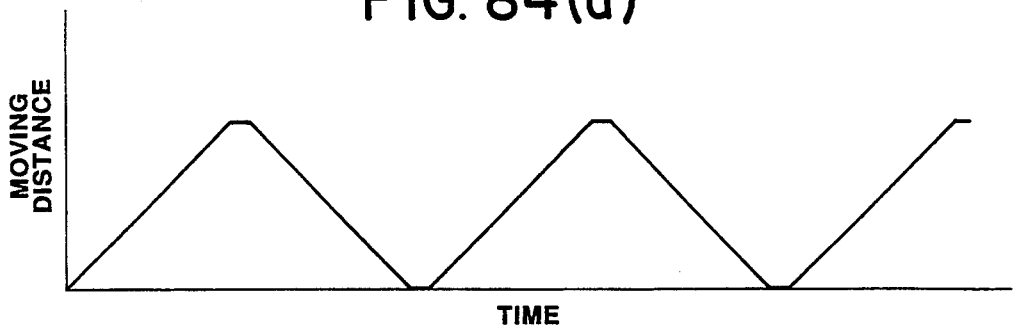
FIG. 84(a)
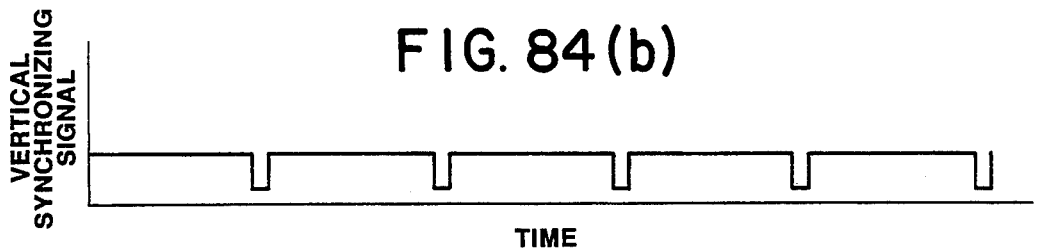
FIG. 84(b)
FIG. 85
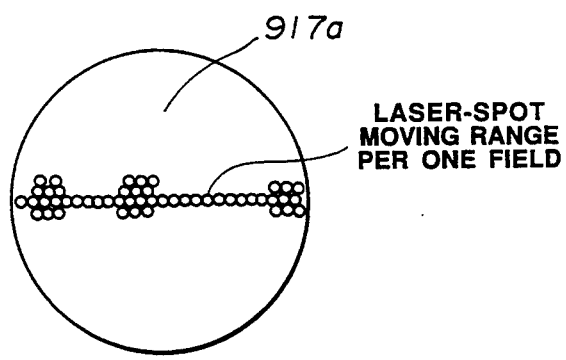

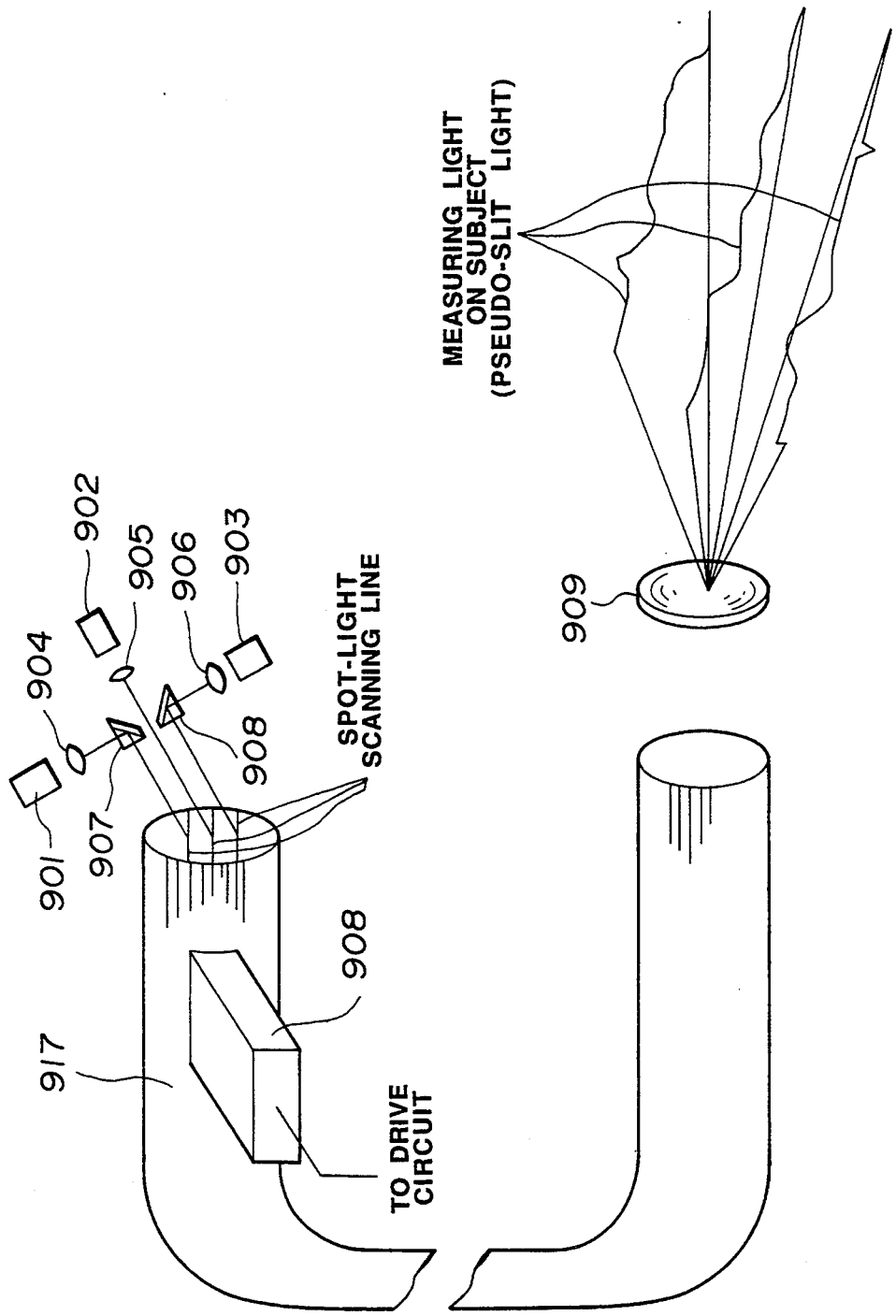

ENDOSCOPE APPARATUS FOR THREE DIMENSIONAL MEASUREMENT FOR SCANNING SPOT LIGHT TO EXECUTE THREE DIMENSIONAL MEASUREMENT

This application is a continuation of application Ser. No. 07/924,634 filed Aug. 4, 1992, now abandoned.

BACKGROUND OF THE INVENTION

1. Field of the Invention

The present invention relates to an endoscope apparatus for three dimensional measurement, for irradiating a measuring light to a subject to measure three dimensional information of a subject on the basis of an image-pickup signal produced by image pickup means.

2. Description of the Related Art Statement

It has conventionally been known that, in a plurality of images produced by a plurality of optical systems each having a parallax, points corresponding to the same or identical points on a subject are detected and it is determined to how much the points are shifted from each other, whereby a distance to the subject can be computed on the basis of the principle of triangulation.

In a case where points corresponding to the same point on a subject are specified, an observer has conventionally seen an image to execute judgment and has used a pointing unit, such as a light pen or the like, to execute indication. On the other hand, a method has been proposed in Japanese Patent Laid-Open No. SHO 59-187310 in which a scanning spot light is projected on the subject, and a point on each of images corresponding to the same point on the subject is detected without indication by the observer.

Further, as disclosed in Japanese Patent Publication No. HEI 1-43282 and Japanese Patent Laid-Open No. HEI 1-113717, there have been trials in which a laser light is converted into a plurality of spot lights by a fiber lens, and in which a pattern on end surfaces of a plurality of light guide fibers is utilized to produce a plurality of spot lights, the spot lights are projected to an object, and irregularities of the object are measured on the basis of variation in a distance between the spots.

In an apparatus disclosed in the aforesaid Japanese Patent Laid-Open No. SHO 59-187310, scanning of a spot light has been executed by a scanning mechanism which is arranged on a forward end portion of an interior or inside observing unit. Thus, the apparatus disclosed in the aforesaid Japanese Patent Laid-Open No. SHO 59-187310 has a disadvantage that configuration of the forward end portion of the inside observing unit is enlarged. As a result, in a case, for example, where the unit is applied to an endoscope for medical treatment, a diameter of the forward end portion of the endoscope is enlarged, increasing the fear that pain is given to a patient.

Furthermore, in a method disclosed in Japanese Patent Publication No. HEI 1-43282, a distance between spots cannot be measured so that it is difficult to perform spatial resolution.

SUMMARY OF THE INVENTION

It is an object of the invention to provide an endoscope apparatus for three dimensional measurement, in which measurement can be executed with high spatial resolution without enlargement of a forward end portion.

It is another object of the invention to provide an endoscope apparatus for three dimensional measurement, which is superior in operability in which a connecter adjacent to a measuring endoscope is connected at a single connection such that a measuring light of a light-source unit and a normal illuminating light can be supplied.

It is still another object of the invention is to provide an endoscope apparatus for three dimensional measurement, which is variable in a scanning range of a measuring light, and which can execute measurement due to scanning adequate for a using condition or state.

It is a further object of the invention to provide an endoscope apparatus for three dimensional measurement, in which a plurality of measuring lights can be projected toward a subject per unit time, and the projected measuring lights can surely be separated so that many measurements can be executed for a short period of time.

It is another object of the invention to provide an endoscope apparatus for three dimensional measurement, in which an image pickup signal due to an illuminating light is separated from an image pickup signal from image pickup means, whereby three dimensional measurement can surely be executed in a case where halation or the like occurs due to the illuminating light.

It is still another object of the invention to provide an endoscope apparatus for three dimensional measurement, in which an operator can at least recognize that a measuring error is large due to a strong of a reflecting light so that measurement becomes impossible, and in which an illuminating strength of at least a measuring light of a reflecting light and the measuring light can be controlled.

It is a further object of the invention to provide an endoscope apparatus for three dimensional measurement, in which a measuring light from a measuring-light projecting optical system is irradiated to an entire image-pickup area of at least image-pickup means, to execute efficient three-dimensional measurement.

It is another object of the invention to provide an endoscope apparatus for three dimensional measurement, in which a measuring light can consistently be irradiated to a predetermined position with respect to an incident end surface of measuring-light transmitting means without being subjected to an affection or influence of rattle or backlash at a connection between a measuring endoscope and a light-source unit, therefore producing high measuring accuracy.

An endoscope apparatus for three dimensional measurement, according to the invention comprises:
- an endoscope having an inserting section insertable into a body cavity;
- a light source unit having measuring spot light supply means for supplying at least one measuring spot light for three dimensional measurement, and illuminating-light supply means for supplying an illuminating light irradiated in a global or wide area manner;
- optical transmitting means inserted in the inserting section, for transmitting the measuring light and the illuminating light from the light source means to an outgoing end to irradiate the measuring light and the illuminating light to a subject;
- scanning means provided adjacent to an incident end surface of the optical transmitting means, for scanning the measuring spot light in a plane extending perpendicularly to an optical axis of the measuring spot light;

image pickup means for image-picking-up respective return lights of the measuring spot light and the illuminating light irradiated to the subject, from the subject; and distance computing means for image-picking-up the return light of the measuring spot light by the image pickup means, to compute a distance to the subject.

BRIEF DESCRIPTION OF THE DRAWINGS

FIGS. 1 through 3 are views showing a first embodiment of the invention, FIG. 1 being a view for explanation showing an arrangement of an endoscope apparatus for three dimensional measurement, FIG. 2 being a view for explanation showing an incident end surface of an image guide, and FIG. 3 being a view for explanation showing a measuring light on a CCD;

FIG. 4 is a view for explanation, showing an arrangement of an endoscope apparatus for three dimensional measurement according to a second embodiment of the invention;

FIG. 5 is a view for explanation showing an arrangement of a distance measuring system according to a third embodiment of the invention;

FIG. 6 is a view for explanation, showing an arrangement of an endoscope apparatus for three dimensional measurement according to a fourth embodiment of the invention;

FIG. 7 is a view for explanation, showing an arrangement of a measuring-light projecting unit according to a fifth embodiment of the invention;

FIGS. 13 through 17 are views showing a ninth embodiment of the invention, FIG. 13 being a view showing an entire arrangement of the endoscope apparatus for three dimensional measurement according to the first embodiment of the invention, FIG. 14 being a front elevational view showing a forward end surface of a measuring electronic scope, FIG. 15 being a view for explanation, explaining an example of an optical spot appearing on an image-pickup surface of a CCD in a case where a measuring light is scanned at a location adjacent to an incident end surface, FIG. 16 being a principle view for explanation of a principle for computing a distance and the like, and FIG. 17 being a view for explanation explaining a state or manner in which an irregular configuration of an object part is displayed on a monitor screen;

FIGS. 19 and 20 are views showing an eleventh embodiment of the invention, FIG. 19 being a view showing an arrangement of an endoscope apparatus for three dimensional measurement, and FIG. 20 being a view for explanation showing a part of a rotary disc;

FIGS. 21 and 22 are views showing a twelfth embodiment of the invention, FIG. 21 being a view showing an arrangement of an endoscope apparatus for three dimensional measurement, and FIG. 22 being a view for explanation showing a state or manner in which a projecting lens is set to a focal condition in a case where an operating lever Is operated;

FIGS. 23 and 24 are views showing a thirteenth embodiment of the invention, FIG. 23 being a view showing an arrangement of an endoscope apparatus for three dimensional measurement, and FIG. 24 being a view for explanation showing a manner in which a projecting lens is set to a focal condition by a piezo-electric element;

FIGS. 48 through 51 are views showing a twenty-sixth embodiment of the invention, FIG. 48 being a view showing an entire arrangement of an endoscope apparatus for three dimensional measurement, FIG. 49 being a front elevational view showing a forward end portion surface of a measuring electronic scope, FIG. 50 being a view for explanation showing an optical spot image-picked-up by a CCD in a case where a measuring light is scanned at a location adjacent to an incident end surface, and FIG. 51 being a view showing an arrangement of an RGB rotary disc;

FIGS. 52 through 56 are views showing a twenty-seventh embodiment of the invention, FIG. 52 being a view showing an entire arrangement of an endoscope apparatus for three dimensional measurement, FIG. 53 being a block diagram showing an arrangement of a halation/measuring-light spot separating circuit, FIG. 54 being a timing view for explanation of operation of the halation/measuring-light spot separating circuit in a halation area, FIG. 57 being a timing view for explanation of the operation of the halation/measuring-light spot separating circuit in an area of the measuring-light spot, and FIG. 56 being a block diagram showing an arrangement of a modification of the halation/measuring-light spot separating circuit;

FIGS. 58 through 60 are views showing a twenty-ninth embodiment of the invention, FIG. 58 being a view showing an entire arrangement of an endoscope apparatus for three dimensional measurement, FIG. 59 being a front elevational view showing a forward end portion surface of a measuring electronic scope, and FIG. 60 being a view for explanation showing an optical spot image-picked-up by a CCD in a case where a measuring light is scanned at a location adjacent to an incident end surface;

FIGS. 66 through 72 are views showing a thirty-fifth embodiment of the invention, FIG. 66 being a view showing an entire arrangement of an endoscope apparatus for three dimensional measurement, FIG. 67 being a view for explanation showing a forward end portion surface of an electronic scope, FIG. 68 being a view for explanation showing a relationship between a scanning direction and an optical axis of a measuring light and an optical axis of a CCD, FIG. 69 being a view for explanation showing an optical spot image-picked-up by a CCD in a case where a measuring light is scanned at a location adjacent to an incident end surface, FIG. 70 being a view for explanation, showing a manner in which an irregular configuration of an objective part is displayed on a monitor screen, FIG. 71 being a view for explanation showing an optical spot image-picked-up by a CCD in a case of a first modification in which a measuring light is scanned at a location adjacent to an incident end surface, and FIG. 72 being a view for explanation showing an optical spot image-picked-up by a CCD in a case of a second modification in which a measuring light is scanned at a location adjacent to an incident end surface;

FIGS. 76 through 79 are views showing a thirty-ninth embodiment of the invention, FIG. 76 being a view showing an entire arrangement of an endoscope apparatus for three dimensional measurement, FIG. 77 being a view for explanation showing a forward end portion surface of an electronic scope, FIG. 78 being a view for explanation showing a forward end portion surface of a modification of an electronic scope, and FIG. 79 being a view for explanation showing an optical spot image-picked-up by a CCD in a case where a measuring light in FIG. 78 is scanned at a location adjacent to an incident end surface;

FIGS. 84 through 88 are views showing a forty-first embodiment of the invention, FIGS. 84(a)–(b) being views for explanation explaining a relative position between an image guide and a laser spot due to scanning of the laser spot, FIG. 85 being a view for explanation explaining a relative position between an image guide and a laser spot, according to a modification, due to scanning of the laser spot, FIGS. 86(a)–(b) being views for explanation showing a forward end portion surface of an electronic scope, FIG. 87 being a view for explanation explaining scanning due to a plurality of laser spots, and FIG. 88 being a view for explanation explaining two-dimensional scanning of a laser spot.

DETAILED DESCRIPTION OF THE PREFERRED EMBODIMENTS

Various embodiments of the invention will hereunder be described with reference to the accompanying drawings.

A first embodiment of the invention is directed to an endoscope apparatus for three dimensional measurement which uses a stereoscopic electronic endoscope.

Figure 1:
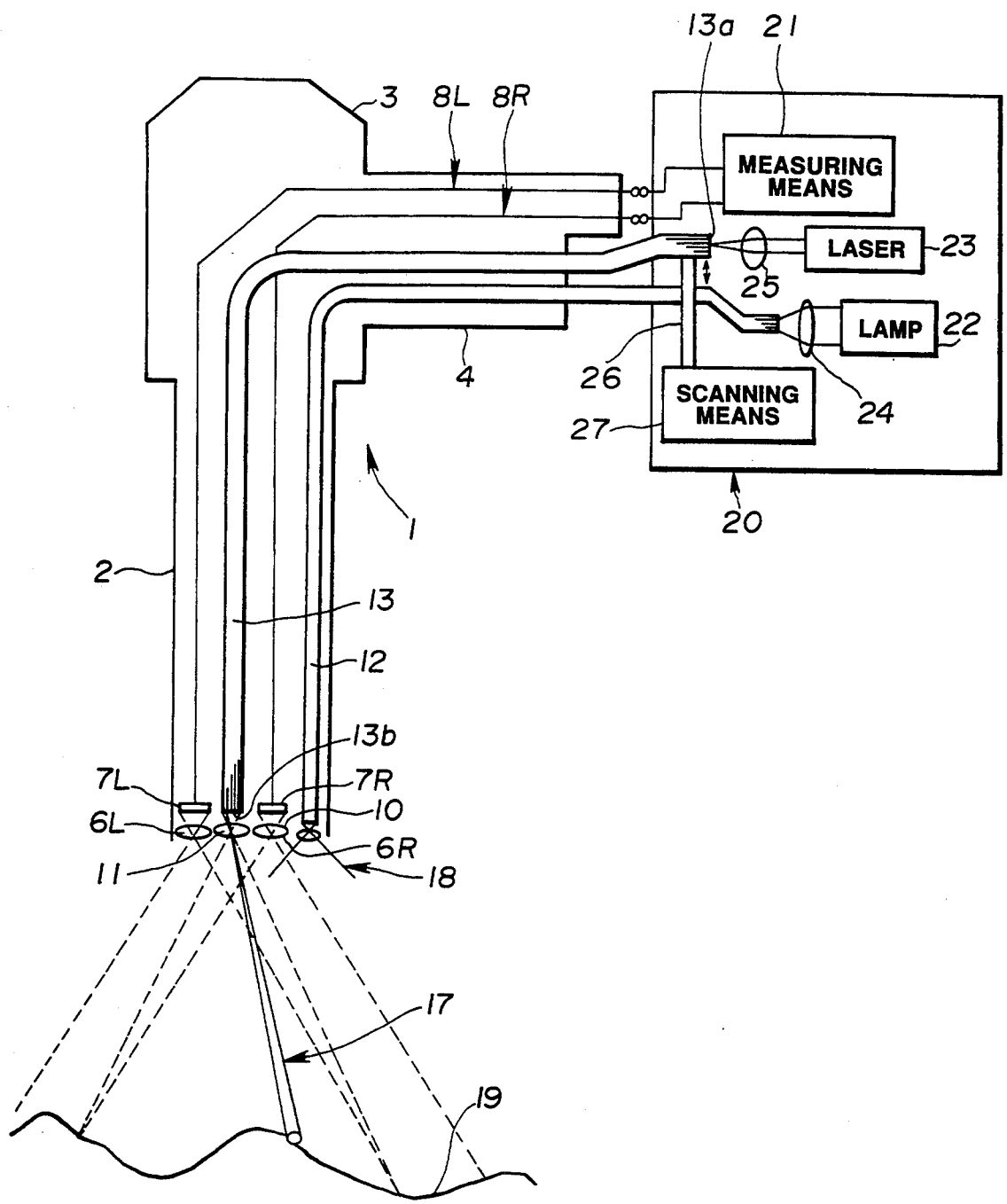

As shown in FIG. 1, the endoscope apparatus for three dimensional measurement comprises a stereoscopic electronic endoscope (hereinafter referred to as an "endoscope") 1 and a measuring-light generating unit 20 to which the endoscope 1 is connected.

The endoscope 1 has an inserting section 2 which is elongated and which has resiliency or elasticity, an operating section 3 connected to a rearward end of the inserting section 2, and a universal cord 4 extending from a side of the operating section 3. The universal cord 4 has an end portion thereof which is connected to the measuring-light generating unit 20. The inserting section 2 has a forward end portion thereof at which a pair of image-pickup lenses 6R and 6L are provided respectively at two locations having a parallax. A pair of CCDs 7R and 7L are arranged respectively at imaging positions of the image pickup lenses 6R and 6L. A pair of signal lines 8R and 8L connected respectively to the CCDs 7R and 7L are inserted in the inserting section 2, the operating section 3 and the universal cord 4, and is connected to measuring means 21 within the measuring-light generating means 20.

Further, a normal or ordinary illuminating lens 10 and a measuring-light projecting lens 11 are arranged at the forward end portion of the inserting section 2. The ordinary illuminating lens 10 has a rearward end to which a light guide 12 is connected. The measuring-light projecting lens 11 has a rearward end to which an image guide 13 consisting of a bundle of glass fibers is connected. The light guide 12 and the image guide 13 are irradiated through the inserting section 2, the operating section 3 and the universal cord 4, and have respective incident ends which are led to a location within the measuring-light generating unit 20.

On the other hand, arranged within the measuring-light generating unit 20 are the measuring means 21, a lamp 22 for emitting the ordinary illuminating light, and a laser 23 for outgoing the measuring light. As described previously, connected to the measuring means 21 are the pair of signal lines 8R and 8L which are connected respectively to the CCDs 7R and 7L. Further, the illuminating light emanating from the lamp 22 is condensed by a condenser lens 24, and is incident upon an incident end surface of the light guide 12. Furthermore, the measuring light emanating from the laser 23 is condensed by a condenser lens 25, and is incident upon an incident end surface 13a of the image guide 13. Moreover, the incident end portion of the image guide 13 is connected to scanning means 27 formed by a piezoelectric element, a speaker (voice coil) or the like, through a connecting member or element 26. The scanning means 27 is operated whereby the scanning means 27 is reciprocally moved in a direction perpendicular to an optical axis of the measuring light.

Operation of the present embodiment will next be described with reference to FIGS. 2 and 3.

A light emanating from the lamp 22 within the measuring-light generating unit 20 is condensed by the condenser lens 24, and is incident upon the incident end surface of the light guide 12. The light passes through the light guide 12 and is irradiated to an object 19 as an illuminating light 18, by an ordinary illuminating lens 10.

Further, a parallel light emanating from the laser 23 within the measuring-light generating unit 20 is condensed by the condenser lens 25, and is projected to the incident end surface 13a of the image guide 13 as a spot image. It is possible to bring a diameter of the spot light approximately to a one (1) micron, and the laser light is projected only upon a single glass fiber (diameter: a few microns) which forms the image guide 13. The laser light is transmitted through the glass fiber, reaches an outgoing end surface 13b of the image guide 13, is emanated and is projected to the object 19 as a measuring light 17 in the form of a spot, by the measuring-light projecting lens 11. The measuring light 17 is a light having spreading or extension. However, a light beam or light flux of the measuring light 17 is very narrow, and a spot light whose minimum resolution is a single glass fiber forming the image guide 13 is projected onto the object. The image guide 13 has an incident end portion which is connected to the scanning means 27 by the connecting element 26. When the connecting element 26 is reciprocated in a direction indicated by an arrow in FIG. 1 by the scanning means 27, the incident end surface 13a of the image guide 13 is also reciprocated in attendance thereupon. As shown in FIG. 2, the image guide 13 is arranged such that glass fibers 14 are regularly arranged. As a result of reciprocation, the glass fibers 14 upon which the laser light is incident change linearly as indicated by marks x in FIG. 2. As a result, the glass fibers 14 from which the laser light is emanated change linearly also in the outgoing end surface 13b of the image guide 13. Since the measuring-light projecting lens 11 projects the laser outgoing end surface to the object 19 as it is, the measuring light 17 on the object 19 that is a spot light whose minimum resolution is a single glass fiber forming the image guide 13 is also moved linearly.

By the above-described operation, scanning of the measuring light 17 projected onto the object 19 is made possible without the provision of a scanning mechanism at the forward end portion of the endoscope 1.

The measuring light 17 projected onto the object 19 is focused or imaged on the CCDs 7R and 7L by the image pickup lenses 6R and 6L. When the scanning means 27 is driven, the measuring light 17 in the L-image and the R-image imaged respectively onto the CCDs 7L and 7R is moved within areas indicated by the broken lines, as shown in FIGS. 3(a) and 3(b). Output signals from the respective CCDs 7R and 7L are inputted to the measuring means 21 within the measuring-light generating unit 20, and a distance and a relative positional relationship between the forward end portion of the endoscope and the measuring light 17 on the object 19 are computed by the measuring means 21. As the computing method, a method can be used which is disclosed in, for example, Japanese Patent Application No. HEI 1-302486 which has previously been filed by the Applicant the same as that of the present invention.

In connection with the above, the arrangement is such that the output signals from the respective CCDs 7R and 7L are processed in image signal by a signal processing circuit (not shown), image signals from the signal processing circuit are inputted to a monitor (not shown), and a left- and a right-hand images of the object are displayed on the monitor.

In this manner, according to the present embodiment of the invention, scanning of the measuring light 17 projected onto the object 19 is made possible without enlargement of the configuration of the forward end portion of the endoscope 1, whereby measurement high in spatial resolution is made possible.

An endoscope apparatus for three dimensional measurement according to a second embodiment of the invention will next be described.

The endoscope apparatus for three dimensional measurement according to the present embodiment comprises, as shown in FIG. 4, an endoscope 1, a measuring unit 30 and a light source unit 50 to which the endoscope 1 is connected, and a color monitor 55 connected to the measuring unit 30. The endoscope 1 has an image guide 13 whose incident end and a pair of signal lines 8R and 8L are connected to the measuring unit 30. A light guide 12 has an incident end portion which is connected to the light source unit 50.

The measuring unit 30 has a semiconductor laser 31 and a condenser lens 32 for condensing a light emanated from the semiconductor laser 31 to project the condensed light to an incident end surface of the image guide 13. The semiconductor laser 31 and the condenser lens 32 are integrated with each other, and are reciprocated in a direction perpendicular to the optical axis by a speaker 33 which is connected through a connecting element 34. With the arrangement, similarly to the first embodiment, glass fibers upon which the laser light is incident change so that the measuring light 17 projected onto the object 19 is scanned. The semiconductor laser 31 is driven by a laser drive circuit 35. Further, the measuring unit 30 is provided with a clock generator 36. Clocks generated by the clock generator 36 are inputted to a counter 37. An output from the counter 37 is inputted to a D/A converter 38 and a comparator 39. An output from the D/A converter 38 is inputted to the speaker 33 through an amplifier 40. An upper-limit preset value and a lower-limit preset value from a preset-value generating circuit 41 are inputted to the comparator 39. The comparator 39 sends an output which is inverted when the output from the counter 37 reaches the upper-limit or lower-limit preset value, to the counter 37. The counter 37 switches counting-up and counting-down when the signal from the comparator 39 is inverted.

The measuring unit 30 has the video circuit (R) 43R and the video circuit (L) 43L. Outputs from the respective CCDs 7R and 7L of the endoscope 1 are inputted respectively to the video circuits 43R and 43L. Outputs from the respective video circuits 43R and 43L are inputted respectively to a measuring-light position detecting circuit (R) 44R and a measuring-light position detecting circuit (L) 44L. Outputs from the respective measuring-light position detecting circuits 44R and 44L are inputted to a distance computing means 45. An output from the distance computing means 45 is inputted to distance information display means 46. An output from the distance information display means 46 is inputted to the color monitor 55.

Furthermore, the light source unit 50 has a lamp 51 consisting of a xenon lamp or the like outgoing an ordinary illuminating light, a lamp drive circuit 52 for driving the lamp 51, and a condenser lens 53 for condensing a light emanated from the lamp 51 to cause the condensed light to be incident upon the incident end surface of the light guide 12.

Operation of the present embodiment will next be described.

The clocks from the clock generator 36 are inputted to the counter 37, and the counter 37 first executes counting-up. The output from the counter 37 is converted to an analog signal by the D/A converted 37. Accordingly, the output from the D/A converter 37 increases in accordance with counting-up of the counter 37. The output from the D/A converter 38 is sent to the speaker 33 through the amplifier 40, and the speaker 33 is gradually driven forwardly. The output from the counter 37 is inputted also to the comparator 39. When the output from the counter 37 reaches the upper-limit preset value, the output from the comparator 39 is inverted, and the counter 37 initiates down-counting operation. As a result, the output from the D/A converter 38 gradually decreases, and the speaker 33 is gradually moved rearwardly. When the counter 37 reaches the lower-limit preset value, the output from the comparator 39 is again inverted, and the counter 37 initiates counting-up. The speaker 33 continues reciprocal movement in this manner and, in attendance thereupon, the semiconductor laser 31 and the condensing lens 32 are reciprocally moved integrally.

On the other hand, output signals from a pair of CCDs 7R and 7L are video-signaled respectively by the video circuits 43R and 43L, and are inputted to the measuring-light position detecting circuits 44R and 44L. At the measuring-light position detecting circuits 44R and 44L, it is detected as to where on the video images the images of the measuring light are. The measuring-light position detecting circuits 44R and 44L output a pair of horizontal-direction coordinates, respectively, with a left-hand end of the video image serving as a reference. The distance computing means 45 uses the coordinates outputted respectively from the measuring-light position detecting circuits 44R and 44L, to compute a distance to the measuring light on the object from the forward end portion of the endoscope, and inputs the computed distance to the distance information display means 46. This operation is executed over the entire area of the scanning range, whereby there can be produced irregularity information on the surface of the scanning region. The distance information display means 46 displays the obtained distance information on the color monitor 55 in various forms or configurations. FIG. 4 shows an example in which scanning ranges 56R and 56L of the measuring light and cross-sectional configurations 57R and 57L of the surface of the scanning region are displayed together with a right-hand image 58R and a left-hand image 58L. In this connection, a method of computing a distance from the forward end portion of the endoscope to the measuring light on the object can use the method disclosed in, for example, Japanese Patent Application No. HEI 1-302486 which has previously been filed by the Applicant the same as that of the present invention, similarly to the first embodiment.

Further, the arrangement is such that, apart from the measuring light, an ordinary or normal illuminating light is emanated from the forward end portion of the endoscope by the lamp 51, the condenser lens 53 and the light guide 12 so that general observation can be executed.

In connection with the above, the arrangement may be such that an optical single point on the scanning range is assigned by a pointing unit such as a mouse or the like, and a distance to the point is displayed by numeral values.

Moreover, if the semiconductor laser 31 is turned on/off at a high speed in synchronism with the scanning, the laser light can be incident only upon an optional glass fiber in the image guide 13. Accordingly, if it is possible to select as to upon what fiber the laser light is incident, it is possible to know a distance to an optional point within the scanning range on the forward end portion of the endoscope and the object 19.

Other arrangement, function and advantages are similar to those of the first embodiment.

An endoscope apparatus for three dimensional measurement according to a third embodiment of the invention will next be described.

The endoscope apparatus for three dimensional measurement according to the third embodiment of the invention comprises, as shown in FIG. 5, an endoscope 1, a measuring unit 60 and a light source unit 50 to which the endoscope 1 is connected, an image guide probe 66 inserted in a forceps channel 64 in the endoscope 1, and a measuring-light generating unit 70 to which the image guide probe 66 is connected. The endoscope 1 has a pair of signal lines 8R and 8L which are connected to the measuring unit 60. A light guide 12 has an incident end portion which is connected to the light source unit 50. The arrangement of the light source unit 50 is similar to that of the light source unit 50 in the second embodiment.

The endoscope 1 in this embodiment is arranged such that the image guide leading the measuring light is not built therein, but the forceps channel 64 is provided which extends from a forceps bore 65 in an operating section 3 to an opening in a forward end portion of an inserting section 2. The image guide probe 66 for leading the measuring light is inserted in the forceps channel 64. The image guide probe 66 has an image guide 67 consisting of a bundle of glass fibers, and a measuring-light projecting lens 68 arranged at the forward end surface of the image guide 67 in opposed relation thereto. The image guide probe 66 has an incident end portion which is connected to the measuring-light generating unit 70.

The measuring-light generating unit 70 includes a HeNe laser 71, a collimator lens 72 for bringing a light from the HeNe laser 71 to a parallel light, a prism 73 from which a light through the collimator lens 72 is reflected, and a condensing lens 74 for condensing a light reflected from the prism 73 to cause the reflected light to be incident upon the incident end surface of the image guide probe 66. The prism 73 and the condensing lens 74 are integrated with each other, and are moved reciprocally in a direction perpendicular to an optical axis by a speaker 33 connected through a connecting member or element. Thus, the glass fibers upon which the laser light is incident change. The HeNe laser 71 is driven by a laser drive circuit 75, and the speaker 33 is driven by a speaker drive circuit 76.

On the other hand, the measuring unit 60 is provided with a video circuit (R) 43R and a video circuit (L) 43L which are connected respectively to a pair of CCDs 7R and 7L of the endoscope 1 through the pair of signal lines 8R and 8L. Outputs from the respective video circuits 43R and 43L are inputted to a coordinate measuring circuit 61. An output from the coordinate measuring circuit 61 is inputted to coordinate display means 62.

Operation of the present embodiment will next be described.

The image guide probe 66 is inserted into the forceps channel 64 in the endoscope 1 from the forceps bore 65, and projects from the forward end of the endoscope. An outgoing light from the HeNe laser 71 is projected to the incident end surface of the image guide probe 66 through the collimator lens 72, the prism 73 and the condensing lens 74 as a minute spot light. The prism 73 and the condensing lens 74 are moved reciprocally by the speaker 33, and the glass fibers upon which the laser light is incident are scanned. In attendance thereupon, the measuring light projected to an object 19 by the measuring-light projecting lens 68 is also scanned.

The measuring light is image-picked-up by the CCDs 7R and 7L, is video-signaled by the video circuits 43R and 43L, and is inputted to the coordinate measuring circuit 61. The coordinate measuring circuit 61 is formed by a computer and the like, and computes coordinates of a measuring light 17 on the object 19 with respect to the forward end of the endoscope, on the basis of the fact as to where the measuring-light image is positioned with respect to left- and right-hand images. The coordinates are inputted to the coordinate display means 62 formed by a TV monitor and the like, and are displayed by the coordinate display means 62 in terms of numerical values or graphics. In this connection, a method of computing the coordinates of the measuring light on the object with respect to the forward end of the endoscope can use the method disclosed, for example, in Japanese Patent Application No. HEI 1-302486 which has been filed by the Applicant the same as that of the present invention, similar to the first embodiment.

In connection with the above, a diameter of the image guide probe 66 does merely a few millimeters even if the numbers of fibers of the image guide 67 are a few ten thousands, and it is extremely easy to insert the image guide probe 66 from the forceps channel 64.

Other arrangement, function and advantages are similar to those of the first embodiment.

An endoscope apparatus for three dimensional measurement according to a fourth embodiment of the invention will next be described.

The endoscope apparatus for three dimensional measurement according to the present embodiment of the invention comprises, as shown in FIG. 6, a color-successive-type (surface-successive-type) electronic endoscope 81 and a control unit 90 to which the endoscope 81 is connected.

In the endoscope 81, a pair of CCDs 7R and 7L are of color successive (surface successive) type. Furthermore, a measuring-light transferring image guide 13 has an incident end portion which is arranged within an operating section 3. Arranged within the operating section 3 are a semiconductor laser 31, a collimator lens 72 for bringing a light from the semiconductor laser 31 to a parallel light, a prism 73 for reflecting a light passing through the collimator lens 72, a condensing lens 74 for condensing a light reflected from the prism 73 to cause the reflected light to be incident upon an incident end surface of the image guide 13, and a speaker 33. The prism 73 and the condensing lens 74 are integrated with each other, and are moved reciprocally in a direction perpendicular to an optical axis by the speaker 33 connected through a connecting member or element. Thus, glass fibers upon which the laser light is incident change. The semiconductor laser 31 is connected to a laser drive circuit 75 within the control unit 90 through a signal line 83. The speaker 33 is connected to a speaker drive circuit 76 within the control unit 90 through a signal line 84. Moreover, a measuring switch 82 for generating a measuring command signal is provided at the operating section 3. The rest of the arrangement of the electronic endoscope 81 is similar to that of the endoscope 1 in the first embodiment.

On the other hand, a lamp 91 for emanating the ordinary illuminating light is provided within the control unit 90. A condenser lens 92 and a rotary color disc 93 are arranged in order from the lamp 91, on an optical path extending between the lamp 91 and an incident end of a light guide 12. The rotary color disc 93 has filters through which lights having wavelength areas of respective red (R), green (G) and blue (B) arranged circumferentially pass. The rotary color disc 92 is rotated by a motor 94 so that the filters are successively interposed in the illuminating light paths. Further, a shutter 95 capable of being inserted and withdrawn is provided on the illuminating-light path between the lamp 91 and the condenser lens 92. The shutter 95 is driven by shutter drive means 96 formed by a solenoid or the like. The shutter drive means 96 is controlled by a shutter control circuit 97.

Furthermore, arranged within the control unit 90 are a pair of video circuits 43R and 43L connected respectively to the CCDs 7R and 7L of the electronic endoscope 81, the laser drive circuit 75 connected to the semiconductor laser 31, and the speaker drive circuit 76 connected to the speaker 33. Outputs from the respective video circuits 43R and 43L are inputted to a coordinate measuring circuit 61. An output from the coordinate measuring circuit 61 is inputted to coordinate display means 62. Moreover, arranged within the control unit 90 is a timing controller 98 for controlling the laser drive circuit 75, the speaker drive circuit 76 and the shutter control circuit 97. A measuring command signal from the measuring switch 82 of the electronic endoscope 81 is inputted to the timing controller 98.

Operation of the present embodiment will next be described.

Color successive lights of red, green and blue are generated by the lamp 91, the condenser lens 92 and the rotary color disc 93 within the control unit 90. These color successive lights are led to the forward end of the electronic endoscope 81 by the light guide 12 to illuminate an object 19. An image of the object 19 illuminated by the color successive lights is image-picked-up by the CCDs 7R and 7L, is video-signaled by the video circuits 43R and 43L, and is observed by a color monitor (not shown) or the like.

In a case where irregularities of the object 19 are measured, an operator depresses the measuring switch 82 provided at the operating section 3 of the electronic endoscope 81. Then, the measuring command signal is inputted to the timing controller 98 within the control unit 90 through a signal line (not shown). The timing controller 98 drives the shutter control means 96 through the shutter control circuit 97, and the shutter 95 is inserted into the optical path of the color-successive-light generating lamp 91. As a result, illumination due to the color successive lights stops.

Subsequently, the timing controller 98 operates the laser drive circuit 75 and the speaker drive circuit 76, radiates the semiconductor laser 31 within the endoscope 81 and, simultaneously, reciprocally moves the prism 73 and the condensing lens 74 connected to the speaker 33. Driving of the speaker 33 is executed in synchronism with rotation of the rotary color disc 93, and the speaker 33 repeats reciprocal movement at a predetermined frame cycle.

In a case of the color successive type electronic endoscope which uses a frame transfer CCD which executes electric-charge storage or accumulation and electric-charge transmission with the same or identical area, it is required that a light is not applied to the CCD during electric-charge transmission of the CCD. In view of this, the timing controller 98 turns on/off the semiconductor laser 31 in synchronism with rotation of the rotary color disc 93, and radiates the laser light only during a period of time the same as that of the original color successive light. As a result, there can be produced the ordinary illuminating image and the image signal due to the measuring light as an ordinary video signal, from the video circuits 43R and 43L.

The outputs from the respective video circuits 43R and 43L are inputted to the coordinate measuring circuit 61 which is formed by a computer and the like, similarly to the third embodiment. Coordinates of a measuring light 17 on the object 19 are computed by the coordinate measuring circuit 61 with the forward end of the endoscope serving as a reference, and the coordinates are displayed by the coordinate display means 62.

Other arrangements, functions and advantages are similar to those of the third embodiment.

A measuring-light projecting apparatus according to a fifth embodiment of the invention will next be described.

The measuring-light projecting apparatus according to the present embodiment is provided with a pigment laser 101 variable in wavelength, as a laser for outgoing a measuring light, as shown in FIG. 7. The laser light emanating from the pigment laser 101 is condensed by a condensing lens 102, is incident upon a light guide 103 formed by one or a plurality of glass fibers, is led to the other end of the light guide 103, and is emanating. The outgoing end portion of the light guide 103 is connected to an actuator 105 formed by a piezo-electric element or the like, through a connecting member or element 104. The outgoing end of the light guide 108 is moved reciprocally in a direction perpendicular to an optical axis in accordance with movement of the actuator 105. A light emanating from the outgoing end of the light guide 103 is projected in reduction to an incident end 107a of an image guide 107 formed by a bundle of glass fibers, by a reduction lens 106. If a diameter of the image guide 107 and a reduction magnification of the reduction lens 106 are suitably selected, an image of the outgoing end of the light guide 108 projected to the incident end 107a of the image guide 107 can be brought to a value equal to or less than a few microns. As a result, it is possible to cause the light from the light guide 108 to be incident upon a single glass fiber which forms the image guide 107. The light transferred to an outgoing end 107b of the image guide 107 is projected to an object 109 as a measuring light 17, by a measuring-light projecting lens 108.

The measuring-light projecting apparatus according to the present embodiment can be applied to any of the first to fourth embodiments. Specifically, the image guide 107 may be built in the endoscope, as is in the first or second embodiment, or the image guide 107 may be inserted through the forceps channel in the endoscope, as is in the third embodiment. Further, the measuring-light projecting unit may be applied to the color successive type electronic endoscope, as is in the fourth embodiment.

The pigment laser 101 can alter or change the wavelength of the light generated by the pigment laser 101. Accordingly, if the present embodiment 1s applied, it is possible to measure irregularities or size or magnitude of the object in various wavelengths. Particularly, if an infrared light which is transmitted through a body surface to reach a location within the body is used, it is possible to measure size or dimension of a blood vessel and a depth thereof within an organism. Thus, the medical value is great.

Other functions and advantages are similar to those of the first embodiment.

A measuring-light projecting apparatus according to a sixth embodiment of the invention will next be described.

Figure 8:
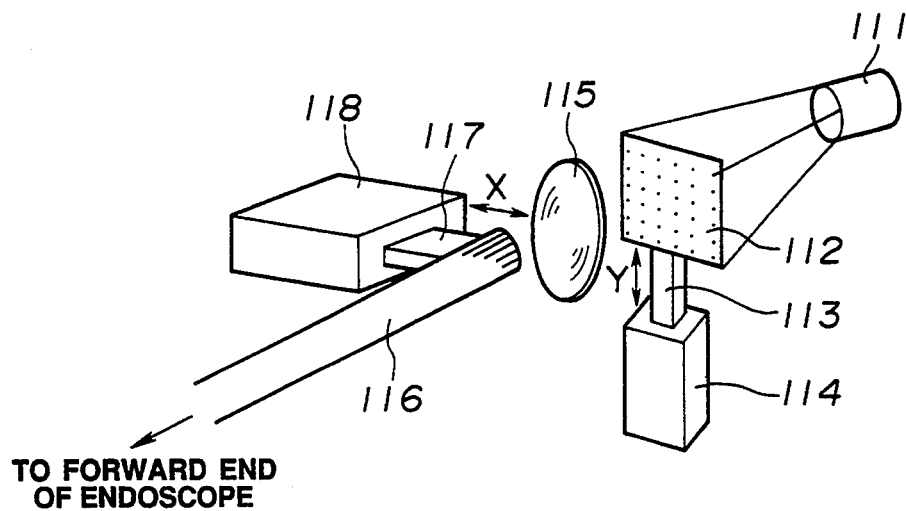
FIGS. 8 and 9 are views showing a sixth embodiment of the invention, FIG. 8 being a perspective view showing an arrangement of a principal portion of a measuring-light projecting unit, and FIG. 9 being a view for explanation showing movement of a pin-hole image on an image guide.

The measuring-light projecting apparatus according to the present embodiment is provided with a lamp 111 as illustrated in FIG. 8. A pin-hole plate 112 in which a plurality of pin holes are formed is arranged on an optical path of an outgoing light from the lamp 111. The pin-hole plate 112 is connected to an actuator 114 through a connecting element 113, and is moved reciprocally by the actuator 114 in a Y-direction perpendicular to an optical-axis direction. An image of the pin-hole plate 112 is projected in reduction to an incident end surface of an image guide 116 by a reduction lens 115. The image guide 116 has an incident end portion which is connected to the actuator 118 through a connecting element 117. The image guide 116 is moved reciprocally by the actuator 118 in an optical-axis direction and an X-direction perpendicular to the Y-direction. The image of the pin-hole plate 112 projected to the incident end surface of the image guide 116 is led to a forward end of an endoscope, and is projected to an object by a measuring-light projecting lens (not shown).

The measuring-light projecting unit according to the present embodiment can be applied to any of the first to fourth embodiments, similarly to the fifth embodiment.

Figure 9:
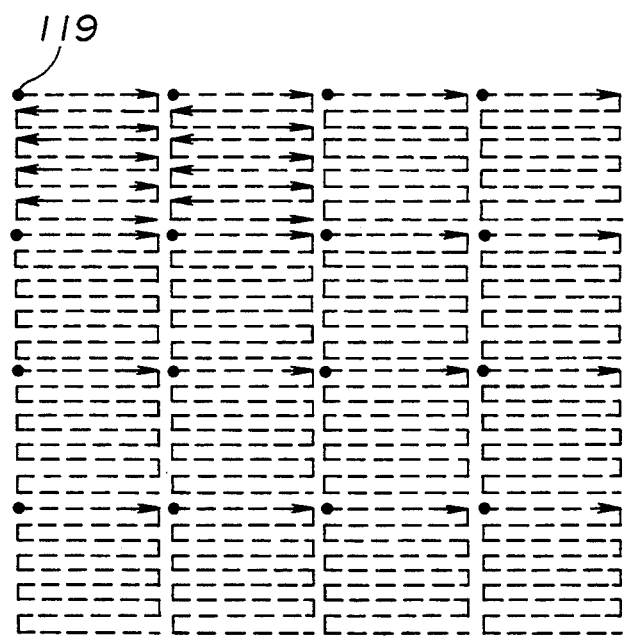

In the present embodiment, when the actuators 114 and 118 are driven at suitable timing, a plurality of pin-hole images 119 on the image guide 116 move on the incident end surface of the image guide 116 as illustrated in FIG. 9. As a result, even a small amount of driving of the actuators 114 and 118 makes it possible to scan the entire incident end surface of the image guide 116 by the pin-hole image 119. For example, one of the plurality of pin-hole images 119 projected on the object is assigned by a pointing device to obtain a distance from the forward end of the endoscope to the pin-hole image 119 and the coordinates of the pin-hole image 119 with respect to the forward end of the endoscope and to assign the two pin-hole images 119 to obtain a distance therebetween.

It is possible to judge which pin holes on the pin-hole plate 112 the plurality of pin-hole images 119 projected onto the object correspond to, by the fact that the size or dimension of a pin hole (for example, a central pin hole) serving as a reference is changed or varies, or by the fact that a color filter is stuck to the pin hole to change a color of the light passing from the reference pin hole.

In connection with the above, if the pin hole is enlarged, the pin hole is projected to the plurality of glass fibers of the image guide 116. However, measuring-space resolution adjacent to the pin hole is only reduced. Thus, practically there is not much of a problem practically.

Other functions and advantages are similar to those of the first embodiment.

A measuring-light projecting apparatus according to a seventh embodiment of the invention will next be described.

Figure 10:
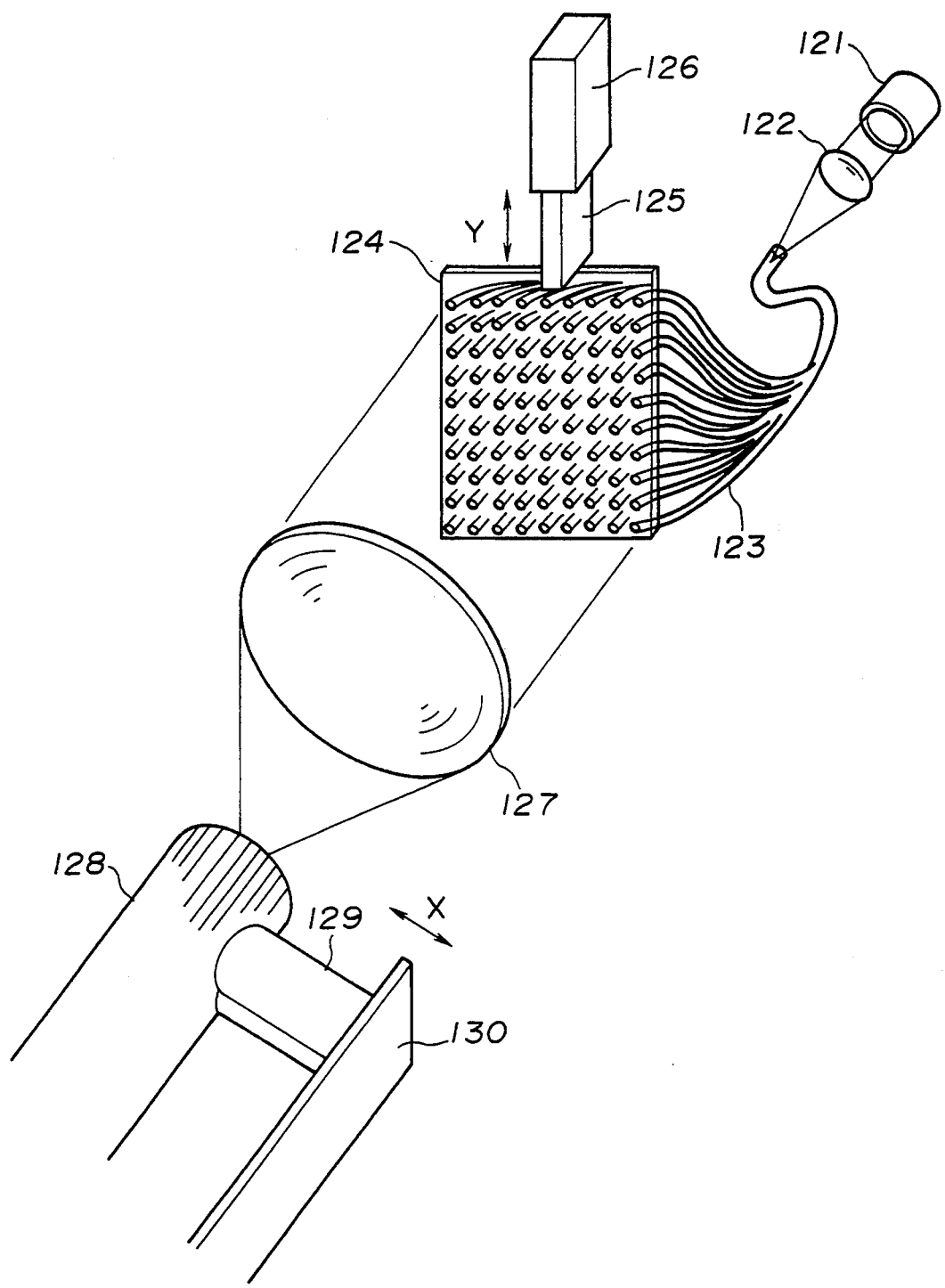
FIG. 10 is a perspective view showing an arrangement of a principle portion of a measuring-light projecting unit according to a seventh embodiment of the invention.

As shown in FIG. 10, the measuring-light projecting apparatus according to the present embodiment is provided with a lamp 121. An outgoing light from the lamp 121 is condensed by a condenser lens 122 and is incident upon respective incident ends of a plurality of glass fibers 123. The incident end portions of the plurality of glass fibers 123 are bundled up, and the light from the lamp 121 is incident upon all the glass fibers 123. The outgoing end portions of the plurality of glass fibers 123 are regularly arranged on a retaining plate 124. The retaining plate 124 is connected to a linear motor 126 through a connecting element 12S, and is moved reciprocally in a Y-direction perpendicular to an optical-axis direction due to the linear motor 126. Images of the respective outgoing ends of the glass fibers 123 are projected in reduction to an incident end surface of the image guide 128 by a reduction lens 127. The incident end portion of the image guide 128 is connected to a piezo-electric bimorph 130 through a connecting element 129, and is moved reciprocally by the piezo-electric bimorph 130 in the optical-axis direction and an X-direction perpendicular to the Y-direction. The images of the outgoing ends of the glass fibers 123 projected to the incident end surface of the image guide 128 are led to a forward end of an endoscope, and are projected to an object by a measuring-light projecting lens (not shown).

The measuring-light projecting apparatus according to the present embodiment can be applied to any of the first to fourth embodiments, similarly to the fifth and sixth embodiments.

Other functions and advantages are similar to those of the sixth embodiment.

An endoscope apparatus for three dimensional measurement according to an eighth embodiment of the invention will next be described.

The present embodiment is directed to the endoscope apparatus for three dimensional measurement in which three dimensional coordinates of a measuring light on an object with a forward end of the endoscope serving as a reference can be produced by the endoscope provided with a single CCD.

Figure 11:
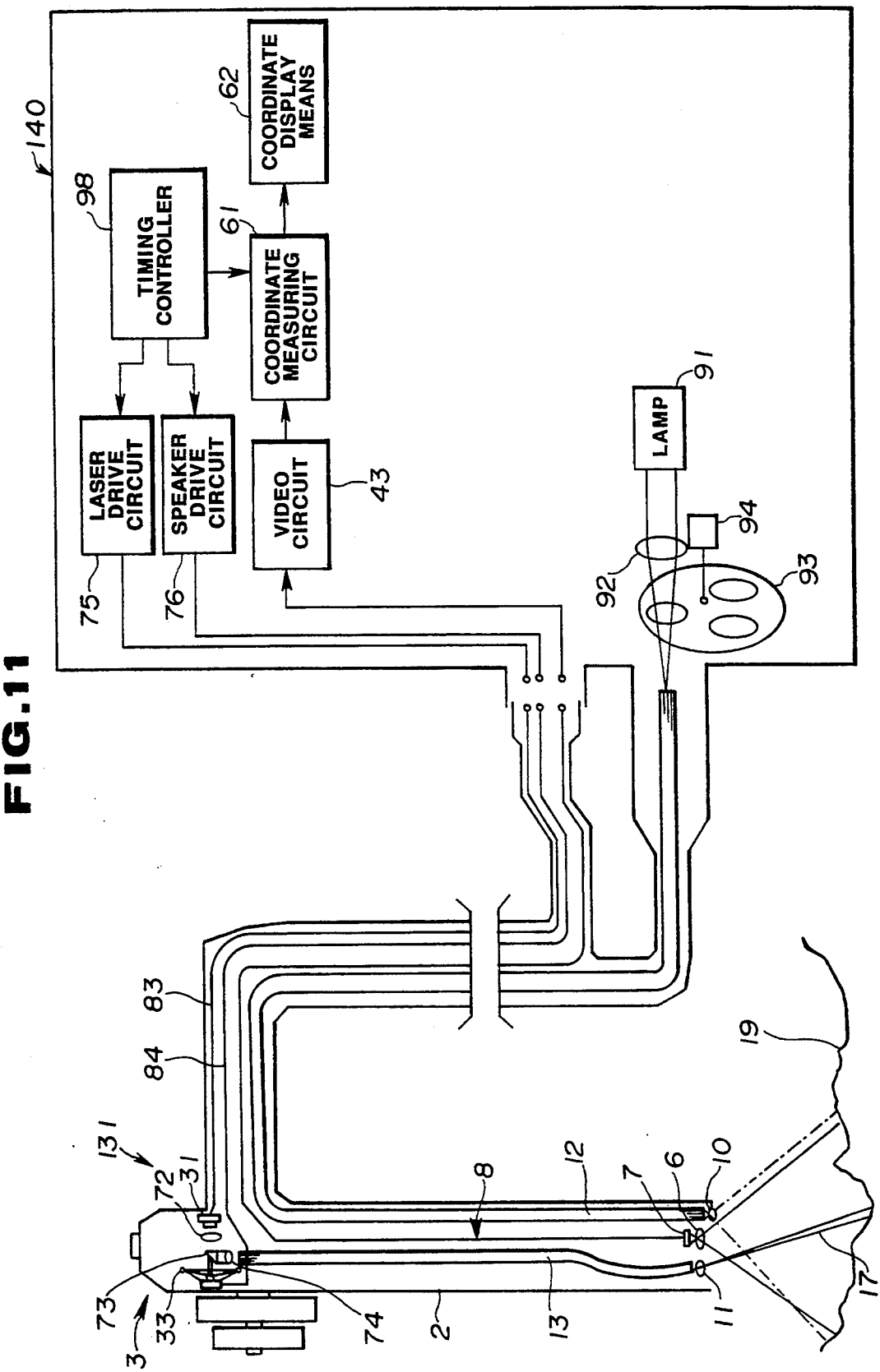
FIGS. 11 and 12 are views showing an eighth embodiment of the invention, FIG. 11 being a view for explanation showing an arrangement of an endoscope apparatus for three dimensional measurement, and FIG. 12 being a block diagram showing an example of a coordinate measuring circuit.

As shown in FIG. 11, a distance measuring system of the present embodiment is provided with an electronic endoscope 131 and a control unit 140 to which the endoscope 131 is connected.

The endoscope 131 is arranged such that a single image pickup lens 6, a CCD 7 and a signal line 8 are substituted for the two image pickup lenses 6R and 6L, the pair of CCDs 7R and 7L and the pair of signal lines 8R and 8L in the electronic endoscope 81 illustrated in FIG. 6.

On the other hand, the control unit 140 is arranged such that, in the control unit 90 illustrated in FIG. 6, a single video circuit 43 is substituted for the two video circuits 43R and 43L, and the shutter 95, the shutter control means 96 and the shutter control circuit 97 are omitted. In this connection, a coordinate measuring circuit 61 in the present embodiment is controlled by a timing controller 98.

Operation of the present embodiment will next be described.

A light emanating from a semiconductor laser 31 is converted to a parallel light by a collimator lens 72 formed by an aspherical lens, and is reflected by a prism 73 and, subsequently, is projected to an incident end of a image guide 13 by a condensing lens 74 as a minute spot light having a diameter equal to or less than 1 micron. The spot light is transmitted to the outgoing end surface of the image guide 13, and is projected to an object 19 by a measuring-light projecting lens 11. The prism 73 and the condensing lens 74 are connected to a speaker 33 by a connecting element, and the laser spot on the incident end of the image guide 13 is scanned in accordance with the reciprocal movement of the speaker 33.

Apart from the above, a color successive light is formed by a lamp 91, a condenser lens 92 and a rotary color disc 93 as an ordinary illuminating light for observation, is sent to the forward end portion of the endoscope through a light guide 12, and is irradiated to the object 19 by an illuminating lens 10.

The semiconductor laser 31 is driven In synchronism with irradiation of the color successive light, and the object 19 is not illuminated by the measuring light and the ordinary observing light at turning-off of the semiconductor laser 31.

The measuring light projected to the object 19 is imaged to the CCD 7 by the image pickup lens 6, together with the reflected light of the ordinary observing light due to the object. An output from the CCD 7 is converted to a video signal by the video circuit 43, and coordinates of a measuring light 17 on the object 19 with respect to the forward end of the endoscope are computed by the coordinate measuring circuit 61. The computed coordinates are displayed by coordinate display means 62.

Information on the position of the speaker 33 is sent from the timing controller 98 to the coordinate measuring circuit 61. The coordinate measuring circuit 61 computes the coordinates of the measuring light on the object with the forward end of the endoscope serving as a reference, from the information on the position of the speaker 33 and the position of the measuring light image obtained from the video circuit 43.

Figure 12:
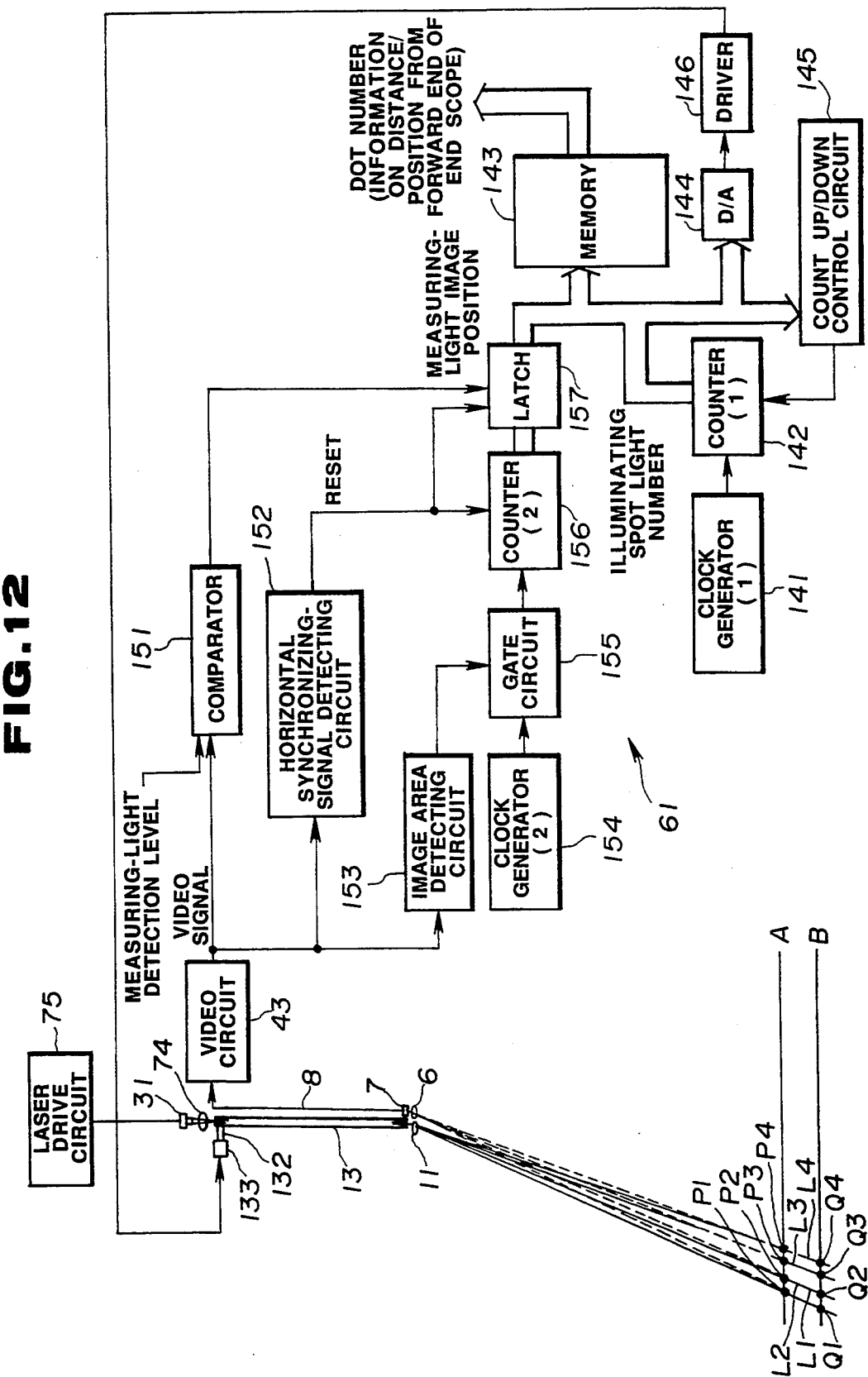

In connection with the above, as shown in FIG. 12, the arrangement may be such that the incident end portion of the image guide 13 is connected to an actuator 133 formed by a piezo-electric element and the like, through a connecting element 132, and the incident end of the image guide 13 is moved reciprocally by the actuator 133, to scan the laser spot.

The principle of measurement in the coordinate measuring circuit 61 will next be described.

As shown in FIG. 12, it is assumed that points of intersection between measuring lights L1, L2, L3 and L4 emanated from the outgoing end of the image guide 13 and a plane A are P1, P2, P3 and P4, and points of intersection between the measuring lights L1, L2, L3 and L4 and a plane B are Q1, Q2, Q3 and Q4. In this connection, it is assumed that the planes A and B are parallel to each other, and are perpendicular to an optical axis of a measuring-light projecting lens 11.

In a case where these points P1~P4 and Q1~Q4 are image-picked-up by an image pickup lens 6 and a CCD 7, the point P1 and the point Q1 on the measuring light L1 are image-picked-up under such a condition that their positions are different from each other. This is because positions of the respective projecting optical system and image pickup optical system of the measuring light are different from each other. Similarly, P2 and Q2, P3 and Q3 and P4 and Q4 are image-picked-up as different points, respectively. Further, the measuring lights L1, L2, L3 and L4 are uniquely determined in correspondence to displacement of the actuator 133 (or the speaker 33).

As a result, if it is known at what position on the CCD 7 the measuring light on the object is imaged and how the displacement of the actuator (or the speaker 33) is at this time, an absolute position of the measuring light on the object is determined or decided.

An example of the coordinate measuring circuit 61 will next be described with reference to FIG. 12.

An output from the clock generator (1) 141 is counted up by a counter (1) 142. The count value is connected to a low-order bit of an address input of a memory 143 formed by a semiconductor memory of large capacity or the like, and is inputted to a D/A converter 144 and a counting UP/DOWN control circuit 145. An output from the D/A converter 144 is inputted to the actuator 133 through a driver 146, and the actuator 133 is displaced in accordance with a counting value of the counter (1) 142. As a result, the incident end portion of the image guide 13 connected to the actuator 133 through the connecting element 132 is also displaced so that the measuring light is irradiated in order of L1, L2, L3 and L4. Further, the counting UP/DOWN control circuit 145 switches the counter (1) 142 to count-down operation when the counting value of the counter (1) 142 reaches a predetermined value, whereby the counter (1) 142 initiates counting-down, and the actuator 133 is moved reciprocally.

On the other hand, the output from the CCD 7 is video-signaled by the video circuit 43, and is inputted to a comparator 151, a horizontal synchronizing signal detecting circuit 152, and a image area detecting circuit 153. An output from a clock generator (2) 154 formed by a quartz oscillator or the like is inputted to a gate circuit 155. The gate circuit 155 inputs the clock signal to a counter (2) 156 only in a case where a signal of an image portion of the video signals is outputted, on the basis of the output from the image area detecting circuit 153. Generally, since the endoscope using the CCD is only a partial area of the video signal of the output, on which the image is displayed, with respect to the entire video screen, this gate is necessary in order to bring the left-hand end of the image area to the coordinates 0.

On the other hand, the comparator 151 executes comparison with the measuring-light detecting level, to detect only the signal corresponding to the measuring light from the inputted video signal. An output from the comparator 151 is inputted to a latch 157 as a control input. A value of the counter (2) 156, that is, the coordinates of the measuring light with the left-hand end of the image area of the video signal serving as a reference are stored in the latch 157. Further, the horizontal synchronizing signal detecting circuit 152 separates the horizontal synchronizing signal from the video signal, and resets the latch 157 and the counter (2) 156 during the blanking period of time. An output from the latch 157 is connected to the upper-order bit of the address input of the memory 143.

As described previously, if the position of the projected measuring light and the position of the measuring-light image are known, the position of the measuring light projected to the object is uniquely determined. In the present example, illuminating spot light numbers from the counter (1) 142 corresponding to the position of the measuring light, and the illuminating-light image position from the latch 157 are so arranged as to be given to the upper-order bit and the low-order bit of the address input of the memory 143, and outputs the dot numbers as information of the measuring light, regarding the distance/position from the forward end of the endoscope, from the memory 143 correspondingly to the address. For example, if the coordinates of the measuring light on the object with respect to the forward end of the endoscope are stored in the memory 143, it is possible to compute the coordinates of the measuring light on the object, only for reading-out time within the memory 143.

If the actual endoscope is used to prepare data written to the memory 143 to scan the measuring light, and if the position of the measuring light projected to various planes is measured by the counter (2) 156 so that the measuring value is written, aberration, assembling errors and the like of the measuring-light projecting lens 11 and the image pickup lens 6 can be corrected.

In connection with the above, although the present embodiment uses the semiconductor memory as the memory 143, the invention should not be limited to this specific embodiment, but a magnetic disc or an optical disc may be used. In that case, administration of the address input and the physical address of the disc can easily be realized by a controller for the magnetic disc or the optical disc.

An optical disc is put to a practical use even if the optical disc has a capacity of several giga bytes. In this case, an address input corresponds to 30~32 bits on the assumption of a case of an output in terms of a byte unit. Here, a memory capacity required for a case where measurement is executed with respect to the entire screen will be considered. In a case where seven (7) bits (128) are used in the horizontal direction, and seven (7) bits (128) in the vertical direction are used, in order to specify a measuring light, and seven (7) bits (128) used in the horizontal direction, and seven (7) bits (128) in the vertical direction are used, in order to specify a position of the measuring light, the memory capacity is twenty-eight (28) bits (256×10). Even if two (2) bits in each of the X, Y and Z coordinates, total six (6) bits are assumed as an output from the memory, an address input required for the optical disc is merely thirty-one (31) bits (2×10). Thus, a sufficient capacity can be secured or ensured by the optical disc. Although the capacity is slightly less in a case of the magnetic disc or the optical magnetic disc, a plurality of disc units should be used in this case.

As described above, the coordinates of the measuring light on the object can be specified by the magnetic disc or the optical disc, with the forward end of the endoscope serving as a reference, without the use of a complicated computing circuit.

Moreover, the above-described method or technique is applicable also to a case where two CCDs are used, as in the first and second embodiments. Specifically, the coordinates of the imaging position of the measuring light on the right-hand CCD and the left-hand CCD are used in the address input of the memory. If the coordinates of the imaging position of the measuring light of the right-hand CCD and the imaging position of the measuring light of the left-hand CCD are known, it has been described in Japanese Patent Application No. HEI 1-302486 previously filed by the Applicant of the present invention that the coordinates of the measuring light on the object are uniquely determined or decided with the forward end of the endoscope serving as a reference.

Other arrangement, function and advantages of the present embodiment are similar to those of the fourth embodiment.

An endoscope apparatus for three dimensional measurement according to a ninth embodiment of the invention will next be described.

Figure 13:
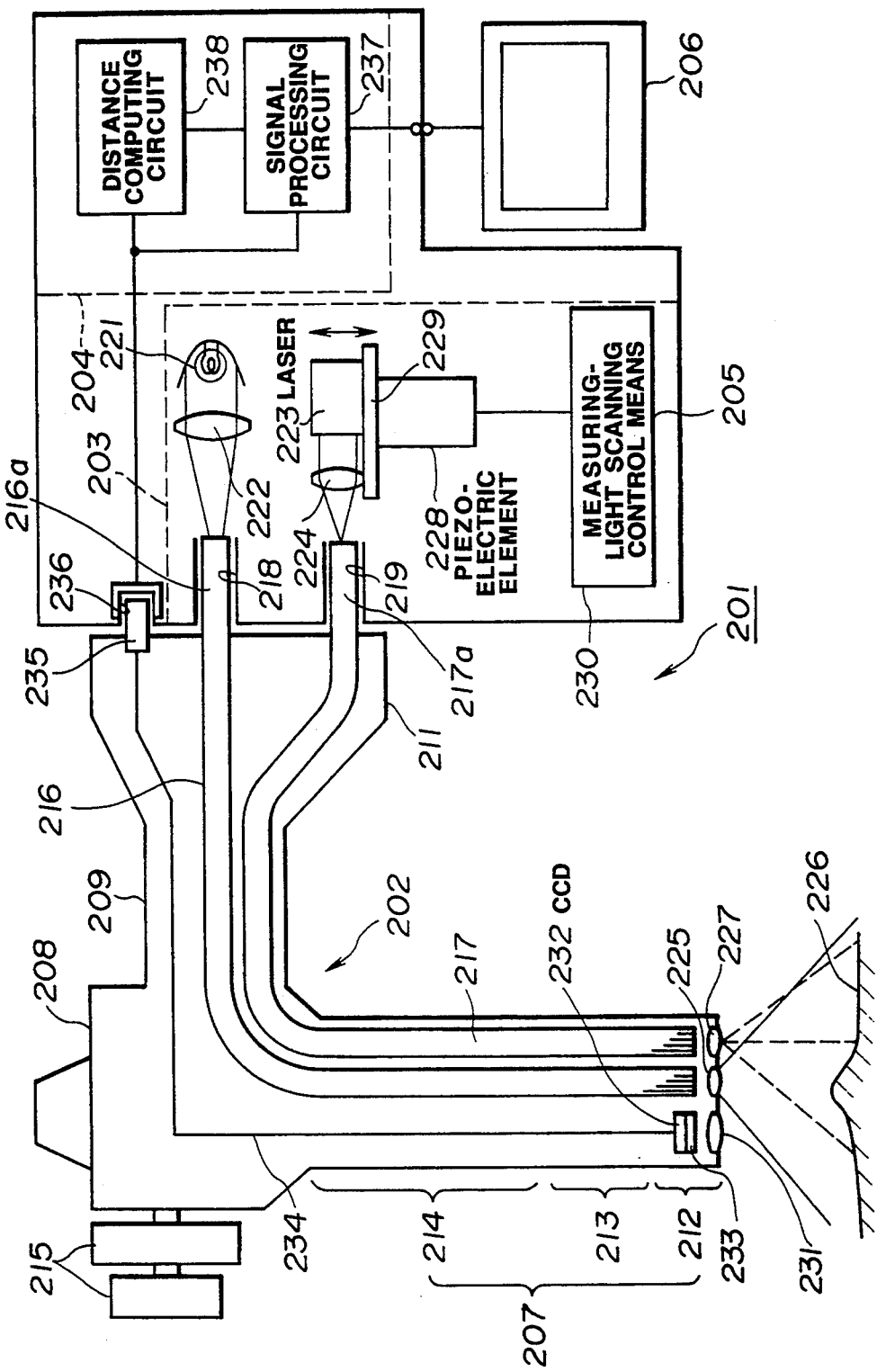

As shown in FIG. 13, the endoscope apparatus 201 for three dimensional measurement, according to the ninth embodiment, comprises an electronic endoscope (hereinafter referred to as an "electronic scope") 202 for three dimensional measurement, which builds therein image pickup means, a light-source processing unit 205 building therein ordinary illuminating light supply means for supplying an ordinary illuminating light to the electronic scope 202, and measuring-light light source means 203 and signal processing means 204 for executing signal processing and distance computation, and a color monitor 206 for displaying a standard image signal which is generated by signal processing due to the signal processing means 204.

The electronic scope 202 has an inserting section 207 which is elongated and which has elasticity so as to be capable of being inserted in a body cavity or the like, an operating section 208 large in width connected to a rearward end of the inserting section 207, and a universal cable 209 extending from a side of the operating section 208. An integrated or overall connector 211 mounted on an end of the universal cable 209 can detachably be connected to the light-source.processing unit 205.

The inserting section 207 has, from a forward end thereof, a hard forward end portion 212, a curving portion 213 capable of being curved, and a flexible tube portion 214 having flexibility. A pair of curving knobs 215 provided on a side surface of the operating portion 208 are operated whereby the curving portion 213 can be curved.

A light guide 216 for transmitting an ordinary illuminating light and an image guide serving as measuring-light transmitting means for transmitting a measuring light are inserted into the inserting portion 207. The light guide 216 and the image guide 217 are inserted also into the universal cable 209. A light guide connector 216a and an image guide connector 217a at respective ends are fixed integrally by the overall connector 211.

The light-source.processing unit 205 is provided with a light guide connector receptor 218 and an image guide connector receptor 219 respectively capable of detachably connecting the light guide connector 216a and the image guide connector 217a. A lamp 221 and a condenser lens 222 for generating a white light are arranged in rear of the light guide connector receptor 218 within the light-source.processing unit 205, so that a white illuminating light from the lamp 221 can be condensed by the condenser lens 222 so as to be supplied to the light guide connector 216a.

Furthermore, a semiconductor laser 223 for generating a laser light and a condenser lens 224 are arranged in rear of the image guide connector receptor 219. A laser light capable of being condensed, from to the semiconductor laser 223, that is, a measuring light is condensed by the condenser lens 224. A measuring light executing scanning linearly as shown, for example, in FIG. 15(a) is irradiated to an end surface of the fiber bundle which forms the image guide connector 217a.

The illuminating light supplied to the light guide connector 216a is transmitted through the light guide 216, is emanated toward a subject 226 further through an illuminating lens 225 from an end surface fixed to the forward end portion 212 adjacent to the outgoing side, and is illuminated toward the subject 226 in a wide area manner. The illuminating lens 225 is mounted at a distance different from a focal distance of the illuminating lens 225 from the end surface of the light guide 216 adjacent to the outgoing side thereof, so that an arrangement of the fibers at the end surface of the light guide 216 adjacent to the outgoing side thereof is not projected to a surface of the subject 226.

Moreover, the measuring light irradiated to the image guide connector 217a is transmitted through the fiber to which the measuring light is irradiated in the image guide 217, is emanated toward the subject 226 further through a projecting (light projecting) lens 227 from the end surface adjacent to the outgoing side fixed to the forward end portion 212, and forms a minute light spot on the surface of the subject 226. The projecting lens 227 is mounted at a focal distance of the projecting lens 227 from the end surface of the image guide 217 adjacent to the outgoing side. The measuring light emanating from the fiber at the end surface adjacent to the outgoing side can form a minute light spot on the surface of the subject 226 without being almost or substantially extended or spread.

The semiconductor laser 223 and the condenser lens 224 are mounted on a table 229 which is driven in a vibratory or oscillatory manner by a piezo-electric element 228. A drive signal is applied from measuring-light scanning control means 230 to the piezo-electric element 228, whereby the piezo-electric element 228 is moved in vibration or oscillation in a vertical direction as indicated by an arrow in FIG. 13, for example. By the vertical vibratory movement, the semiconductor laser 223 is similarly moved in a vibratory manner. The measuring light is scanned linearly toward the subject 226 through the projecting lens 227.

The piezo-electric element 228 is driven by a drive signal in the form of, for example, a stepwise wave, from the measuring-light scanning control means 230. By this driving, the measuring light irradiated to the fiber bundle of the image guide connector 217a is successively illuminated every fibers spaced at predetermined intervals, and scans a range of substantially a diameter of the fiber bundle stepwise and linearly as illustrated in FIG. 15(a).

The subject 226 illuminated by the illuminating light in a wide area manner is imaged on an image pickup surface of a CCD 232 serving as an image pickup element arranged at a focal surface of an objective lens 231 by the objective lens 231 which is mounted on an observing window in the forward end portion 212.

A mosaic color filter 233, for example, is mounted in front of the image pickup surface, and executes color separation optically. The CCD 232 is connected to a signal connector 235 of the connector 211 through a signal cable 234, and is connected to a signal processing circuit 237 and a distance computing circuit 238 through a signal connector receptor 236 to which the signal connector 235 is connected.

An output signal from the signal processing circuit 237 is outputted to the monitor 206, and is displayed on a screen of the monitor 206. The signal processing circuit 237 executes signal processing which generates a standard image signal from the output signal from the CCD 232. The signal processing circuit 237 masks the circumstance or periphery of the image of the subject 226 by an endoscope display frame data generated by a ROM (not shown) and the like, and outputs the image of the subject 226 toward the monitor 206.

The distance computing circuit 238 executes computation or the like of a distance to a spot position of the measuring light formed on the CCD 232 and the surface of the subject 226, on the basis of the output signal from the CCD 232. Specifically, the distance computing circuit 238 executes spot-position detecting processing obtaining a position (x, y) of the spot on the surface of the CCD 232. The distance computing circuit 238 executes computation using the principle of triangulation by the use of the positional data obtained by this detecting processing and information on distance computation, specifically, information including a focal length f1 of the projecting lens 227 and a focal length f2 of the objective lens 231, a distance d between optical axes thereof, a position g (relative position from the optical axis of the projecting lens 227) of the laser light incident upon the incident end surface of the image guide 217 (data on the position a are supplied from the measuring-light scanning control means 230), and the like, to compute the distance R or the like to the spot position (X, Y, Z) on the surface of the subject 226. The computing data signal is superimposed by a superimpose circuit (not shown) of the signal processing circuit 237, and is outputted toward the monitor 206.

In this embodiment, the objective lens 231 and the projecting lens 227 are arranged at the forward end portion 212 in adjacent relation to each other, as shown in FIG. 14, for example. The illuminating lens 225 is arranged at one side or both sides, as indicated by the dot-and-chain lines, of the objective lens 213 and the projecting lens 227.

Moreover, in this embodiment, as shown in FIG. 13, in a case where the table 229 is vibrated or oscillated vertically, the laser light scans the fiber bundle vertically on the side of the incident end surface of the image guide 217. By the scanning, a condition adjacent to the outgoing end surface corresponds to a condition scanned horizontally in FIG. 13, and the measuring light projected toward the subject 226 through the projecting lens 227 is emanated within a plane m including the optical axis of the objective lens 231 and the optical axis of the projecting lens 227 illustrated in FIG. 14, radially by the projecting lens 227.

As described above, since the table 229 is scanned stepwise, in a case where the measuring light is scanned under a condition, for example, that the surface of the subject 226 is planar, and the end surface of the forward end portion 212 is confronted vertically with the surface, spot lines or rows s spaced substantially as predetermined constant intervals appear on an image-pickup surface of the CCD 232 correspondingly to stepwise scanning, as illustrated in FIG. 15(b). The spacings or intervals between the spot rows s vary depending upon the distance between the forward end surface of the scope 202 and the subject 226, and it is possible to compute an actual spot distance on the basis of the principle of triangulation. The numbers of the spot rows s or the pitch of the stepwise wave is set to a value within a number in which each spot can be recognized in separation from the output signal of the CCD 232, or a value equal to or more than the pitch within a period of time of one (1) filed or one (1) frame.

On the other hand, in a case where the surface of the subject 226 is irregular, the spot rows whose intervals are not uniform appear linearly in accordance with the irregular surface (in a case where scanning is executed in the plane m including the optical axis of the objective lens 231 and the optical axis of the projecting lens 227). Also in this case, it is possible to compute the distance to the spot position where the spot position is actually formed on the surface of the subject 226, from the positional information of each spot on the CCD 232, by the use of the principle of triangulation. The distance computing circuit 238 executes this computation of the distance.

In a case where scanning is executed in a direction other than the plane m, the spot position is scattered about the linear line in accordance with the irregular surface.

Figure 16:
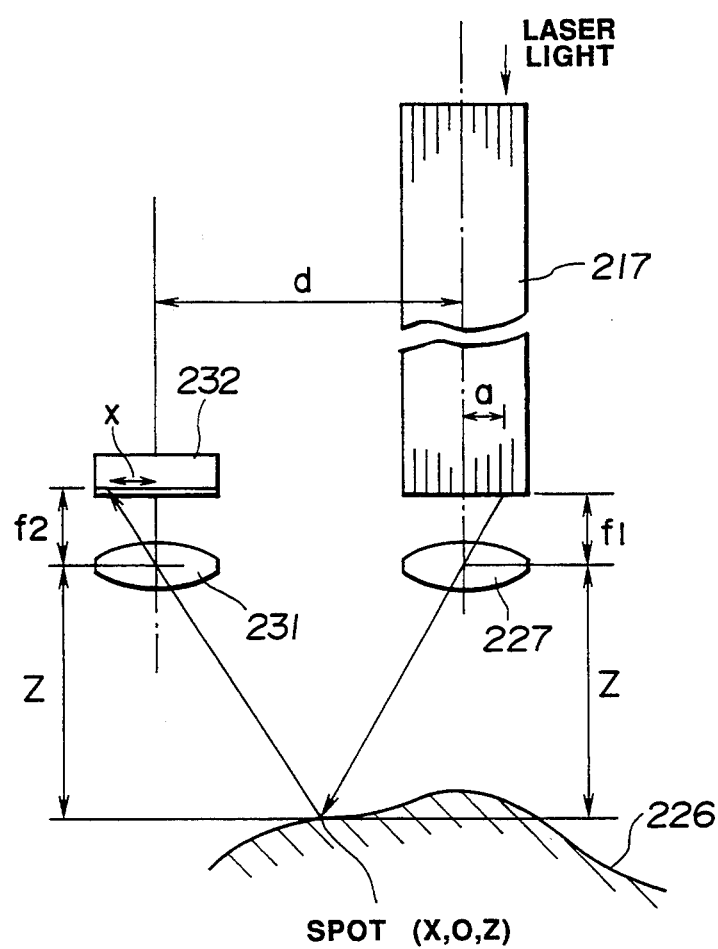

FIG. 16 is a view for explanation, showing the principle on the basis of which the spot position (X, Y, Z) (in this connection, in this figure, in a case of Y=0) is found in a case where scanning is executed in this plane m.

In this FIG. 16, it is assumed that a lateral (horizontal) direction in a sheet surface is an X-axis, an optical-axis direction of the objective lens 231 is a Z-axis, and a vertical direction with respect to the sheet surface is a Y-axis. A laser light incident upon with a distance a from the optical axis of the projecting lens 227 of the laser light which is incident upon the incident end surface of the image guide 217 forms a spot at a position (X, Y, Z) (a position of the objective lens 231 is the origin) on the surface of the subject 226. The spot is imaged on a position (x, y) (in this connection, in a case of y=0 in this figure) of the image pickup surface of the CCD 232 by the objective lens 231, and information on the position (x, y) is detected by a signal processing system of the image forming circuit 238.

Assuming that the focal length f1 of the projecting lens 227 and a distance d between the optical axis of the objective lens 231 and the optical axis of the projecting lens 227 are used, the following equation holds:

$$a:f1 = d - X:Z \quad (1)$$

Further, if attention is paid to an imaging system of the objective lens 213, the following equation holds:

$$x:f2 = X:Z \quad (2)$$

From the equations (1) and (2), the following equation holds:

$$X = f1 \cdot d \cdot x / (f2 \cdot a + f1 \cdot x) \quad (3)$$

The following equation also holds:

$$Z = f2X/x = f1 \cdot f2 \cdot d / (f2 \cdot a + f1 \cdot x) \quad (4)$$

Moreover, the distance R from the objective lens 231 to the spot position can be produced as a square root of the following equation:

$$R \cdot R = (X \cdot X + Z \cdot Z)$$

In a case where Y is not equal to 0, the distance R can also be similarly produced.

In connection with the above, measurement due to the measuring light can be executed more than one during the one field period of time or the one frame period of time. If there is a case where it is impossible to compute the distance because the spot is not formed (or the return light of the spot can be detected) due to the cavity portion or the like, or a case where distance computation cannot be executed because the spot is out of the image pickup range (or a range of field of view) even if the spot is formed on the surface of the subject 226, or in a case where detection cannot be executed because there is almost no difference between a level of the return light of the projected spot and a circumferential or peripheral level, or the like, a signal indicating measurement impossibility or the like is outputted to the signal processing circuit 237 due to the fact that the distance computing circuit 238 cannot detect the spot position. This is displayed on the monitor screen.

The display is executed in a case for example, where detection of the spot position cannot be executed till time set by a timer (not shown). Further, in a case where a plurality of spots are formed during a one field period of time or during a one frame period of time, if the numbers of spots to be detected are different from the numbers of spots to be projected, inconsistency or the like is displayed.

Furthermore, since there is a case where the spots on the surface of the subject 226 are piled up one another in a portion where an amount of irregularity is large, the dimension or magnitude of the pitch of the stepwise wave can be set variably in accordance with a using status. The distance computing circuit 238 separates in color the output signal from the CCD 232, a signal component of the wavelength of the laser light is extracted, for example, an envelope detecting signal or a low-pass signal of the signal component is subtracted from the signal component to detect the spot, and the spot position on the surface of the CCD 232 is found or held.

Furthermore, the distance computing circuit 238 further computes a distance direction component connecting the subject 226 and the forward end surface of the scope 202 to each other, subsequent to the computation of the distance, that is, an amount of irregularity in a height direction of the surface of the subject 226, and outputs the irregularity data signal to the signal processing circuit 237. The signal processing circuit 237 superimposes the irregularity data signal to the image signal representing the endoscope image to output the same to the monitor 206. For example, as shown in FIG. 17, the computed irregularity data are displayed on a portion below an endoscope image display area 206a, over a scanning range h of the measuring spot in the monitor display screen.

According to the present embodiment, the light guide 216 for transmitting the ordinary illuminating light and the connector portion of the image guide 217 for transmitting the measuring light, adjacent to the light source connection are integrated by the overall connector 211, and can be connected to the light-source.processing unit 5 with one touch. Accordingly, distance measurement and the like can be executed by simple operation. Further, according to the present embodiment, the amount of irregularity of an affected part and the like can simply be computed and displayed simply in addition to ordinary endoscope observation. There can be produced effective data in case of a diagnosis. Thus, an accurate diagnosis can be done.

Furthermore, the measuring-light spots have been described in a case where the measuring-light spots are formed along the linear or straight line in FIG. 15 and the like. However, the invention should not be limited to this specific example. For example, the arrangement may be such that the measuring-light spots are so formed as to have two-dimensional extension or spreading, such as a square lattice or the like. Moreover, in a case where the measuring-light spots are formed in a two-dimensional manner, a distance between the measuring-light spots is computed so that the irregular configuration of the surface of the subject can be displayed in a three dimensional manner. In this case, as occasion demands, the arrangement may be such that interpolation is executed to find the irregular configuration other than the measuring point.

An endoscope apparatus for three dimensional measurement according to a tenth embodiment of the invention will next be described.

Figure 18:
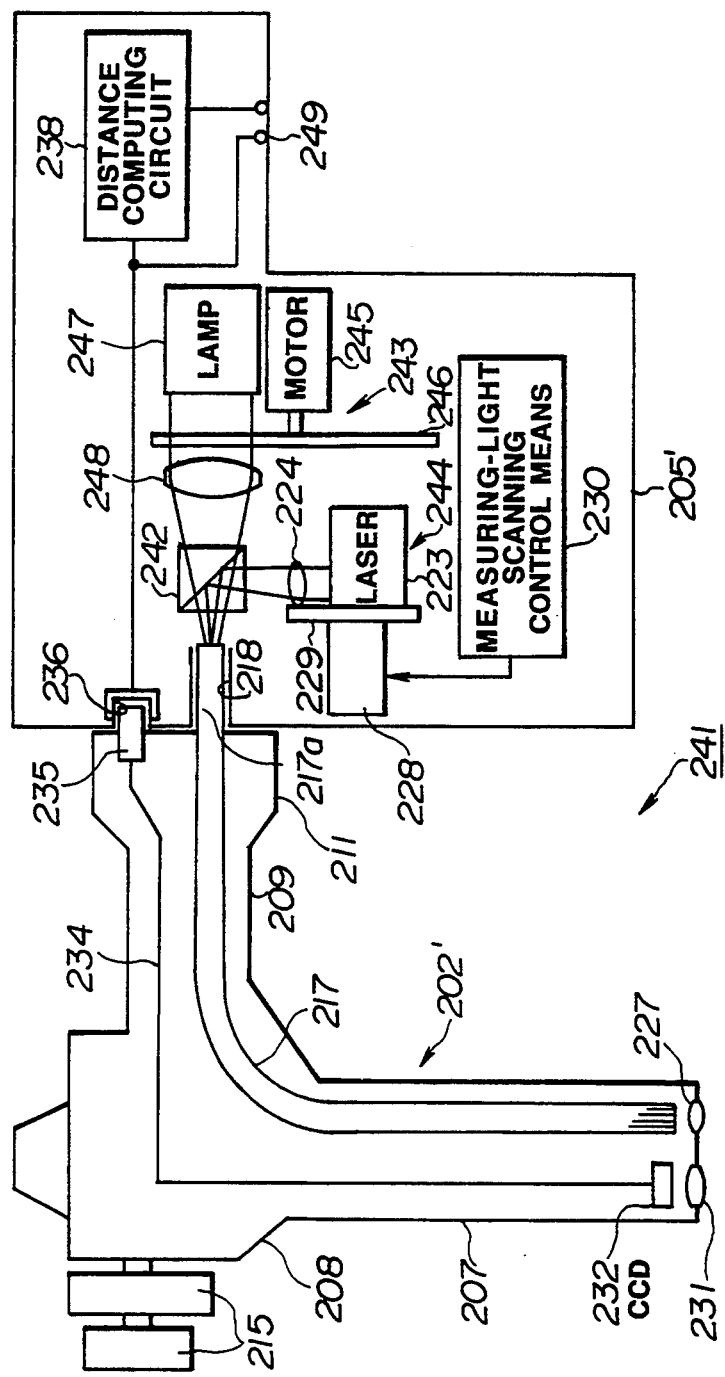
FIG. 18 is a view showing an arrangement of an endoscope apparatus for three dimensional measurement according to a tenth embodiment of the invention.

This embodiment is so arranged as to use both transmitting means for an ordinary illuminating light and transmitting means for a measuring light as single means (accordingly, the embodiment uses a connector as single means). Specifically, as shown in FIG. 18, an endoscope apparatus 241 for three dimensional measurement according to the present embodiment has an electron scope 202' in which an image guide 217 for transmitting an ordinary illuminating light and a measuring light by the use of them as a single light is inserted in an inserting section 207, and the image guide 217 further reaches an image guide connector 217a which is inserted in a universal cable 209 so as to be mounted on an overall connector 211.

The image guide connector 217a can detachably be connected to an image guide connector receptor 218 of a light source unit 205'. A half prism 242 is arranged in opposed relation to the image guide connector receptor 218 within the light source unit 205'. Ordinary illuminating light generating means 243 of surface subsequence is arranged in opposed relation to one of branching surfaces of the half prism 242, and measuring-light generating means 244 is arranged in opposed relation to the other branching surface.

Specifically, a white illuminating light of a lamp 247 is irradiated to, for example, an RGB rotary disc 246 which is rotatively driven by a motor 245 as the ordinary illuminating light generating means 243. An RGB light generated through the RGB rotary disc 246 is condensed by a condenser lens 248, and is incident upon one of the branching surfaces of the half prism 242. The RGB light is transmitted through the half prism 242, and is supplied to the image guide connector 217a.

Moreover, a measuring light from a semiconductor laser 223 is condensed by a condenser lens 224, as the measuring-light generating means 244, similarly to the ninth embodiment. The measuring light is further reflected from the half prism 242, and supplied to the image guide connector 217a. In this connection, since the embodiment uses an illuminating light of surface subsequence, the electronic scope 202' is used which has no mosaic color filter 233.

Furthermore, in the present embodiment, the light source unit 205' is so arranged as to have no signal processing circuit 237, but is so arranged as be connected to an outside signal processing circuit (not shown) by a connector 249. According to the present embodiment, since the electronic scope 202' uses the image guide 217 which transmits the ordinary illuminating light and the measuring light through the inserting section 207 with the use thereof as a unit light, it is possible to reduce a diameter of the electronic scope 202' in addition to the advantages of the ninth embodiment.

An endoscope apparatus for three dimensional measurement, according to an eleventh embodiment of the invention will next be described.

Figure 19:
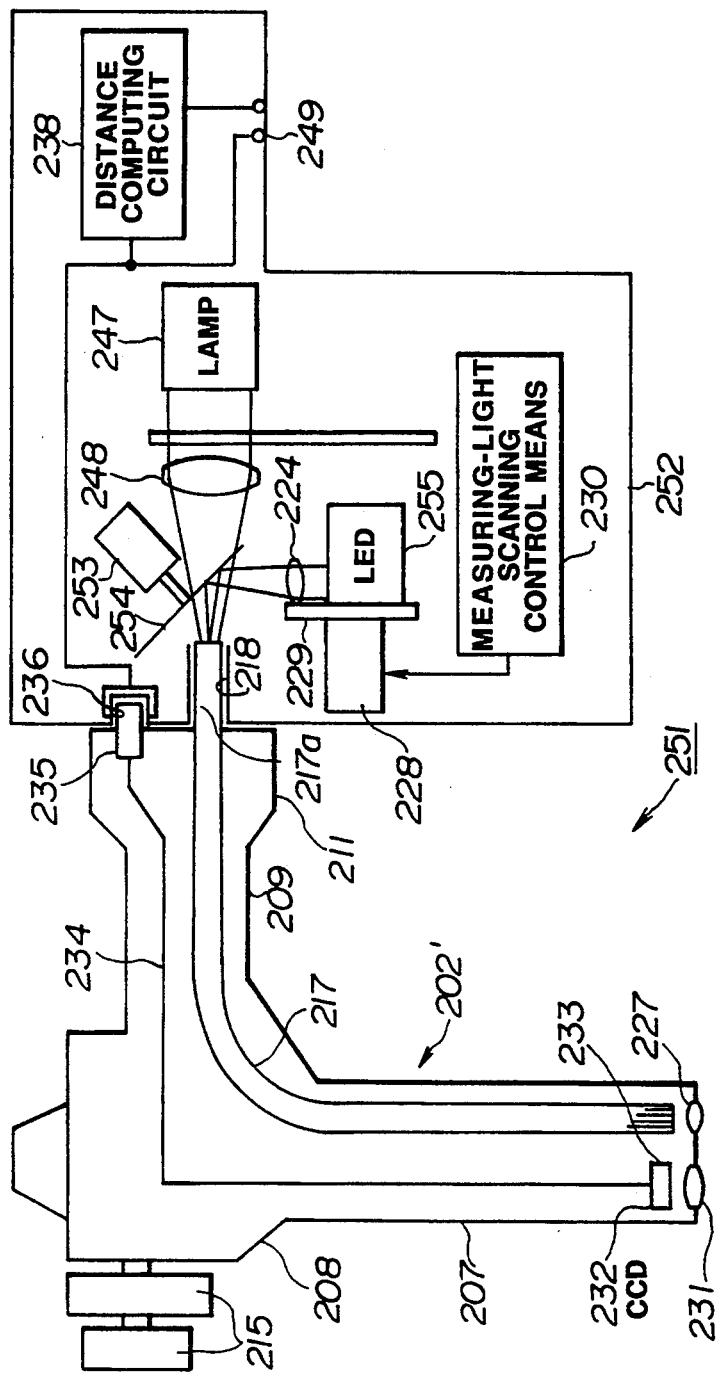

Similarly to the tenth embodiment, the present embodiment has an arrangement in which transmitting means for an ordinary illuminating light and transmitting means for a measuring light are used as a single light. As shown in FIG. 19, an electronic scope 202'' is arranged such that an image guide 217 for transmitting an ordinary illuminating light and a measuring light with the use of them as a single light is inserted in an inserting section 207, similarly to the tenth embodiment. The image guide 217 is further inserted in a universal cable 209, and reaches an image guide connector 217a which is mounted on an overall connector 211.

The image guide connector 217a can detachably be connected to an image guide connector receptor 218 of a light source unit 252. A rotary disc 254 rotatively driven by a motor 253 is arranged with an angle of 45° with respect to an optical path, in opposed relation to the image guide connector receptor 218 within the light source unit 252. As shown in FIG. 20, the rotary disc 254 is provided with a transparent region 254a through which a light is transmitted in a circumferential direction, and a reflecting region 254b from which the light is reflected.

Accordingly, a white light of a lamp 247 arranged in an optical path direction extending along a mounting direction of the image guide connector 217a is condensed by a condenser lens 248, is transmitted through the transparent region 254a of the rotary disc 254, and is supplied to the image guide connector 217a. Moreover, a measuring light of an LED 255 arranged in a direction perpendicular to the optical path is condensed by a condenser lens 224, is reflected in the reflecting region 254b of the rotary disc 254, and is supplied to the image guide connector 217a. In the present embodiment, the ordinary illuminating light is a white light and, accordingly, the electronic scope 202'' has a mosaic color filter 233.

The present embodiment has advantages similar to those of the tenth embodiment. Further, since the rotary disc 254 is used, it is possible to increase a transmission rate at the transmission region 254a and a reflecting rate at the reflecting region 254b more than a transmission rate and a reflecting rate of the half prism 242 so that there can be produced a signal or an image superior in S/N.

An endoscope apparatus for three dimensional measurement, according to a twelfth embodiment of the invention will next be described.

Similarly to the tenth embodiment, the present embodiment is so arranged as to use both transmission means for an ordinary illuminating light and transmission means for a measuring light as single means, and is further provided with means for moving a projecting lens 227, for example, in an optical axis direction to execute focusing/defocusing.

Figure 21:
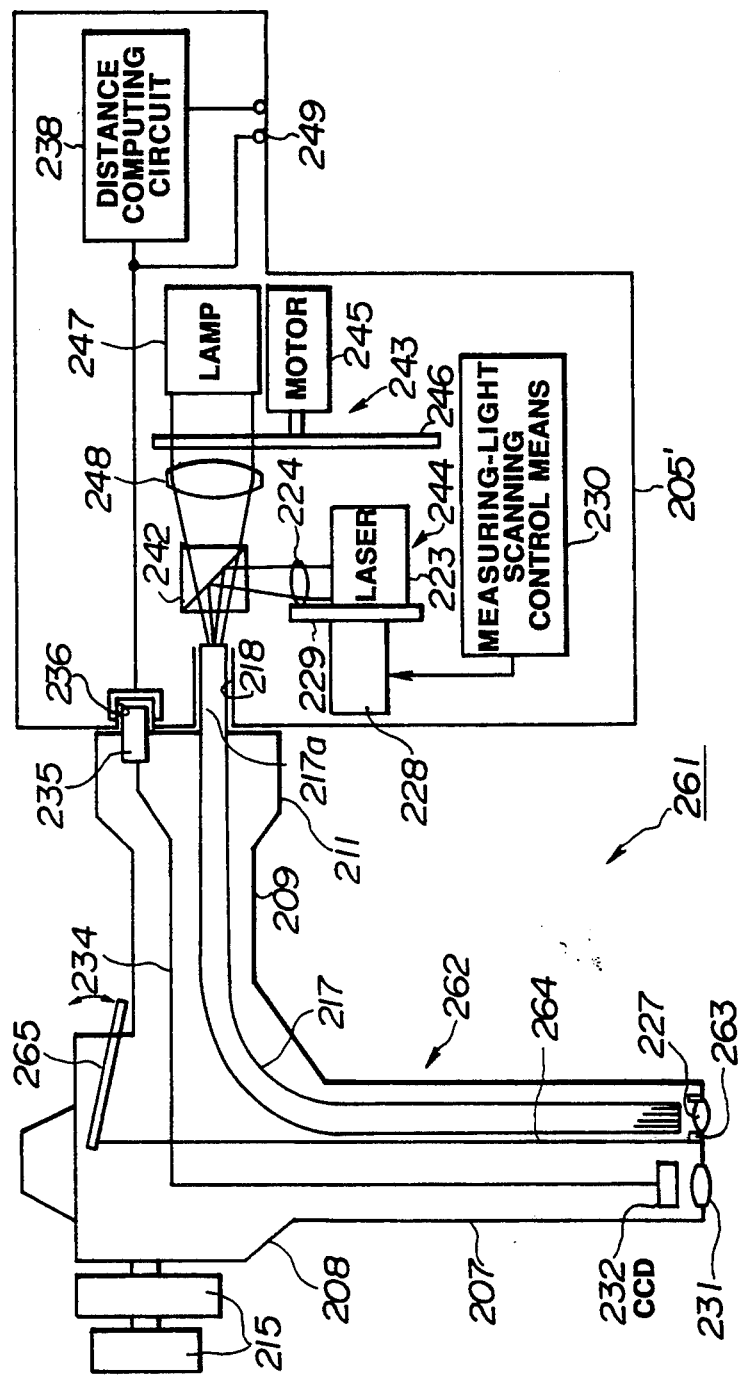

As shown In FIG. 21, an electronic scope 262 of an endoscope apparatus 261 for three dimensional measurement, according to the twelfth embodiment, is arranged such that a wire 264 for executing focusing-/defocusing has one end thereof which is fixedly mounted on a lens frame 263 on which a projecting lens 227 of the electronic scope 202′ in, for example, the tenth embodiment illustrated in FIG. 18 is mounted, the other end of the wire 264 is fixedly mounted on one end of an operating lever 265 which is mounted on an operating section 208, and the other end of the operating lever 265 is rotated or moved angularly as indicated by an arrow whereby the lens frame 263 can be moved in a direction parallel to the optical axis.

Under a condition shown in FIG. 21, a distance of the projecting lens 227 with respect to a forward end surface of an image guide 217 is brought to a defocus position illustrated in FIG. 22(a), closer than the focus position illustrated in FIG. 22(b). Under the defocus condition, in a case where the illuminating light is emanated from the forward end surface of the Image guide 217, illumination can be executed so that the condition of the forward end surface of the image guide 217, that is, a mesh or network configuration of the fiber bundle does not appear adjacent to a subject.

On the other hand, when the operating lever 265 is operated from the condition illustrated in FIG. 21, the projecting lens 227 is moved in the optical-axis direction together with the lens frame 263. The projecting lens 227 as illustrated in FIG. 22(b) can be set to a position spaced a focal distance f apart from the forward end surface of the image guide 217. In a case where the measuring light is projected under this condition, the measuring light emanated from the fibers at the forward end surface of the image guide 217 is not almost spread apart, but is projected onto a surface of the subject, so that a small light spot is formed.

For this reason, it is possible to detect the position of the optical spot with high accuracy, and it is possible to compute irregularities of an affected part or the like with high accuracy. Accordingly, in the present embodiment, in a case where observation is executed due to the ordinary illumination, the operating lever 265 should be set to the condition illustrated in FIG. 21. In a case where distance measurement or the like is executed due to irradiation of the measuring light, the operating lever 265 should be operated from the condition illustrated in FIG. 21 and should be set to the focus condition.

An endoscope apparatus for three dimensional measurement, according to a thirteenth embodiment of the invention, will next be described.

Similarly to the tenth embodiment, the present embodiment is so arranged as to use transmission means for an ordinary illuminating light and transmission means for a measuring light both as single means, and means is further provided for automatically moving, for example, a projecting lens 227 in an optical-axis direction to execute focus/defocus.

Figure 23:
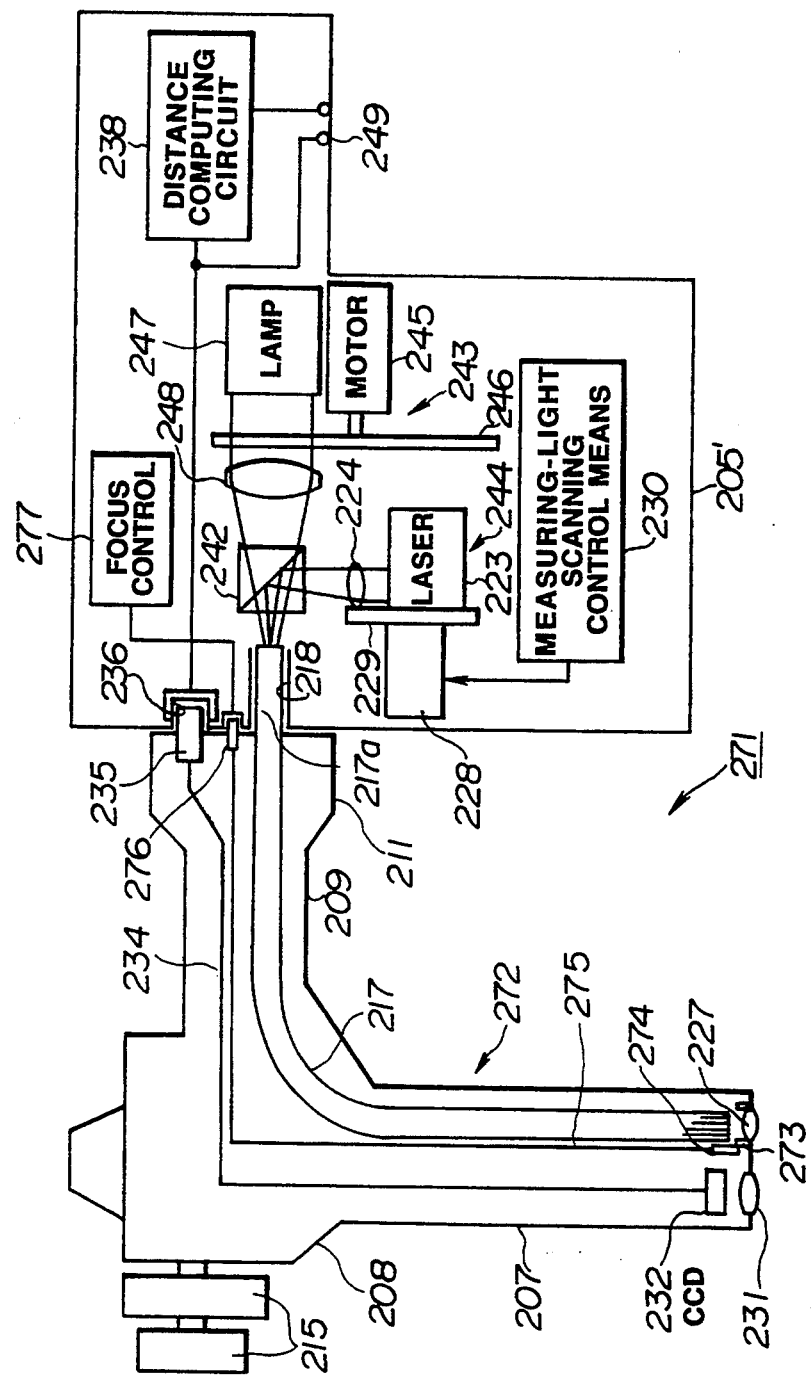

As shown in FIG. 23, an electronic scope 272 of an endoscope apparatus 271 for three dimensional measurement, according to the thirteenth embodiment of the invention, is arranged such that a piezo-electric element 274 for executing focusing/defocusing is mounted on a lens frame 273 on which the projecting lens 227 of the electronic scope 202′ in, for example, the tenth embodiment illustrated in FIG. 18 is mounted. The piezo-electric element 274 is conducted to a contact 276 of an overall connector 211 through a signal line 275. The contact 276 is connected to a focus control circuit 277 through a contact receptor of a light-source unit 205′.

The focus control circuit 277 outputs a drive signal to the piezo-electric element 274 through the signal line 275, whereby the focus control circuit 277 moves the projecting lens 227 to an optical-axis direction together with the lens frame 273. The focus control circuit 277 is set to a focus condition illustrated in FIG. 24(b) from a defocus condition illustrated in FIG. 24(a). Furthermore, the focus control circuit 277 is connected to measuring-light scanning control means 230 through a signal line (not shown). During a period of time the measuring-light scanning control means 230 drives the piezo-electric element 228 to scan the measuring light for executing distance measurement, the focus control circuit 277 outputs a drive signal to the piezo-electric element 274 through the signal line 275, and moves the projecting lens 227 in the optical-axis direction, to set the projecting lens 227 under the focus condition. During a period of time other than the aforesaid period of time, the focus control circuit 277 does not output the drive signal to the piezo-electric element 274 so that the projecting lens 227 is set to the defocus condition.

According to the present embodiment, there is produced a color image less in affection or influence of a network pattern, and distance measurement and the like superior in accuracy can be executed.

An endoscope apparatus for three dimensional measurement, according to a fourteenth embodiment of the invention, will next be described.

The present embodiment is provided with means for automatically moving a projecting lens 227 in an optical-axis direction, similarly to the thirteenth embodiment, to execute focusing/defocusing.

Figure 25:
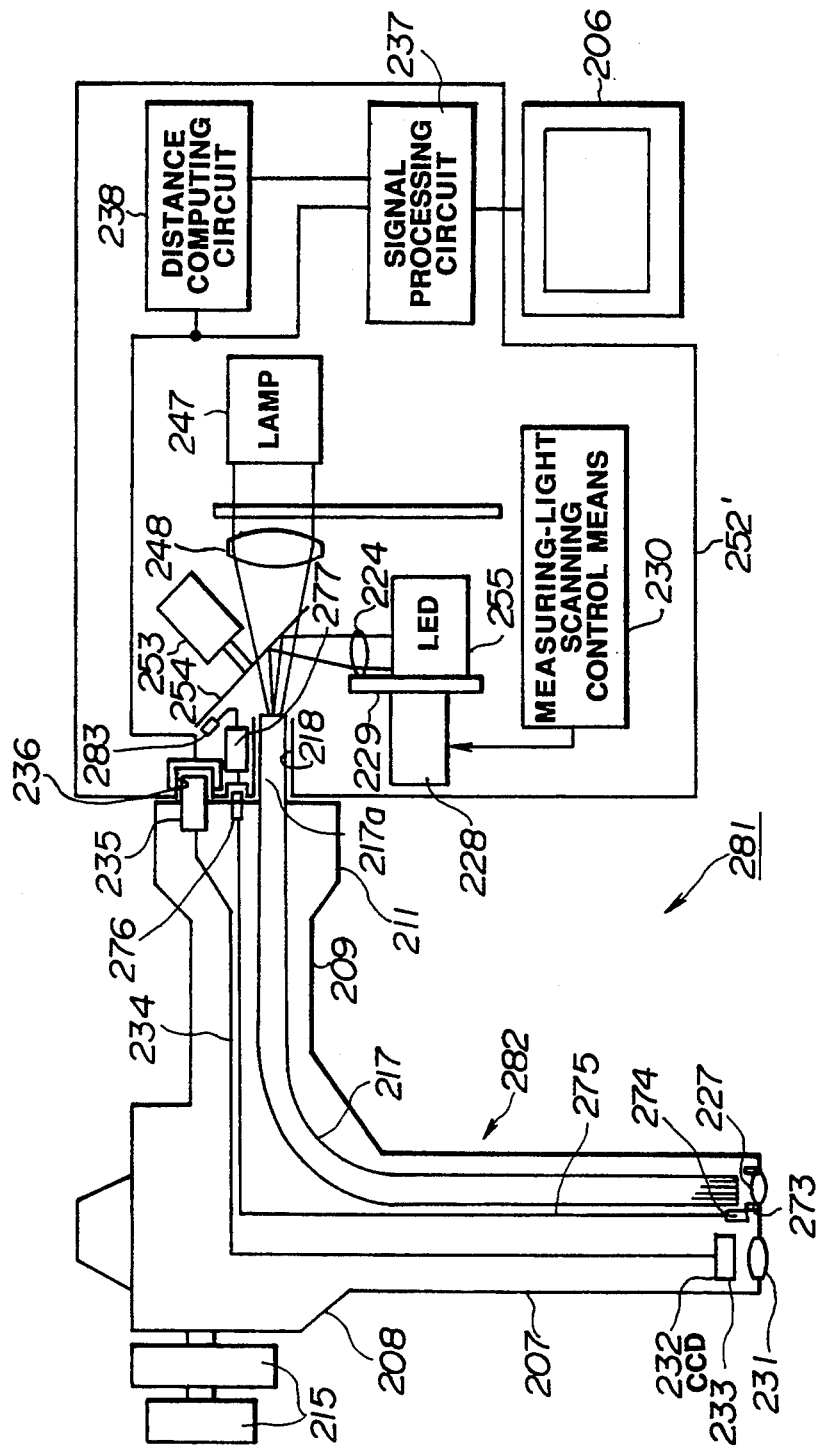
FIG. 25 is a view showing an arrangement of an endoscope apparatus for three dimensional measurement according to a fourteenth embodiment of the invention.

As shown in FIG. 25, an electronic scope 282 of an endoscope apparatus 281 for three dimensional measurement, according to the fourteenth embodiment, is arranged such that a piezo-electric element 274 for executing focusing/defocusing is mounted on a lens frame 273 on which the projecting lens 227 in the electronic scope 202″ in, for example, the eleventh embodiment illustrated in FIG. 19 is mounted, and the piezo-electric element 274 uses an electronic scope 282 which is conducted to a contact 276 of an overall connector 211 through a signal line 275. The contact 276 is connected to a focus control circuit 277 through a contact receptor of a light-source.processing unit 252′. The focus control circuit 277 is connected to a sensor 283 such as a photo-reflector or the like for detecting a rotational position of a rotary disc 254. The focus control circuit 277 outputs a drive signal to the piezo-electric element 274, by the output from the sensor 283.

For example, when the sensor 283 detects timing at which a reflecting region 254b of the rotary disc 254 is located on an optical path, the detecting output is transmitted to the focus control circuit 277. By the output, the focus control circuit 277 outputs the drive signal to the piezo-electric element 274, to set the projecting lens 227 under a focus condition. During a period of time there is no reflecting region 254b of the rotary disc 254 on the optical path, the focus control circuit 277 does not output a drive signal to the piezo-electric element 274, but sets the projecting lens 227 under a defocus condition.

Moreover, in the present embodiment, the detecting output from the sensor 283 is inputted to a distance computing circuit 238 and a signal processing circuit 237 through a signal line (not shown), to control output timing of a CCD drive signal. In the present embodiment, a CCD 232 is an interline transmission type CCD. For example, when the sensor 283 detects the reflecting region 254b, the signal processing circuit 237 outputs a transmission pulse transmitting a signal charge accumulated till time just before the same, to an adjacent vertical transmission line and, subsequently, outputs a CCD drive signal (readout signal). An image signal read out by the drive signal is inputted to the signal processing circuit 237, and is signal-processed so that the image signal is used to execute a color image on a monitor 206.

On the other hand, when a signal representing that the reflecting region 254b is completed is outputted to the signal processing circuit 237 by the sensor 283, the signal processing circuit 237 outputs a transmission pulse similarly to the above and, subsequently, outputs a CCD drive signal (readout signal). An image signal read out by the drive signal is inputted to the distance computing circuit 238, and is used to computation of a distance and computation of an amount of irregularity.

According to the present embodiment, the illuminating period of time due to the ordinary light and the projecting period of time due to the measuring light are executed in time sharing. In synchronism with this time sharing, the illuminating light can be emanated under the defocus condition in the illuminating period of time. On the other hand, during a projecting period of time, the measuring light can be emanated under the focus condition. Further, since the image signals image-picked up during the periods of time are used in separation into the ordinary color display and the distance measurement, there can be produced a color image having no network patterns, which is high in quality, and distance measurement, computation of an amount of irregularity or the like, which are high in accuracy, is made possible.

An endoscope apparatus for three dimensional measurement, according to a fifteenth embodiment of the invention, will next be described.

Figure 26:
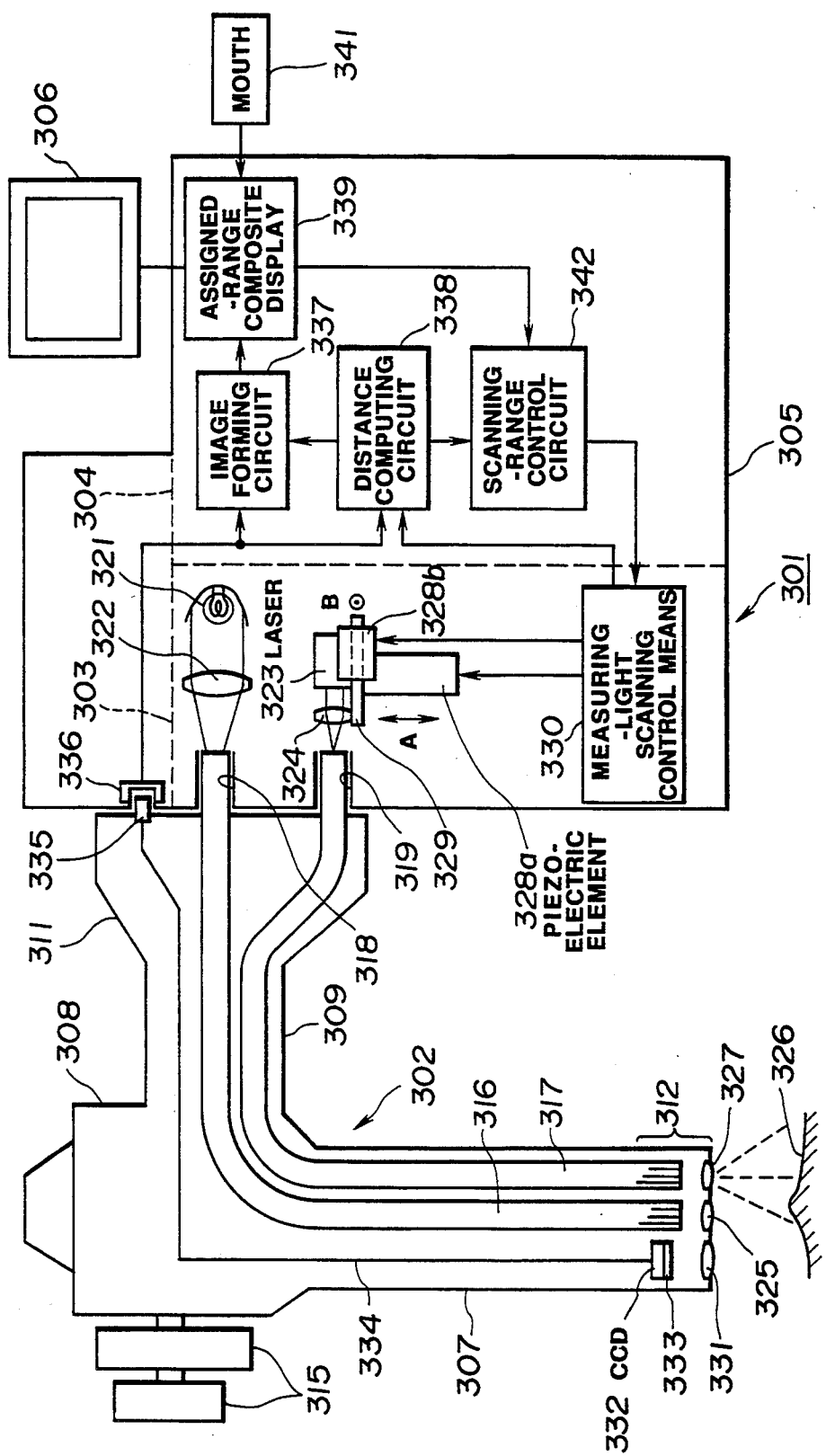
FIGS. 26 through 29 are views showing a fifteenth embodiment of the invention, FIG. 26 being a view showing an arrangement of an endoscope apparatus for three dimensional measurement, FIG. 27 being a view for explanation showing a display example on a monitor screen, FIG. 28 being a view for explanation showing an optical spot observed by a CCD in a case where a laser light is moved stepwise, and FIG. 29 being a front elevational view showing a forward end portion surface of a measuring electronic scope.

As shown in FIG. 26, an endoscope apparatus 301 for three dimensional measurement, according to the fifteenth embodiment of the invention, comprises an electronic scope 302 building therein image pickup means, a light-source.processing unit 305 building therein light source means 303 for supplying an ordinary illuminating light and a measuring light to the electronic scope 302, and signal processing means 304 for executing computation processing and the like of three dimensional information such as signal processing, distance computation and the like, and a monitor 306 serving as image display means for displaying a standard image signal signal-processed and generated by the signal processing means 304.

The electronic scope 302 has an inserting section 307 which is elongated and which has elasticity so as to be inserted in a body cavity or the like, an operating section 308 which is connected to a rearward end of the inserting section 307 and which is wide in width, and a universal cable 309 extending from a side of the operating section 308. An overall connector 311 mounted on an end portion of the universal cable 309 can detachably be connected to the light-source.processing unit 305.

The inserting section 307 has, from a forward end thereof, a hard forward end portion 312, a curving portion capable of being curved, and a flexible tube portion having flexibility. A pair of curving knobs 315 mounted on a side surface of the operating section 308 are operated whereby the curving portion can be curved.

A light guide 316 for transmitting an ordinary illuminating light and an image guide 317 serving as measuring-light transmitting means for transmitting a measuring light are inserted through the inserting section 307. The light guide 316 and the image guide 317 are also inserted through the universal cable 309. A (light guide) connector portion and a (image guide) connector portion at respective ends are fixedly mounted integrally on the overall connector 311.

The light-source.processing unit 305 is provided with a (light guide) connector receptor 318 and a (image guide) connector receptor 319 to which the connector of the light guide 316 and the connector of the image guide 317 can detachably be connected, respectively. A lamp 321 and a condenser lens 322 are arranged on the inside of the light guide connector receptor 318 so that a white illuminating light from the lamp 321 can be condensed by the lens 322 so as to be supplied to the connector of the light guide 316.

Further, a semiconductor laser 323 and a condenser lens 324 are arranged on the inside of the (image guide) connector receptor 319. A laser light capable of being condensed due to the semiconductor laser 323, that is, the measuring light is condensed by the condenser lens 324, and is irradiated to the fiber bundle forming the connector of the image guide 317, as a measuring light.

The illuminating light supplied to the connector of the light guide 316 is transmitted by the light guide 316, further passes through an illuminating lens 325 from the end surface fixed to the forward end portion 312 adjacent to the outgoing side, and is emanated toward a subject 326, thereby illuminating, in a wise area, the side of the subject 326. The illuminating lens 325 is mounted on a distance different from a focal distance of the illuminating lens 325 from the end surface of the light guide 316 adjacent to the outgoing side so that an arrangement of the fibers at the end surface of the light guide 316 adjacent to the outgoing side is not projected onto a surface of the subject 326.

Furthermore, the measuring light irradiated to the connector of the image guide 317 is transmitted by the fibers to which the measuring light in the image guide 317 is irradiated. The measuring light further passes through a projecting (light projecting) lens 327 from the end surface fixed at the forward end portion 312, and is emanated toward the subject 326, thereby forming a minute optical spot on the surface of the subject 326. The projecting lens 327 is mounted on a distance coincident with the focal distance of the projecting lens 327 from the end surface of the image guide 317 adjacent to the outgoing side. The measuring light emanated from the fibers at the end surface of the image guide 317 adjacent to the outgoing side can form a minute optical spot on the surface of the subject 326, without extension or spreading of the measuring light.

The semiconductor laser 323 and the condenser lens 324 are mounted on a table 329 which is driven in a vibratory or oscillatory manner by, for example, a pair of piezo-electric elements 328a and 328b. A drive signal is applied to the piezo-electric elements 328a and 328b from measuring-light scanning control means 330, whereby, in FIG. 26, the piezo-electric element 328a is vibrated in an up-and-down direction as indicated by, for example, an arrow A, while the piezo-electric element 328b is vibrated in a direction B normal to or perpendicular to the sheet surface of FIG. 26. By the vibration in the up-and-down direction and/or vertical direction, the semiconductor laser 323 is similarly vibrated. Thus, it is possible to scan the measuring light toward the subject 326 through the projecting lens 327 in an optional direction, such as a linear manner and the like, and it is also possible to scan the measuring light in a two dimensional manner. For example, after having been vibrated linearly by the piezo-electric element 328a, the piezo-electric element 328a is shifted by a minute amount in a direction perpendicular to the straight line by the piezo-electric element 328b, and the piezo-electric element 328b is again vibrated linearly by the piezo-electric element 328a. Such scanning is repeated whereby the measuring light can be scanned in a two dimensional manner.

Figures 28A, 28B:
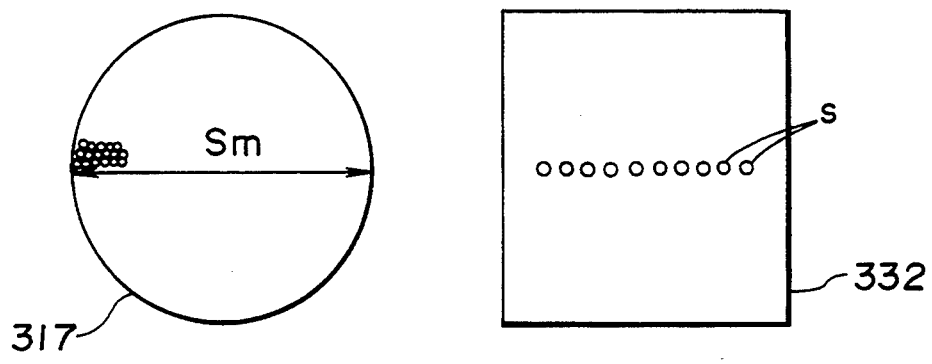

The piezo-electric elements 328a and 328b can be driven by a drive signal of a stepwise wave from the measuring-light scanning control means 330. By this driving, the measuring light irradiated to the end surface of the fiber bundle of the connector of the image guide 317 are successively irradiated every fibers spaced from each other through predetermined intervals in the scanning direction. In this case, a maximum scanning range Sm is a range of substantially a diameter of the fiber bundle which forms the image guide 317, as shown in FIG. 28(a).

The subject 326 illuminated in a wide area manner by the illuminating light is imaged onto an image pickup surface of a CCD 332 serving as an image pickup element arranged at a focal surface of the objective lens 331, by an objective lens 331 which is mounted on an observing window in the forward end portion 312. For example, a mosaic color filter 333 is mounted in front of the image pickup surface, and executes color separation optically. The CCD 332 is connected to a signal connector 335 of the connector 311 through a signal cable 334, and is connected to an image forming circuit 337 for executing signal processing of image formation through a signal connector receptor 336 to which the signal connector 335 is connected, and to a distance computing circuit 338 for executing distance computation and the like.

The output signal from the image forming circuit 337 is displayed on a screen of the monitor 306 through an assigned-range composite display circuit 339. The image forming circuit 337 executes signal processing generating a standard image signal from the output signal from the CCD 332. The image forming circuit 337 masks the circumference or periphery of the image of the subject 326 by endoscope display-frame data generated by a ROM (not shown) and the like, and outputs the image of the subject 326 toward the monitor 306. The distance computing circuit 338 executes computation and the like of a distance to the spot position of the measuring light formed on the CCD 332 and the surface of the subject 326, on the basis of the output signal from the CCD 332.

Specifically, spot-position detecting processing is executed which finds the position (x, y) of the spot on the surface of the CCD 332. The position data found by this detecting processing and information for computing the distance, that is, information including a focal length f1 of the projecting lens 327 and a focal length f2 of the objective lens 332, a distance d between the optical axes thereof, a position (a relative position from the optical axis of the projecting lens 327) (data of the position a are supplied from the measuring-light scanning control means 330) of the laser light incident upon the incident end surface of the image guide 317, and the like are used to execute computation which uses the principle of triangulation, to compute a distance R to the spot position (X, Y, Z) on the surface of the subject 326, and the like. The computed data signal is superimposed by a superimpose circuit (not shown) of the image forming circuit 337, and is outputted toward the monitor 306.

Figure 27:
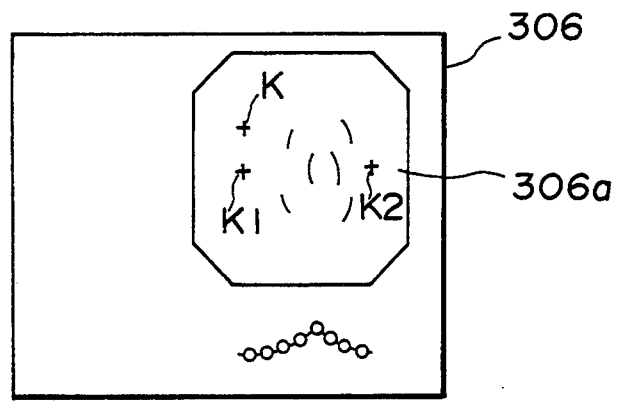

An output signal from a mouse 341 for assigning a scanning range is also inputted to the assigning-range composite display circuit 339. The assigning-range composite display circuit 339 generates a cursor display signal, and superimposes the cursor display signal on an image signal corresponding to an endoscope image from the image forming circuit 337, to output the cursor display signal to the monitor 306. Accordingly, the cursor display signal is displayed as a cursor K as indicated in FIG. 27, which is moved on the monitor screen in accordance with operation of the mouse 341.

The mouse 341 is operated whereby the cursor K for assigning the scanning range is moved on the monitor screen. A click button is operated whereby one end of the scanning range is assigned. The cursor K is further moved. The click button is again operated whereby it is possible to assign the other end. By this double assignment, a scanning range in a case, for example, where a linear scanning range is selected, is determined. In FIG. 27, K1 and K2 denote an example of the scanning range assigned by operation due to the mouse 341.

When each assigning signal is generated due to operation of the click button, the assigning-range composite display circuit 339 outputs positional information of each cursor on the assigned monitor screen to a scanning-range control circuit 342.

Distance information from the distance computing circuit 338 is also inputted to the scanning-range control circuit 342. The scanning-range control circuit 342 uses these information to output, to the measuring-light scanning control means 330, a control information signal regarding the fact that the semiconductor laser 323 is in coincident with the scanning range assigned on the monitor screen if in what direction and in how much the semiconductor laser 323 is moved (scanned).

The measuring-light scanning control means 330 outputs drive signals to the piezo-electric elements 328a and 328b correspondingly to the input control information signal, and scans the optical spot projected on the surface of the subject 326 only through a scanning range corresponding to the scanning range on the monitor screen assigned by the mouse 341.

Figure 29:
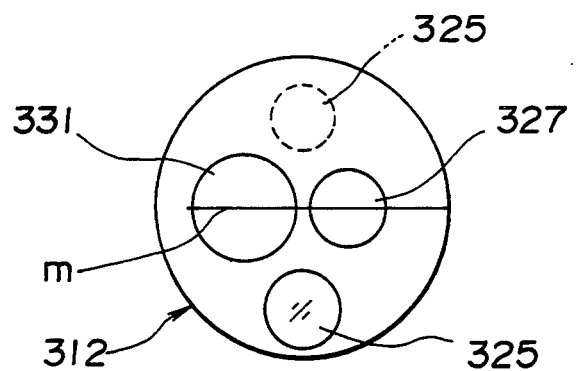

In the present embodiment, the objective lens 331 and the projecting lens 327 are mounted on the forward end portion 312 in adjacent relation to each other as illustrated in FIG. 29, and the illuminating lens 325 is arranged on one side of the objective lens 331 and the projecting lens 327, or on both sides of the objective lens 331 and the projecting lens 327, as indicated by a dot-and-dash line.

Moreover, in the present embodiment, as shown in FIG. 26, in a case where the table 329 is vibrated in a vertical direction, the laser light scans the fiber bundle in the vertical direction A on the side of the incident end surface of the image guide 317. By the scanning, the laser light corresponds to a condition in which scanning is executed in a horizontal direction in FIG. 26, on the side of the outgoing end surface. The measuring light projected toward the subject 326 through the projecting lens 327 is emanated radially from the projecting lens 327 in the horizontal direction, within a plane m including the optical axis of the objective lens 331 the optical axis of the projecting lens 327, as illustrated in FIG. 29.

Further, the table 329 is so arranged as to be vibrated in a stepwise manner, and a pitch of the step can selectively be set by selective operation of, for example, the mouse 341, and the like. If the pitch decreases, the numbers of spots per unit length in the scanning direction increase. Thus, there are many measuring points, and it is possible to execute measurement in detail. On the other hand, if the pitch is set large, there can be produced measuring results over the entire scanning range at a short period of time. In a case where measurement is executed, the pitch can selectively be set.

In a case, for example, where the surface of the subject 326 is planar, and the piezo-electric element 328a is vibrated in a stepwise manner under a condition that an end surface of the forward end portion 312 is vertically confronted with the surface to scan the laser light, spot rows s of almost constant or predetermined intervals appear in the image pickup surface of the CCD 332, correspondingly to the stepwise scanning, as illustrated in FIG. 28(b). In a case where the pitch is constant, the intervals of the spot rows s vary depending upon the distance between the forward end portion 312 and the subject 326. Thus, it is possible to compute the distance to each position (on the surface of the subject 326) where each spot is actually formed on the basis of the principle of triangulation (although it has been described that only the piezo-electric element 328a is vibrated in a stepwise manner, if the piezo-electric element 328b is also moved only through a minute amount every only the piezo-electric element 328a is moved linearly and in a stepwise manner, the laser light scans the incident end surface of the image guide 317 in a lattice manner, so that a spot in the form of a lattice is formed on the surface of the subject 326).

On the other hand, in a case where the surface of the subject 326 is irregular, spot rows which are not constant intervals appear linearly in accordance with the irregular surface (in a case where scanning is executed in the plane m including the optical axis of the objective lens 331 and the optical axis of the projecting lens 327). Also in this case, it is possible to compute the distance to the spot position actually formed on the surface of the subject 326, by the use of the principle of triangulation, from position information of each spot on the CCD 332. Thus, the distance computing circuit 338 executes computation of the distance.

The spot position scatters about the straight or linear line in accordance with the irregular surface in a case where scanning is executed in a direction other than the plane m.

The principal on the basis of which the spot position (X, Y, Z) is found in a case where scanning is executed in the plane m is the same as the principle in FIG. 16 of the ninth embodiment and, accordingly, the description thereof will be omitted.

In connection with the above, measurement due to the measuring light can be executed more than once during a period of time of one field or one frame. If there is a case where distance computation cannot be executed because a spot is not formed due to a cavity portion or the like (or a return light of the spot cannot be detected), a case where even if a spot is formed on the surface of the subject 326, distance computation cannot be executed because the spot is out of an image pickup range (or a range of field of view), and a case where detection cannot be executed because the level of the return light of the projected spot is not much different form the surrounding or peripheral level, or the like, the distance computing circuit 338 cannot detect the spot position, and the like. Accordingly, the distance computing circuit 338 outputs a signal representing incapability of measurement or the like to the image forming circuit 337, and displays the effect on the monitor screen.

The display is executed in a case, for example, where detection of the spot position cannot be executed till time set by a timer (not shown). Further, in a case where a plurality of spots is formed during a period of time of one field or one frame, if the number of spots to be detected is different from the number of spots expected to be projected, inconsistency or the like is displayed.

Furthermore, the distance computing circuit 338 computes the distance R, and computes a component substantially in a distance direction connecting the subject 326 and the objective lens 331 of the forward end portion 312 to each other, that is, an amount of irregularity in the vertical direction of the surface of the subject 326 (component in a Z-direction in FIG. 5). An irregularity data signal is outputted to the image forming circuit 387. The image forming circuit 337 superimposes the irregularity data signal on the image signal representing the endoscope image, to output the superimposed signal to the monitor 306 through the assigned-range composite display circuit 389. The image forming circuit 337 displays the computed irregularity data over the scanning range (for example, a range connecting K1 and K2 to each other) of the measuring spot in the monitor display surface, at a portion below an endoscope image display area 306a, as shown in FIG. 27, for example.

According to the present embodiment, the scanning range can be set variably. Accordingly, in accordance with the using state, the scanning range can be set to a scanning range suitable for the states. Thus, it is possible to reduce or eliminate the extra or superfluous time taken for distance measurement (due to the fact that an unnecessary range is scanned in a conventional example), and noticed portion is scanned in detail whereby there can also be produced detailed distance measurement data and the like. Moreover, according to the present embodiment, an amount of irregularity of an affected part or the like can simply be displayed in addition to normal or usual endoscope observation, and it is possible to produce effective data in case of diagnosis. For this reason, precise or accurate diagnosis is apt to be given.

In connection with the above, it has been described that the scanning range has been assigned in the endoscope image. However, the scanning range may be assigned under a condition spaced through a predetermined distance.

An endoscope apparatus for three dimensional measurement, according to a sixteenth embodiment of the invention, will next be described.

Figure 30:
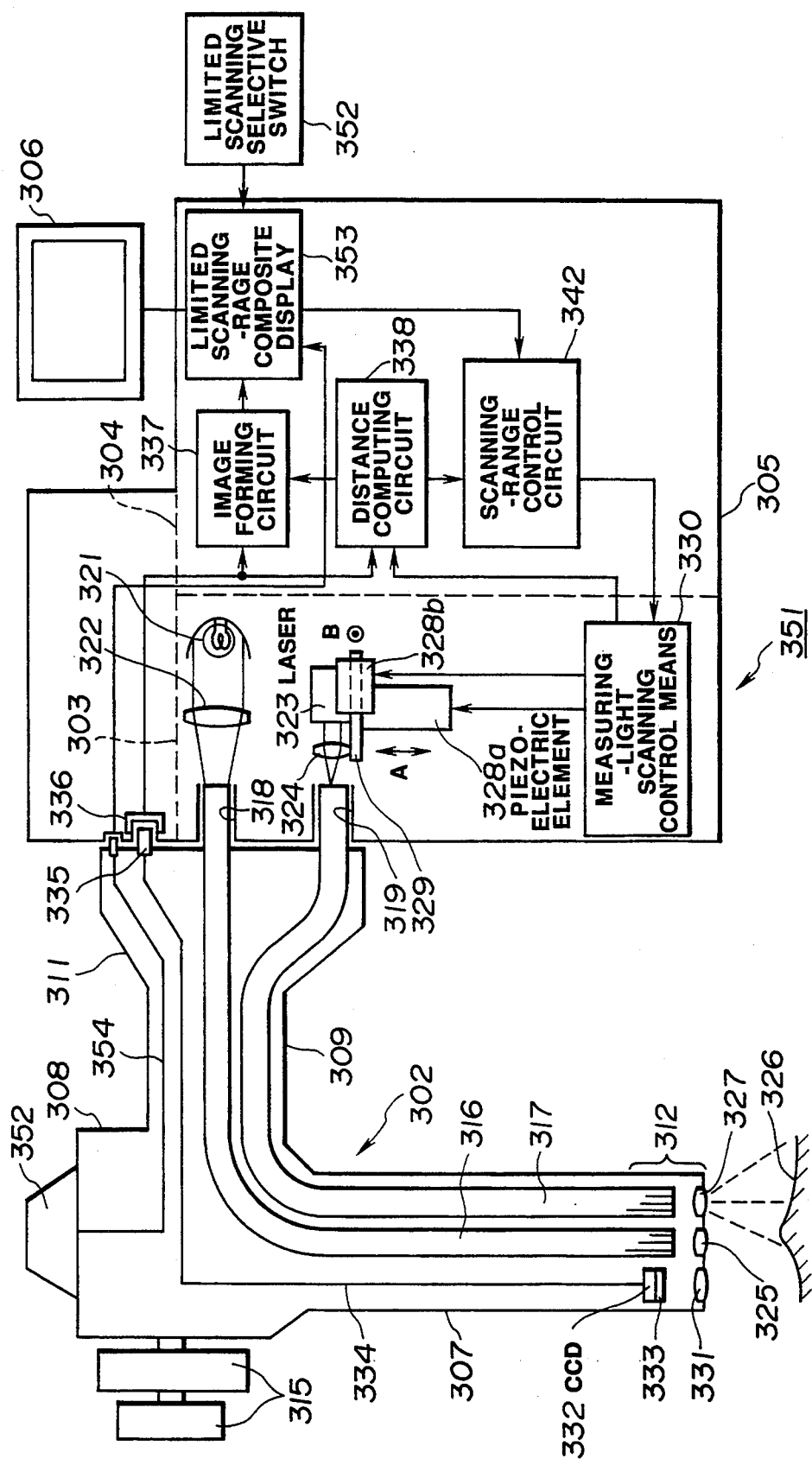
FIG. 30 is a view showing an arrangement of an endoscope apparatus for three dimensional measurement according to a sixteenth embodiment of the invention.

The embodiment is arranged such that a scanning range is restricted (limited) and the like whereby it is made possible to shorten measuring time and to simplify setting of the scanning range, or the like. As shown in FIG. 30, an endoscope apparatus 351 for three dimensional measurement, according to the present embodiment, is provided with a restricted scanning selective switch 352 located on, for example, an operating section 308 of an electronic scope 302, in place of the mouse 341 capable of optically assigning the scanning range in the fifteenth embodiment illustrated in FIG. 26, and is also provided with a restricted scanning-range composite display circuit 353 in place of the assigned range composite display circuit 339. The restricted scanning selective switch 352 is connected to the restricted scanning-range composite display circuit 353 through a signal line 354 (by connection of an overall connector 311).

The restricted scanning-range composite display circuit 353 beforehand registers information corresponding to a plurality of scanning ranges, to a ROM, for example, and can select an optional scanning range from the plurality of scanning ranges, by operation of the restricted scanning selective switch 352. For example, the restricted scanning selective switch 352 has two ON/OFF switches. A selective decision can be executed by one of the two ON/OFF switches, while the subsequent scanning range can be displayed on a monitor 306 by other switch. A desirable scanning range can be displayed on the monitor 306 by operation of the other switch. At this time, if the one switch is operated, the scanning range can be selected.

Other arrangements are similar to that of the fifteenth embodiment.

According to the present embodiment, the scanning range can be selected by simple operation, and the measuring results can be produced for a short period of time. In this connection, a scanning range well used in statistics or the like may be registered, or may be capable of being registered, as the scanning range registered into a ROM or the like.

An endoscope apparatus for three dimensional measurement, according to a seventeenth embodiment of the invention, will next be described.

Figure 31:
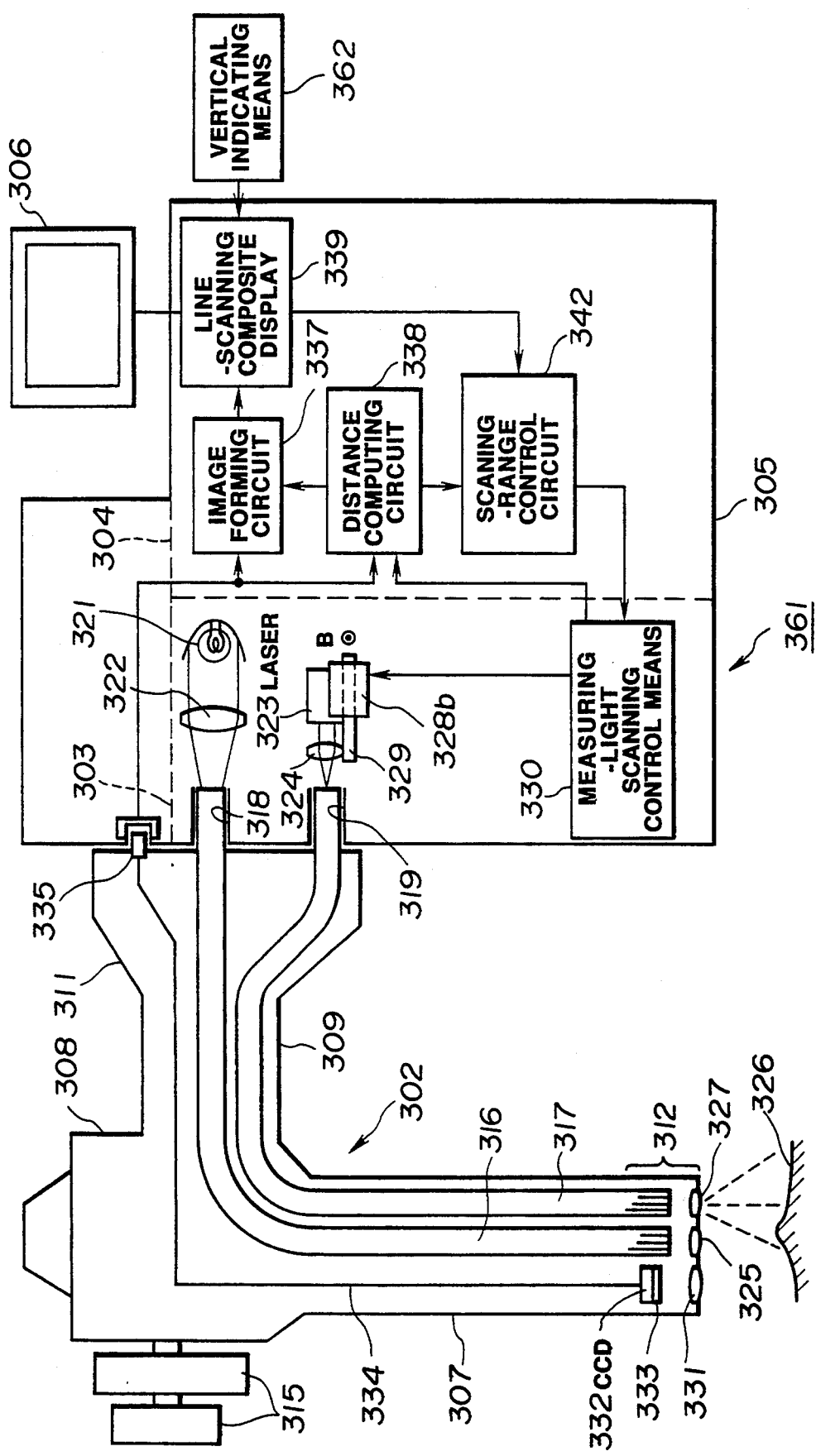
FIGS. 31 and 32 are views showing a seventeenth embodiment of the invention, FIG. 31 being a view showing an arrangement of an endoscope apparatus for three dimensional measurement, and FIG. 32 being a front elevational view showing a forward end portion surface of a measuring electronic scope.

The present embodiment is arranged such that a scanning range executing scanning in a line manner is variable. As shown in FIG. 31, an endoscope apparatus 361 for three dimensional measurement, according to the present embodiment, is provided with vertical indicating means 362, in place of the mouse 341 capable of optionally assigning the scanning range in the fifteenth embodiment illustrated in FIG. 26, is provided with a line-scanning composite display circuit 363 in place of the assigned-range composite display circuit 339, and uses only one piezo-electric element 308b.

Figure 32:
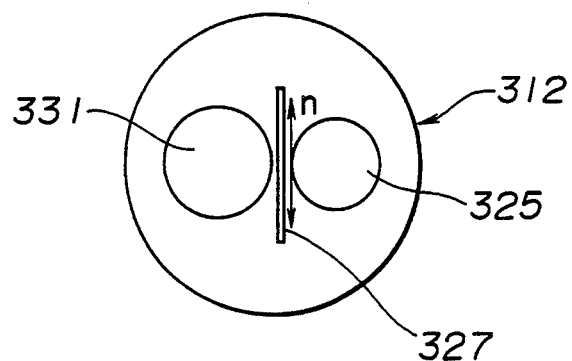

In the present embodiment, a laser light is only moved in a vibratory manner only by one piezo-electric element 308b. Accordingly, the scanning direction of the measuring light emanated to a subject 326 through a projecting lens 327 is brought to a direction perpendicular to the surface m described with reference to FIG. 28, for example. This direction is shown by n in FIG. 32. The vertical indicating means 362 is operated whereby the scanning range in this direction is variable. For example, the vertical indicating means 362 is formed by two switches as is the sixteenth embodiment. These switches are operated whereby the scanning range can be decided variably and selectively.

In the present embodiment, since scanning is executed in the vertical direction in a line manner, an image guide in the form of a thin plate is used as an image guide 317. Further, a projecting lens in the form of a linear or straight line (for example, lenses in which the normal or ordinary lenses are cut down in the form of a line passing through the optical axis of the lenses) is used as the projecting lens 327 arranged in opposed relation to the forward end surface of the image guide 317. For example, an end surface of a forward end portion 312 is brought to one illustrated in FIG. 32.

According to the present embodiment, since the scanning direction is in the form of a line, it is possible to widely set the scanning range in the form of a line (without increasing a diameter of an inserting section) as illustrated in FIG.

32. Conversely, in a case where the wide scanning range is not required, an inserting section 307 can be reduced in diameter.

An endoscope apparatus for three dimensional measurement, according to an eighteenth embodiment of the invention, will next be described.

Figure 33:
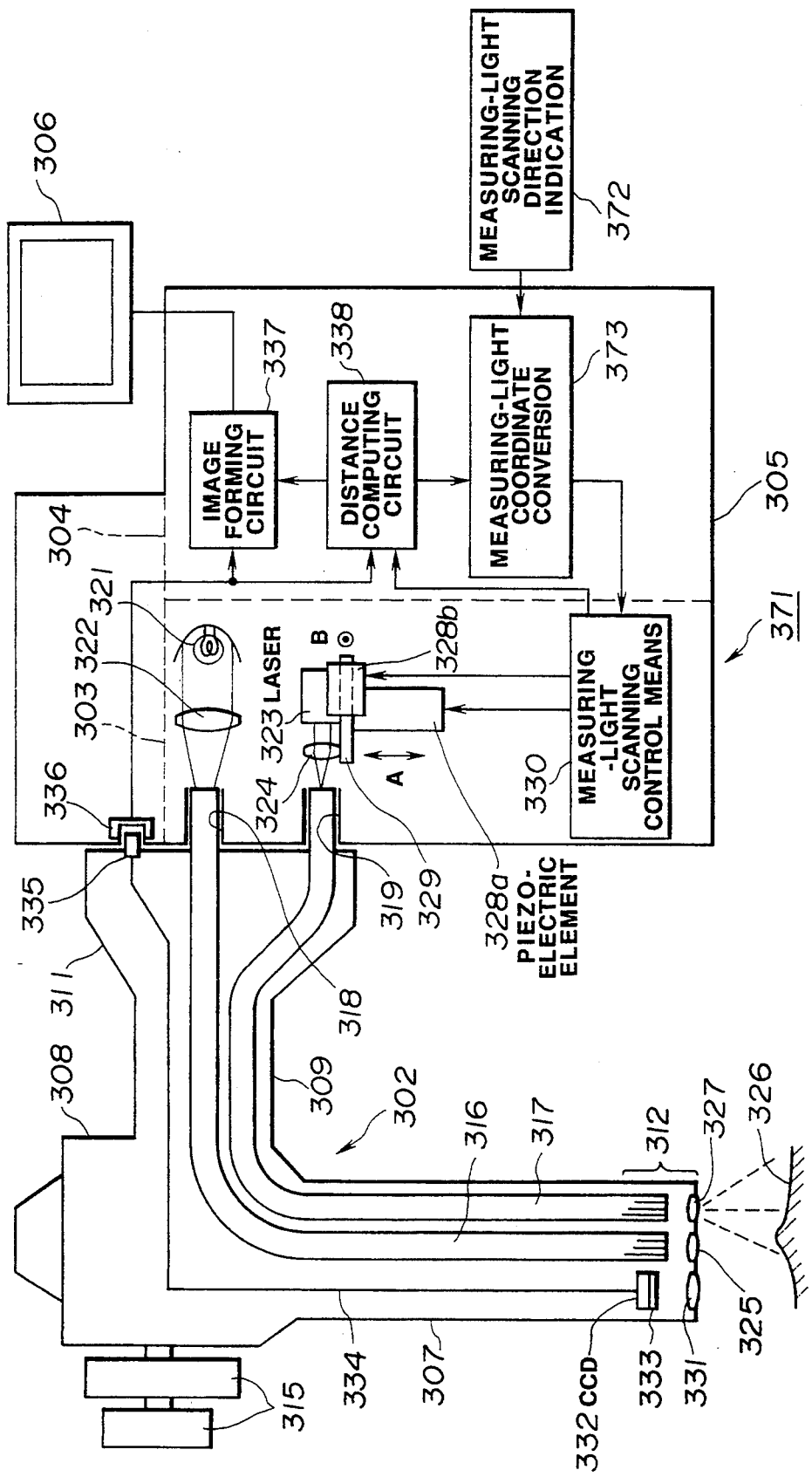
FIG. 33 is a view showing an arrangement of an endoscope apparatus for three dimensional measurement according to an eighteenth embodiment of the invention.

The present embodiment is arranged such that a scanning range can be set such that a measuring light is scanned like a circle, a zigzag form and the like. As shown in FIG. 33, an endoscope apparatus 371 for three dimensional measurement, according to the present embodiment, is provided with measuring-light scanning indicating means 372 for successively indicating a scanning direction of a measuring light, in place of the mouse 341, in the fifteenth embodiment illustrated in FIG. 26. An indicating signal from the measuring-light scanning indicating means 372 is inputted to measuring-light coordinate transformation means 373 which is provided in place of the scanning range control circuit 342. The measuring light is coordinate-transformed. Data concerning which direction the laser light should next be scanned, and how the laser light should be moved in the direction are computed. The computed data are outputted to measuring-light scanning control means 330. The measuring-light scanning control means 330 outputs a drive signal to a pair of the piezo-electric elements 328a and 328b such that a spot is formed in the scanning range indicated by the measuring-light scanning indicating means 372 in accordance with the data outputted from the measuring-light coordinate transformation means 373.

In connection with the above, the arrangement may be such that data on the basis of which scanning such as a circle, a zigzag form or the like can be executed are beforehand registered, and selection is made therefrom so that desirable scanning can be executed.

Further, in the present embodiment, an output signal from the image forming circuit 337 is directly outputted to a monitor 306.

An endoscope apparatus for three dimensional measurement according to a nineteenth embodiment of the invention will next be described.

Figure 34:
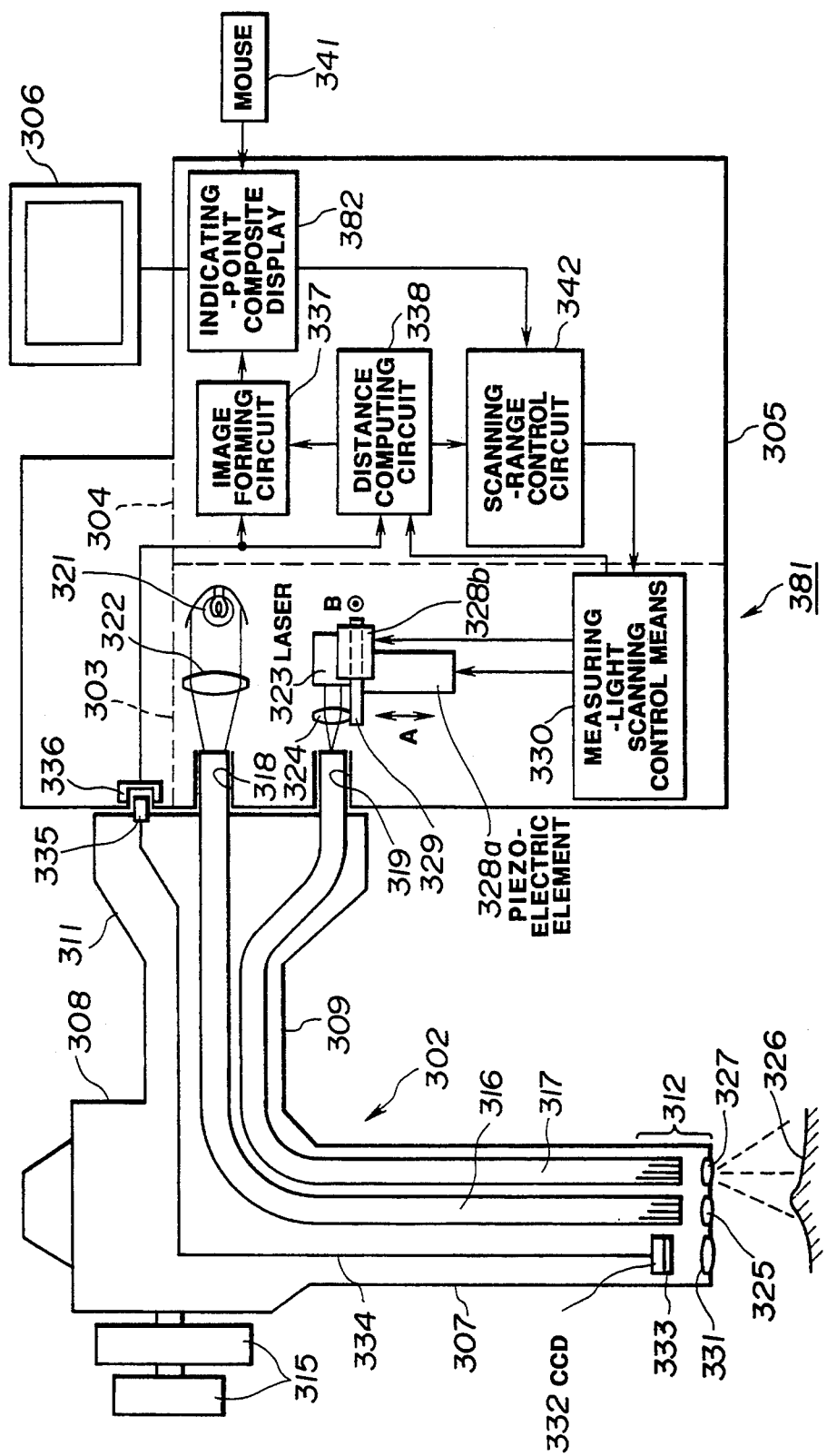

The present embodiment is arranged such that pointing means is provided for executing indication for projecting a spot to a point to which attention is paid, such as an affected part or the like within an endoscope image. As shown in FIG. 34, an endoscope apparatus 381 for three dimensional measurement, according to the present embodiment, is provided with an assigned-point composite display circuit 382 in place of the assigned-region composite display circuit 339 in the fifteenth embodiment illustrated in FIG. 26. By assignment due to a mouse 341, the optical spot is projected to the assigned point.

Figure 35:
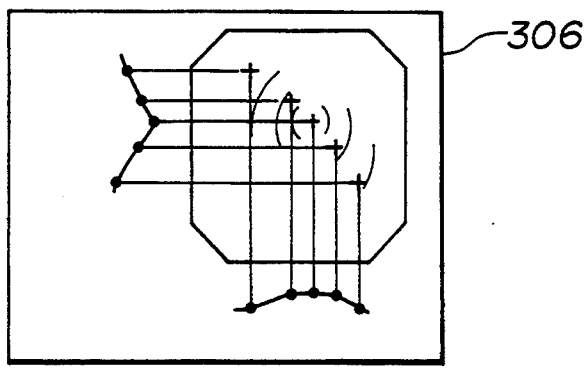
FIGS. 34 and 35 are views showing a nineteenth embodiment of the invention, FIG. 34 being a view of an arrangement of an endoscope apparatus for three dimensional measurement, and FIG. 35 being a view for explanation showing a display example on a monitor screen.

Data at the assigned points are inputted to a scanning-range control circuit 342 through the assigned-point composite display circuit 382. A distance between assigned adjacent indicating points and a direction thereof are computed. Data thereof are outputted to a measuring-light scanning control circuit 330. The measuring-light scanning control circuit 330 outputs a scanning drive signal corresponding to the direction and the distance connecting the points to each other to a pair of piezo-electric elements 328a and 328b such that an optical spot is formed adjacent to each assigned point. A distance computing circuit 338 computes distances at the respective assigned points, and further computes an amount of irregularity so that the distance computing circuit 338 displays the amount of irregularity by components projected longitudinally and laterally on a screen of a monitor 306 as illustrated in FIG. 35, for example. In this connection, in FIG. 35, crosses indicate assigned points, respectively.

According to the present embodiment, it is ensured that it is possible to find the amount of irregularity of a portion actually desired, and the like.

An endoscope apparatus for three dimensional measurement according to a twentieth embodiment of the invention will next be described.

Figure 36:
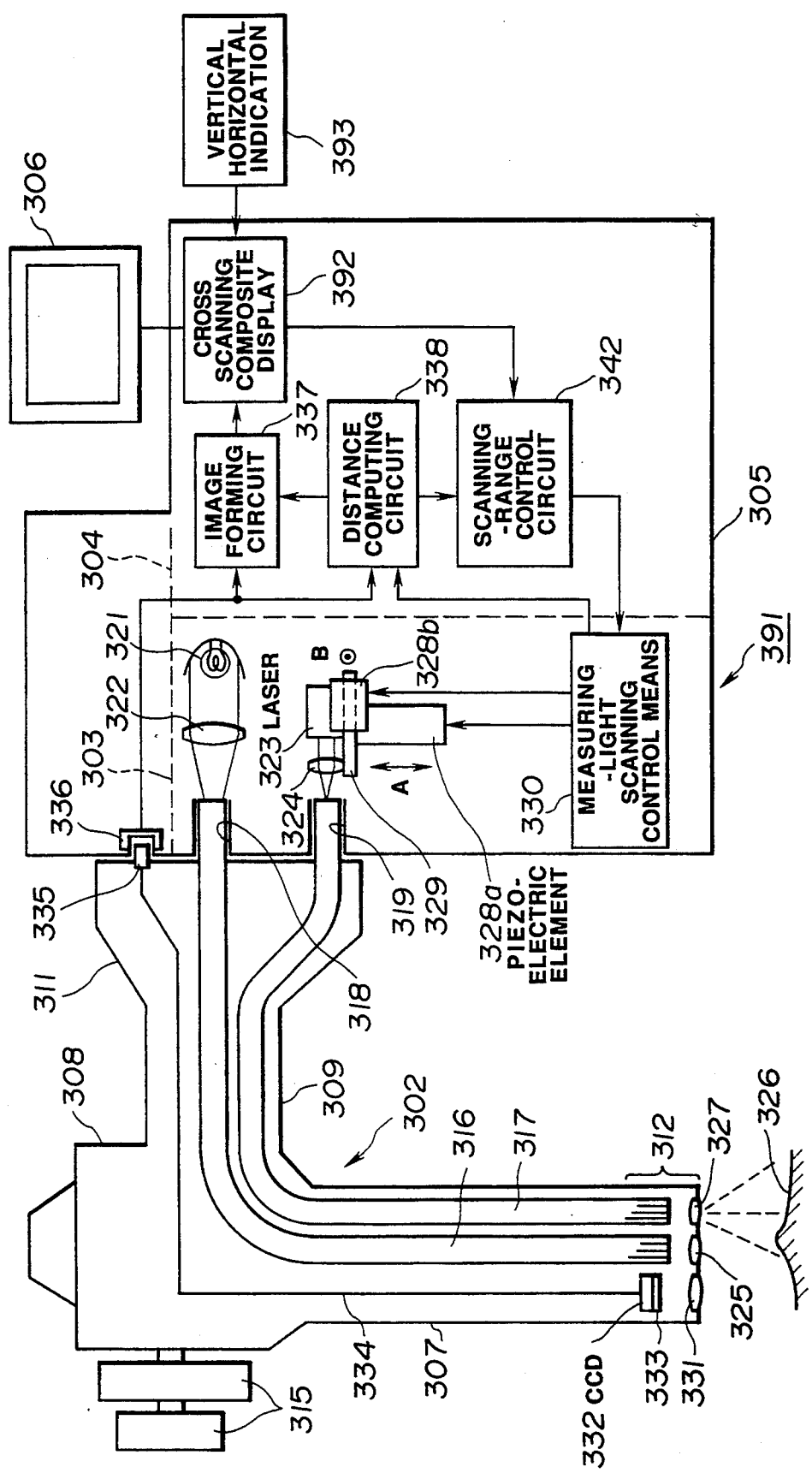
FIG. 36 is a view showing an arrangement of an endoscope apparatus for three dimensional measurement according to a twentieth embodiment of the invention.

The present embodiment is arranged such that scanning is executed vertically and laterally, and a scanning range thereof can be set variably. As shown in FIG. 36, an endoscope apparatus 391 for three dimensional measurement according to the present embodiment is provided with a cross scanning composite display circuit 392 in place of the assigned-range composite display circuit 339 in the fifteenth embodiment illustrated in FIG. 26, and is arranged such that the scanning range in the vertical and lateral directions can be set variably by vertical and lateral indicating means 393 which is provided in place of the mouse 341. The present embodiment can substantially realize a function required for a normal or usual using condition, and setting of the scanning range can be made easy.

An endoscope apparatus for three dimensional measurement according to a twenty-first embodiment of the invention will next be described.

Figure 37:
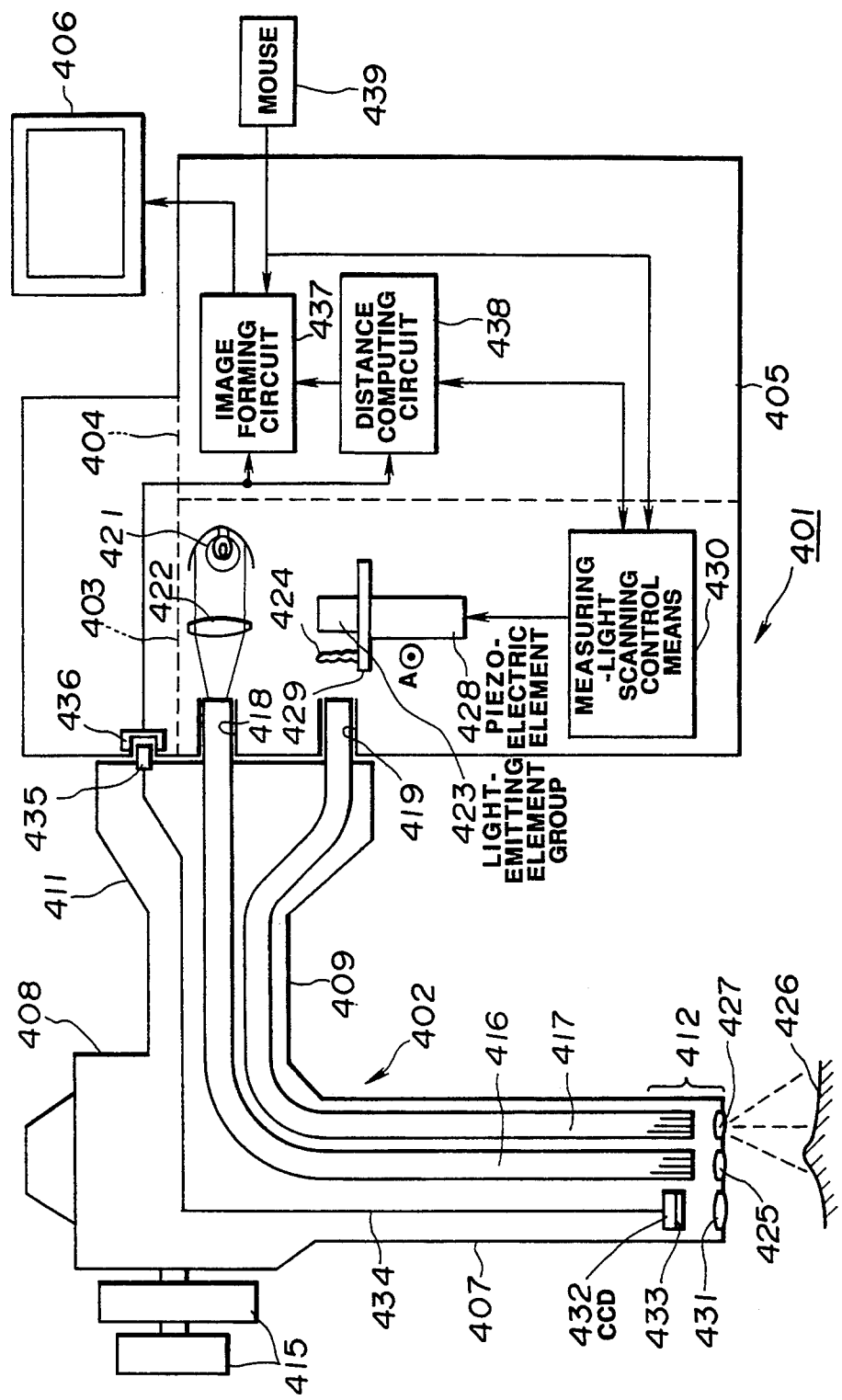
FIGS. 37 through 41 are views showing a twenty-first embodiment of the invention, FIG. 37 being a view showing an arrangement of an endoscope apparatus for three dimensional measurement, FIG. 38 being a perspective view showing a group of light emitting elements and a group of condenser lenses for supplying a measuring light to an incident end surface of an image guide, FIG. 39 being a view for explanation showing a display example on a monitor screen, FIG. 40 being a view for explanation showing an optical spot observed by a CCD in a case where the group of light emitting elements are moved stepwise, and FIG. 41 being a view for explanation diagrammatically showing a locus of scanning of a measuring light.

As shown in FIG. 37, an endoscope apparatus 401 for three dimensional measurement, according to the twenty-first embodiment, comprises an electronic scope 402 building therein image pickup means, a light-source.processing unit 405 building therein light source means 403 for supplying an ordinary illuminating light and a measuring light to the electronic scope 402 and signal processing means 404 for executing computing processing of three dimensional information such as signal processing, distance computation and the like of generation of an image signal, and a monitor 406 serving as image display means for displaying a standard image signal generated in signal processing by the signal processing means 404.

The electronic scope 402 has an inserting section 407 which is elongated and which has elasticity so as to be capable of being inserted into a body cavity or the like, an operating section 408 having great width and which is connected to a rearward end of the inserting section 407, and a universal cable 409 extending from a side of the operating section 408. An overall connector 411 mounted on an end of the universal cable 409 can detachably connected to the light-source.processing unit 405.

The inserting section 407 has, from a forward end thereof, a hard forward end portion 412, a curving portion capable of being curved, and a flexible tube portion having flexibility. A pair of curving knobs 415 mounted on a side surface of the operating section 408 are operated whereby the curving portion can be curved.

A light guide 416 for transmitting an ordinary illuminating light and an image guide 417 serving as measuring-light transmitting means for transmitting a measuring light are inserted in the inserting section 407. The light guide 416 and the image guide 417 are inserted also in the universal cable 409. A (light guide) connector portion and a (image guide) connector portion at respective end portions are fixedly mounted integrally on the overall connector 411.

A (light guide) connector receptor 418 and a (image guide) connector receptor 419 to which a connector of the light guide 416 and a connector of the image guide 417 can detachably be connected, respectively, are provided on the light-source.processing unit 405. A lamp 421 and a condenser lens 422 are arranged on the inside of the light guide connector receptor 418. A white illuminating light of the lamp 421 is condensed by the lens 422, and can be supplied to the connector of the light guide 416.

Figure 38:
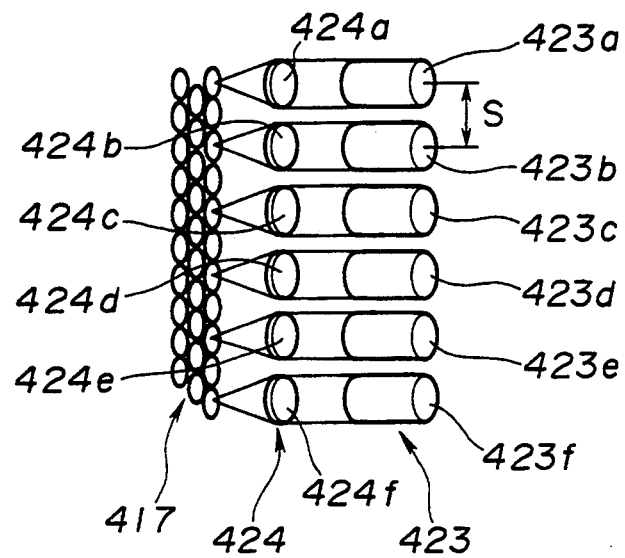

Further, a group of light emitting elements 423 and a group of condenser lenses 424 are arranged on the inside of the (image guide) connector receptor 419. As shown in FIG. 38, lights having respective wavelengths thereof different from each other by light emitting elements 423a~423f forming the group of light emitting elements 423 are condensed respectively by condenser lenses 424a~424f forming the group of condenser lenses 424, and are irradiated to an incident surface in a fiber bundle forming the image guide 417, as a measuring light.

The illuminating light supplied to the connector of the light guide 416 is transmitted by the light guide 416, is further emanated toward a subject 426 from the end surface adjacent to the outgoing side fixed to the forward end portion 412, through an illuminating lens 425, and is illuminated toward a subject 426 in a wide area manner. The illuminating lens 425 is mounted at a distance different from a focus distance of the illuminating lens 425 from the outgoing end surface of the light guide 416. An arrangement of the fibers of the outgoing end surface of the light guide 416 is so arranged as not to be projected onto a surface of the subject 426.

As shown in FIG. 38, the group of light emitting elements 423 includes, for example, six (6) light emitting elements 423a, . . . 423f spaced predetermined intervals s from each other. By these six (6) light emitting elements 423a, . . . 423f, lights are generated which have hues of red, green, blue, yellow, magenta and cyanogen as a measuring light of six (6) colors, for example. As shown in FIG. 38, the lights are condensed by a plurality of condenser lenses 424i, respectively, which are arranged in opposed relation to the light emitting elements 423i (i=a, . . . f). The lights are incident upon the fibers of the incident end surface of the image guide 417 arranged in opposed relation to the condenser lenses 424i, at the predetermined intervals s.

The measuring lights irradiated to the incident end surface of the image guide 417 are transmitted through the fibers to which the measuring light in the image guide 417 is irradiated. The measuring lights are emanated toward the subject 426 from the end surface fixedly mounted on the forward end portion 412, further through the projecting (light projecting) lens 427. The measuring lights form a plurality of minute spot rows simultaneously on the surface of the subject 426. The projecting lens 427 is mounted at a distance in agreement with the focus distance of the projecting lens 427, from the outgoing end surface of the image guide 417. The measuring-light beam rows emanated from the fibers of the outgoing end surface of the image guide 417 are capable of being projected onto the surface of the subject 426 without spreading so that minute spot rows different in color each other are simultaneously formed.

The group of light emitting elements 423 and the group of condenser lenses 424 are mounted on a table 429 driven in a vibratory manner by the piezo-electric element 428, for example. Because a drive signal is applied to the piezo-electric element 428 from measuring-light scanning control means 430, the piezo-electric element 428 is vibrated in a direction perpendicular to the sheet surface as indicated by an arrow A, for example, in FIG. 37 (that is, a direction perpendicular to an arrangement direction of the group of light emitting elements 423 or the group of condenser lenses 424). When the piezo-electric element 428 is vibrated in the vertical direction, the group of light emitting elements 423 is also vibrated, so that the measuring-light rows are scanned in a direction perpendicular to the measuring-light rows, toward the subject 426 through the projecting lens 427.

The piezo-electric element 428 is so arranged as to be capable of being driven by a drive signal in the form of a stepwise wave from the measuring-light scanning control means 430. By this driving, the measuring light irradiated to the end surface of the fiber bundle of the connector of the image guide 417 is successively irradiated every fibers spaced predetermined intervals with the horizontal direction perpendicular to the arrangement direction (in this case, a vertical direction) of the group of light emitting elements 423 in FIG. 38, for example, serving as a scanning direction.

The subject 426 illuminated in a wide area manner by the illuminating light is imaged on an image pickup surface of a CCD 432 serving as an image pickup element arranged on a focus surface of an objective lens 431 by the objective lens 431 mounted on an observing window in the forward end portion 412. For example, a mosaic color filter 433 is mounted in front of the image pickup surface, and optically executes color separation optically. The CCD 432 is connected to a signal connector 435 of the connector 411 through a signal cable 434, and is connected to an image forming circuit 437 for executing signal processing of the image forming and a distance computing circuit 438 for executing distance computation and the like, through a signal connector receptor 436 to which the signal connector 435 is connected.

An output signal from the image forming circuit 437 is displayed on a screw of the monitor 406. The image forming circuit 437 executes signal processing for generating a standard image signal from an output signal from the CCD 432, and outputs an image of the subject 426 toward the monitor 406 with the circumference masked by endoscope display frame data generated by a ROM (not shown) and the like.

The distance computing circuit 438 executes computation of the three dimensional information such as a distance and the like to the spot position of the measuring light formed on the CCD 432 and the surface of the subject 426, on the basis of the output signal from the CCD 432. Detection of the spot position on the surface of the CCD 432 is arranged such that an output signal from the CCD 432, for example, passes through the color separating circuit, color signal components of the light emitting elements 423i are extracted, and the color signal components are compared with reference levels by a comparator or the like, whereby it is possible to detect the spot from the output signal from the CCD 432, and detection of the spot position on the surface of the CCD 432 can be executed by measurement of the detected timing. In this manner, hues are changed to a degree at which the luminescent colors of the light emitting elements 423i are easy to be separated from each other, such that the spot can easily be detected from the output signal from the CCD 432 in the twenty-first embodiment.

Information for computation of distance and positional data produced by spot-position detection processing finding the spot position, that is, information such as a focal length of the projecting lens 427 and the focal length of the objective lens 432, a distance between the optical-axes thereof, a position (relative position from an optical axis of the projecting lens 427) of the laser light incident upon the incident end surface of the image guide 417 (the positional data are outputted to the distance computing circuit 38 from the measuring-light scanning control means 30) and the like, are used to execute computation using the principle of triangulation, thereby computing the distance to the spot position on the surface of the subject 426. The computing data signal is superimposed by a superimpose circuit (not shown) of the image forming circuit 437, and is outputted toward the monitor 406.

An output signal from a mouse 439 for assigning the scanning region is also inputted to the image forming circuit 437. The image forming circuit 437 generates a cursor display signal, superimposes the cursor display signal onto the image signal corresponding to the endoscope image, and outputs the superimposed signal to the monitor 406. Accordingly, the cursor display signal is displayed as a cursor which is moved on the monitor screen in accordance with operation of the mouse 439.

Figure 39:
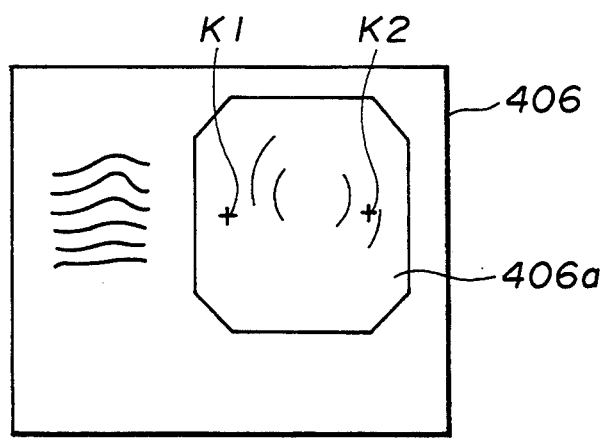

The mouse 439 is operated whereby the cursor for assigning the scanning range is moved on the monitor screen. A click button is operated whereby one end of the scanning range is assigned. The cursor is further moved. The click button is again operated whereby the other end can be assigned. By this assignment of the two ends, the scanning range in a case, for example, where the spot rows are scanned in a direction perpendicular to the spot rows can selectively be set. In FIG. 39, K1 and K2 in the endoscope image display area 406a indicate an example of the scanning range assigned by the cursor operation due to the mouse 439.

When the assigning signals due to operation of the click button are generated, the image forming circuit 437 outputs the positional information of the cursors on the assigned monitor screen, to the measuring-light scanning control means 430. Distance information from the distance computing circuit 438 is also inputted to the measuring-light scanning control means 430. The scanning range control circuit 442 uses these information to compute that the group of light emitting elements 423 is in agreement with the scanning range assigned on the monitor screen if how the group of light emitting elements 423 is moved (scanned). A drive signal corresponding to the scanning range is outputted to the piezo-electric element 428. The optical spot rows projected onto the surface of the subject 426 are scanned only by the scanning range corresponding to the scanning range on the monitor screen assigned by the mouse 439.

Further, in the present embodiment, as shown in FIG. 37, in a case where the table 429 is vibrated in the vertical direction (in synchronism with the period of time of one frame or one field), the measuring-light beam rows scan the fiber bundle in the vertical direction A on the side of the incident end surface of the image guide 417 (scanning in the horizontal direction in FIG. 38). By this scanning, a condition on the side of the outgoing end corresponds to a condition in which scanning is executed in a direction perpendicular to the sheet surface in FIG. 437, on the side of the outgoing end surface.

Furthermore, the table 429 is so arranged as to be vibrated in a stepwise manner, and the pitch of the steps can selectively be set by selective operation of the mouse 439 or the like, for example. If the pitch decreases, the numbers of spots with respect to a unit length in the scanning direction increase too much so that there are many measuring points. Thus, measurement can be executed in detail. On the other hand, when the pitch is set large, there can be produced measuring results of the entire scanning area for a short period of time. In a case where measurement is executed, the pitch can selectively be set.

Figure 40:
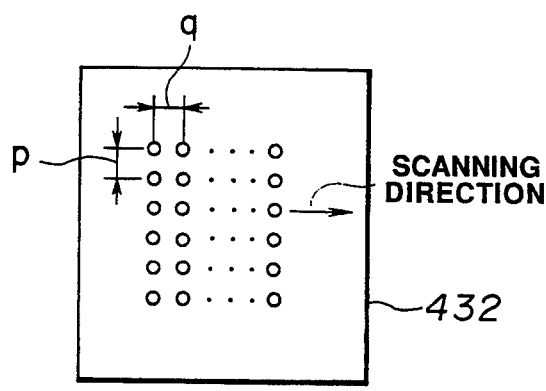

In a case, for example, where the surface of the subject 426 is planar, and the laser light is vibrated stepwise under a condition that the end surface of the forward end portion 4121 is confronted vertically against the surface of the subject 426, the spot rows consisting of the spots at almost constant intervals p (the intervals p correspond to the intervals s in FIG. 38) appear on the image pickup surface of the CCD 432 at almost constant intervals in a scanning direction extending perpendicularly to the spot rows, correspondingly to the stepwise scanning as shown in FIG. 40. In a case where the pitches are made constant, the intervals q between the adjacent spot rows vary depending upon the distance between the forward end portion 412 (the object lens 431 thereof) and the subject 426. A distance to the positions (on the surface of the subject 426) where the spots are actually formed can be computed on the basis of the principle of triangulation.

On the other hand, in a case where the surface of the subject 426 is irregular, spot rows which are not spaced apart from each other at predetermined intervals appear in the scanning direction in accordance with the irregular surface. Also in this case, it is possible to compute the distance to the spot position actually formed on the surface of the subject 426, with the use of the principle of triangulation from the positional information of the spots on the CCD 432. The distance computing circuit 438 executes this computation of distance.

The principle finding the spot position (X, Y, Z) in a case where scanning is executed in a plane connecting the optical axis of the projecting lens 27 and the optical axis of the objective lens 31 to each other is the same as that in FIG. 16 of the ninth embodiment and, accordingly, the description thereof will be omitted.

In connection with the above, at least six measurements due to the measuring light can be executed during the period of time of one field or one frame. If there are a case where it is impossible to execute computation of distance because the spot cannot be formed due to the fact that there is no cavity portion or the like (or because the return light of the spot can be detected), a case where, even if the spot is formed on the surface of the subject 26, computation of distance cannot be executed because of out of the image pickup region (or the region of a field of view), and a case where the level of the return light of the projected spot cannot be detected because the level of the return light of the projected spot has not so much difference with respect to the surrounding or circumferential level, and the like, the distance computing circuit 438 outputs a signal such as incapability of measurement or the like to the image forming circuit 437, because the distance computing circuit 438 cannot detect the spot position, or the like. The distance computing circuit 438 displays that effect on the monitor screen.

This display is executed in a case, for example, where detection of the spot position is not executed till time set by a timer (not shown). Moreover, in a case where a plurality of spots are formed during a period of time of one field or one frame as illustrated in FIG. 40, if the numbers of spots to be detected are different from the numbers of spots expected to be projected, inconsistency or the like can be displayed on the monitor 406.

Furthermore, the distance computing circuit 438 computes a component in the distance direction connecting the subject 426 and the forward end portion 412 (the objective lens 431 thereof) to each other, or a height component in a direction perpendicular to the surface of the subject 426, that is, the amount of irregularity of the surface of the subject 426, together with computation of the distance, and outputs the irregularity data signal to the image forming circuit 437. The image forming circuit 437 superimposes the irregularity data signal on the image signal representing the endoscope image to output the superimposed image to the monitor 406. The image forming circuit 437 displays the computed irregularity data on the left-hand portion of the endoscope image display area 306a as illustrated in FIG. 39, for example, over the scanning region (for example, a region connecting K1 and K2 to each other) of the measuring spots of respective colors in the monitor display screen.

The twenty-first embodiment is arranged such that hues of the measuring light are changed and, on the other hand, the signal processing system of measuring-light detection in the distance computing circuit 438 is formed in accordance with the hues, whereby, even in a case where a plurality of measuring lights are projected simultaneously on the subject 426, a signal detecting system is provided correspondingly to the characteristics of the respective measuring lights, in this case, correspondingly to the hue, so that they are ensured to be capable of being detected in separation.

Specifically, since the lights having six colors, for example, different in hue from each other as described previously are used as measuring lights, light spots having six colors are simultaneously formed on the surface of the subject 426. In this case, since the optical spots are different in color from each other, even if the optical spots are piled up on the surface of the CCD 432 (because the irregularity of the surface of the subject 426 is violent, and the like), or are intersected with each other, it is possible to ensure that the positions of the respective optical spots on the surface of the CCD 432 are detected by the corresponding signal detecting system.

Accordingly, according to the present embodiment, many measuring-light spots per unit time can be formed on the surface of the subject 426, and the measuring-light spots can be so ensured as to be identified in separation from the output signal from the CCD 432. As a result, there can be produced many distance information, and irregularity information. Thus, there can be produced information required for diagnosis or the like for a short period of time. Further, since it is possible to produce the information required for diagnosis or the like for a short period of time, pain of a patient can be reduced, and a burden of an operator can also be reduced. For this reason, exact or accurate diagnosis is apt to be given.

Figure 41:
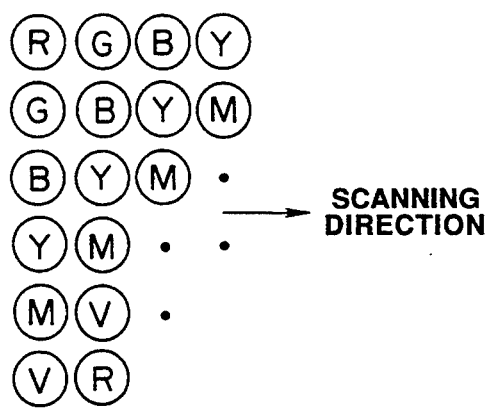

In connection with the above, the arrangement may be such that, in a case where the spot rows are scanned, the group of light emitting elements 423 and the group of condenser lenses 424 are moved a predetermined or constant amount in a direction perpendicular to the scanning direction every the spot rows are moved every predetermined or constant pitches (in this case, in FIG. 37, for example, the piezo-electric element 428 is provided for being moved in a direction perpendicular to the moving direction due to the piezo-electric element 428. Further, the numbers of the group of light emitting elements 423 or the like increase), and six colors are irradiated cyclically in the scanning direction to the incident end surface of the image guide 417 as illustrated in FIG. 41. In this connection, in FIG. 41, R, G, B, Y, M and V schematically indicate loci along which optical beams having hues of red, green, blue, yellow, magenta and cyanogen are irradiated.

In connection with the above, the arrangement may be such that, in FIG. 41, the moving pitches in a direction perpendicular to the scanning direction increase so that separation is further ensured to be executed. In this connection, although the present embodiment uses six (6) colors, the colors may be changed, and the numbers of hues may increase and decrease.

An endoscope apparatus for three dimensional measurement, according to a twenty-second embodiment of the invention will next be described.

Figure 42:
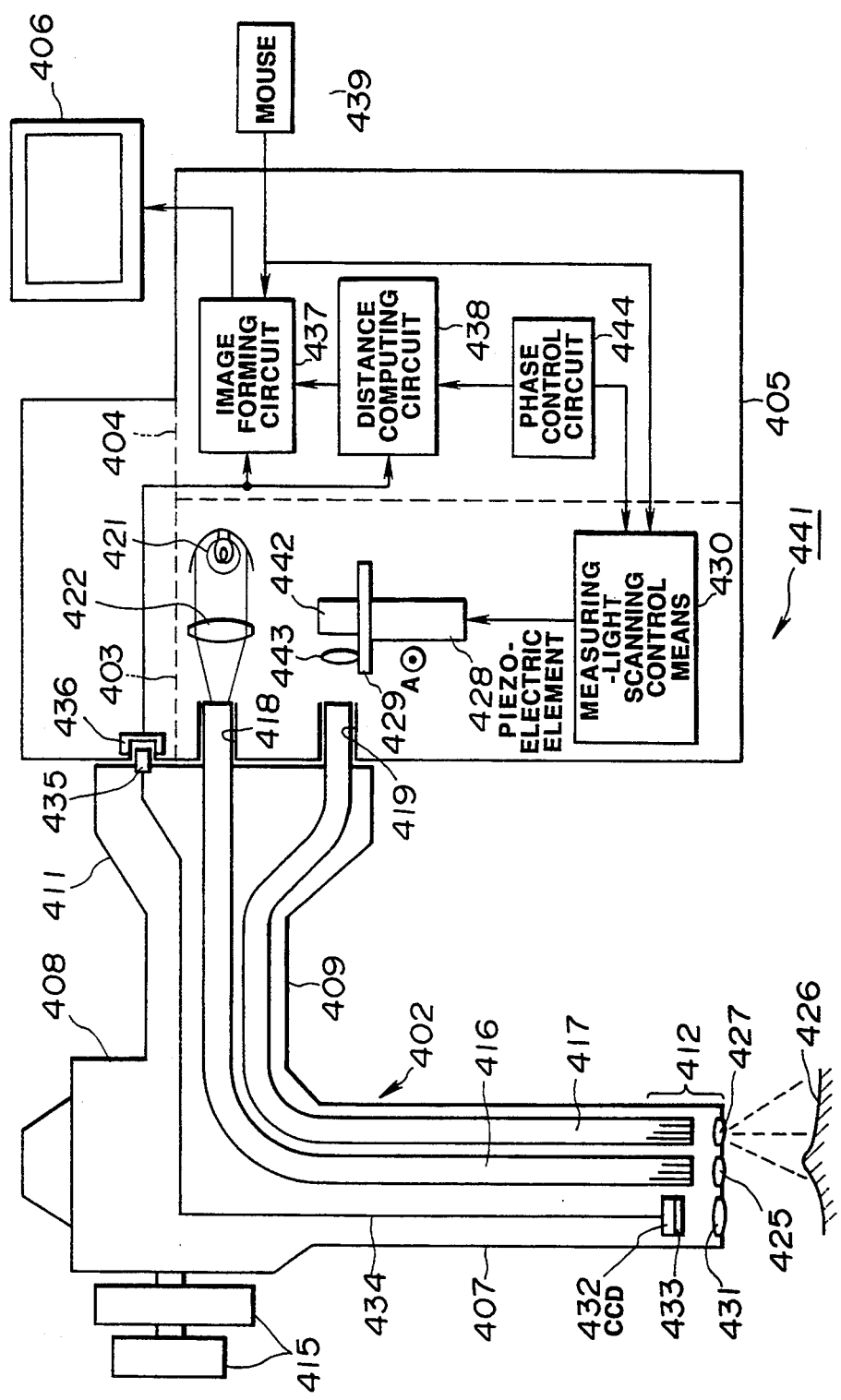
FIG. 42 is a view showing an arrangement of an endoscope apparatus for three dimensional measurement according to a twenty-second embodiment of the invention.

The present embodiment is arranged such that a phase of a measuring light Is changed and is scanned. As shown in FIG. 42, the present embodiment uses a semiconductor laser 442 in place of the group of light emitting elements 423 in the twenty-first embodiment illustrated in FIG. 37. A laser light from the semiconductor laser 442 is irradiated to an incident end surface of an image guide 417 through a condenser lens 443. The semiconductor laser 442 is controlled in phase by a phase control circuit 444.

Specifically, the phase of the laser light is changed in synchronism with the fact that the laser light is scanned in a scanning direction. The phase control is arranged such that drive current supplied to the semiconductor laser 442, for example, is amplitude-modulated by a signal having an adequate frequency in synchronism with a cycle of a drive signal to a piezo-electric element 428. The signal is inputted to a measuring-light scanning control means 430. The piezo-electric element 428 is driven in synchronism with the signal, for example. As a result, a characteristic is given in which the strength or intensity of the optical spot projected onto a surface of a subject 426 is changed cyclically or periodically.

In a case where a spot is detected from an output signal from a CCD 432, the periodicity is utilized whereby separation or the like with respect to the adjacent spots is facilitated. Even if a plurality of optical spots are formed per unit time, it is possible to ensure that separation thereof is executed. Thus, the twenty-second embodiment has advantages similar those of the first embodiment. In this connection, the arrangement may be such that a piezo-electric element in addition to the piezo-electric element 428, for example, is further provided and the like to move (vibrate) a table 429 vertically, for example, so that the measuring light is scanned two-dimensionally.

An endoscope apparatus for three dimensional measurement according to twenty-third embodiment of the invention will next be described.

Figure 43:
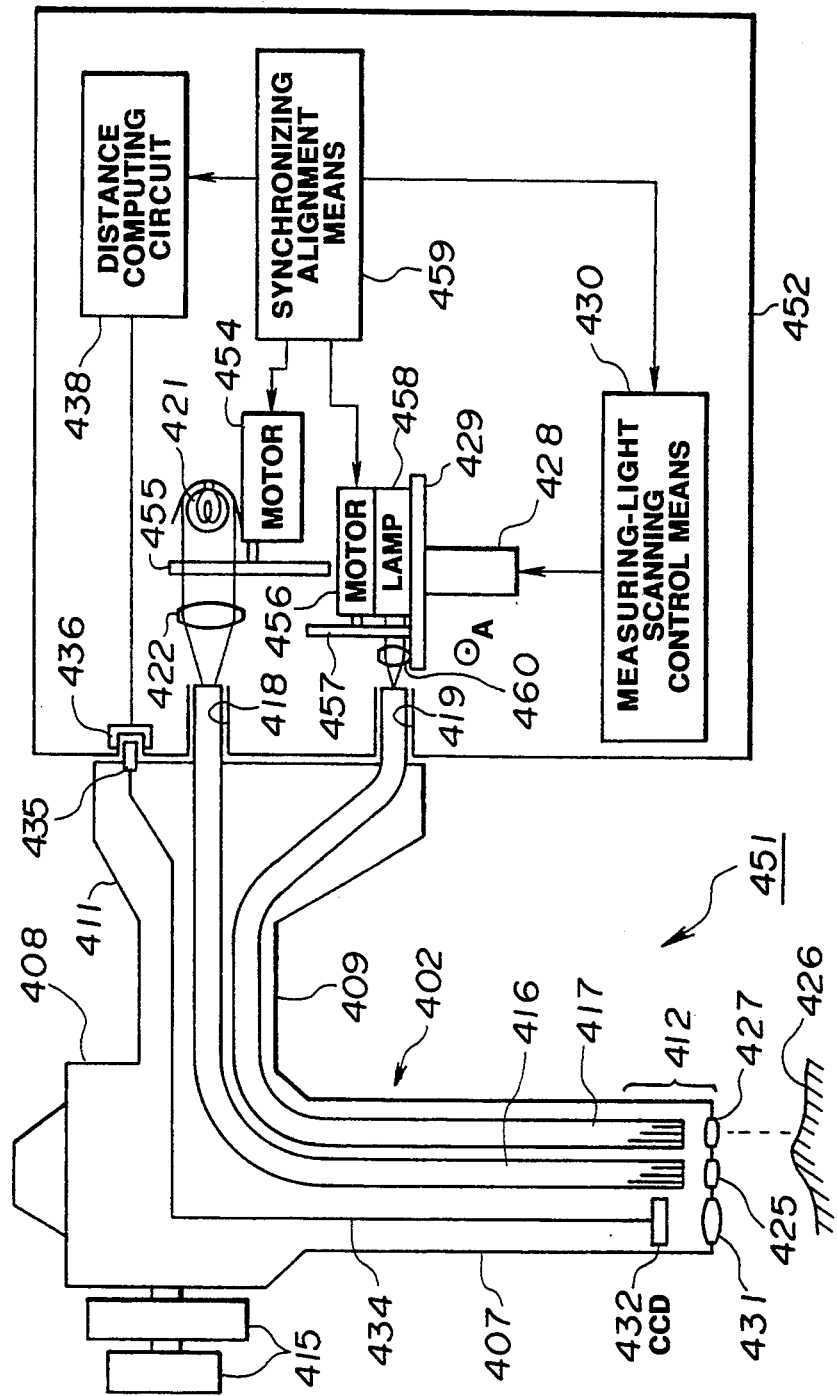
FIG. 43 is a view showing an arrangement of an endoscope apparatus for three dimensional measurement according to a twenty-third embodiment of the invention.

The present embodiment is arranged such that a measuring light is in synchronism with illumination of an illuminating light to execute scanning of the measuring light. As shown in FIG. 43, in an endoscope apparatus 451 for three dimensional measurement, according to the present embodiment, illuminating means of surface subsequence is used as ordinary illuminating means. Specifically, a white light from a lamp 421 is irradiated to an RGB rotary disc 455 which is rotatively driven by a motor 454, at a location in rear of a connector receptor 418 of a light source unit 452. The white light passes through the RGB rotary disc 455 whereby the white light is brought to an RGB illuminating light of surface subsequence. The white light is further condensed by a condenser lens 422 and is supplied to an incident end surface of a light guide 416.

On the other hand, a white light of a lamp 458 is irradiated to an RGB rotary disc 457 which is rotatively driven by a motor 456, also at a location in rear of a connector receptor 419 to which an incident end portion of an image guide 417 is connected. The white light passes through the RGB rotary disc 457, whereby the white light is brought to an RGB illuminating light of surface subsequence. The white light is further condensed by a condenser lens 460 and is supplied to the incident end surface of the image guide 417.

The motors 454 and 456 are controlled in rotary phase by synchronizing alignment means 459 such that a constant or predetermined phase difference is retained so as to be rotatively driven.

In the present embodiment, rotary phases of both the motors 454 and 456 are controlled by the synchronizing alignment means 459 such that the relationship is so maintained as to the fact that a measuring light of a green color is irradiated to a subject 426, for example, during a period of time the illuminating light of surface subsequence is red, that a measuring light of a blue color is irradiated to the subject 426 during a period of time the illuminating light of surface subsequence is green, and that a measuring light of a red color is irradiated to the subject 426 during a period of time the illuminating light of surface subsequence is blue.

A signal of the rotary phase is supplied to measuring-light scanning control means 430, to execute scanning in synchronism with the rotary phase. Furthermore, the signal of the rotary phase is inputted also to a distance computing circuit 438, and is used when spot detection from a CCD 432 is executed. For example, since the levels of the return light of the measuring light are different from each other, the level of spot Judgment is brought to an adequate value in accordance with the projected color. In the present embodiment, the color of the measuring light is also changed in synchronism with the fact that the illuminating light is changed in a manner of passage of time, whereby it is possible to increase the numbers of spots per unit time, and it is possible to secure that detection is executed.

For example, scanning is executed such that the measuring light of green color is irradiated to the subject 426 during a period of time the illuminating light of surface subsequence is red; although the intervals between the illuminating lights cannot so much decrease, the intervals of the measuring light of the green color are filled up when the measuring light of blue color is irradiated to the subject 426, during a period of time the illuminating light of the surface subsequence is green; and when the subsequent measuring light of red is irradiated to the subject 426, the intervals between the measuring lights are filled up. By the scanning in this manner, it is possible to form a plurality of measuring-light spots during a period of time of one frame and, as a result, separation is possible with high resolution.

In connection with the above, in the present embodiment, a rotary disc provided with many color filters is used in substitution for the RGB rotary disc 457 so that the former rotary disc has higher resolution.

An endoscope apparatus for three dimensional measurement, according to a twenty-fourth embodiment of the invention, will next be described.

The twenty-fourth embodiment is substantially the same as the twenty-third embodiment and, accordingly, only arrangements different therefrom will be described.

Figure 44:
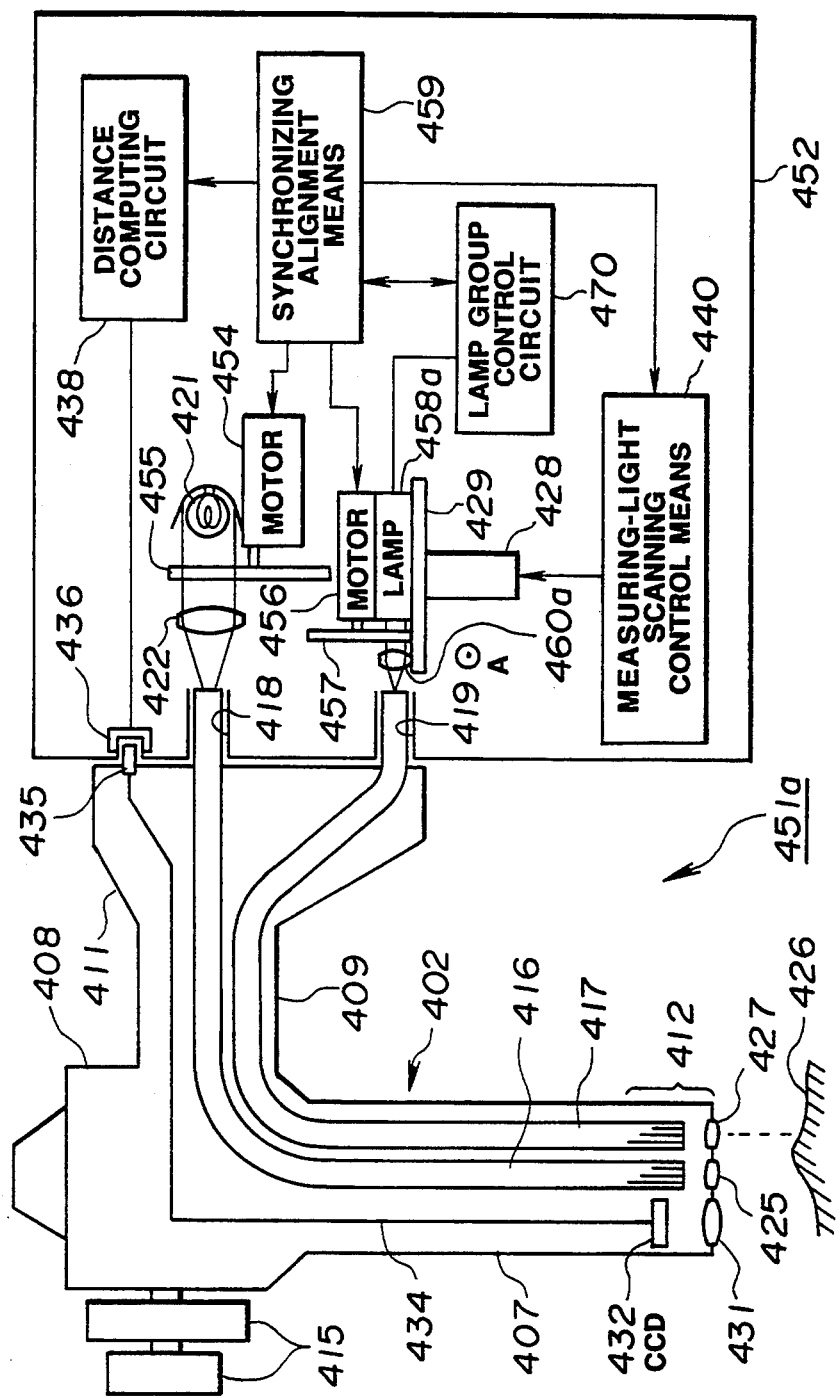
FIGS. 44 through 46 are views showing a twenty-fourth embodiment of the invention, FIG. 44 being a view showing an arrangement of an endoscope apparatus for three dimensional measurement, FIG. 45 being a view showing an arrangement of a lamp-group control circuit, and FIG. 46 being a view showing an arrangement of a modification of the lamp-group control circuit.

As shown in FIG. 44, an endoscope apparatus 451a for three dimensional measurement, according to the twenty-fourth embodiment, is provided with a group of lamps 458a for supplying a plurality of white illuminating lights in place of the lamp 458 in the twenty-third embodiment, a group of condenser lenses 460a for condensing the plurality of white illuminating lights from the group of lams 458a to an incident end surface of an image guide 417 in place of the condenser lens 460, and a lamp-group control circuit 470 for controlling brightness of the plurality of white illuminating lights from the group of lamps 458a every the plurality of white illuminating lights in synchronism with rotation of a pair of motors 454 and 456.

Figure 45:
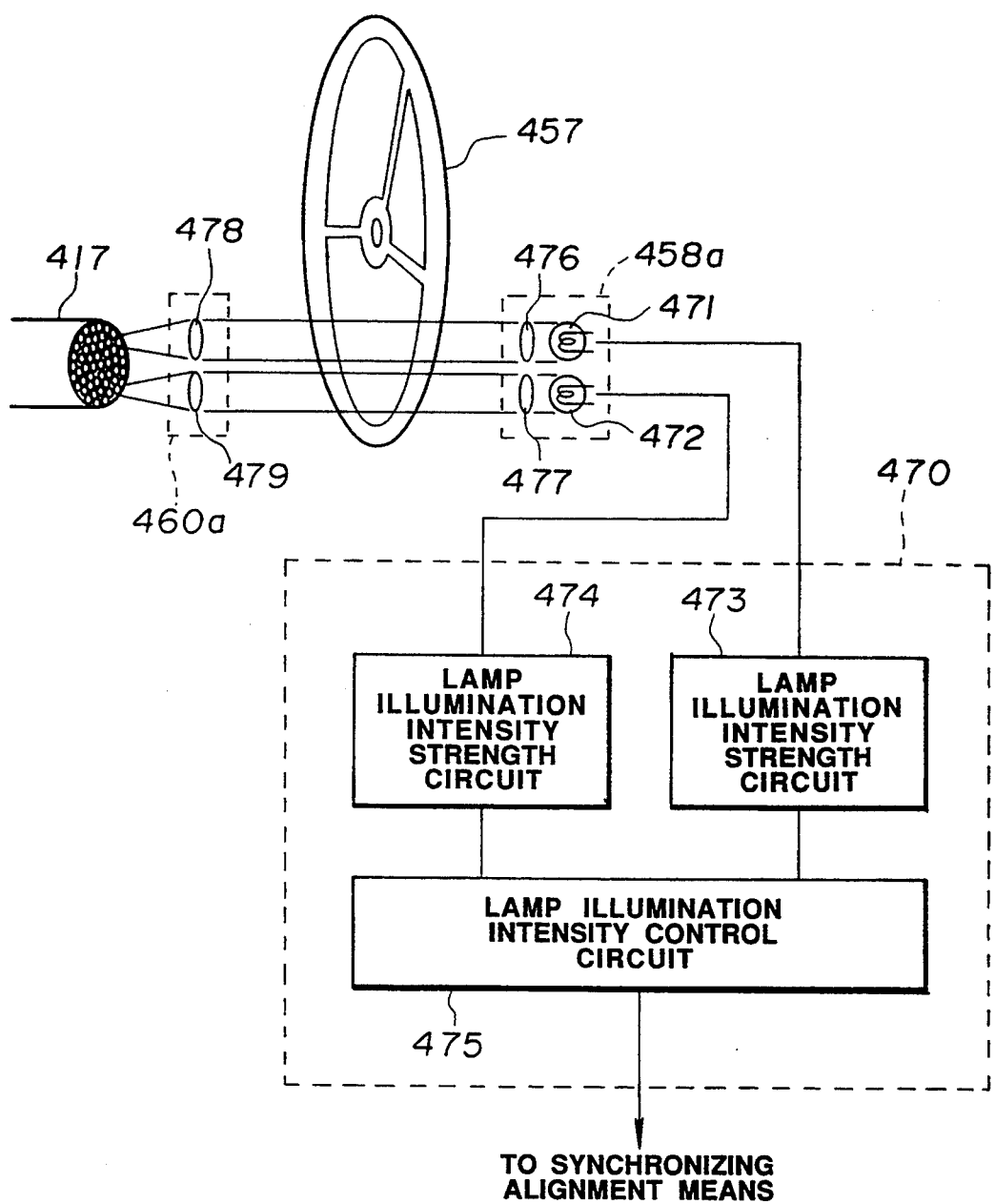

As shown in FIG. 45, the lamp-group control circuit 470 has a pair of lamp illumination-intensity strength circuit 473 and 474 for driving a pair of white illumination lamps 471 and 472, for example, forming the group of lamps 458a so as to change brightness thereof, and a lamp illumination-intensity control circuit 475 for controlling the lamp illumination-intensity strength circuit 473 and 474 while taking synchronism with rotation of the motors 454 and 456, as described above. The illuminating lights from the respective lamps 471 and 472 for white illumination controlled by the lamp-group control circuit 470 are so arranged as to be condensed to an incident end surface of the image guide 417 through lenses 476 and 477 and an RGB rotary disc 457 within the group of lamps 458a, and further through lenses 478 and 479 within the group of condenser lenses 460a. Other arrangement is the same as that of the twenty-third embodiment.

In the twenty-fourth embodiment arranged in this manner, the lamp illumination-intensity control circuit 470 changes the brightness of each of the lamps 471 and 472, every color of the RGB rotary disc 457, by the use of the lamp illumination-intensity strength circuits 473 and 474, while taking synchronism with rotation of the motors 454 and 456. The lights from the lamps 471 and 472 are condensed onto the incident end surface of the image guide 417 through the lenses 476, 477 and 478, 479.

Moreover, the lamp illumination-intensity control circuit 470 transmits strength information of the illumination intensity in the lamps 471 and 472 every colors of the RGB rotary disc 457, to a distance computing circuit 438 through a synchronism alignment means 459.

The distance computing circuit 438 predicates color information of a measuring point on the basis of the intensity information, extracts the falling-under measuring point to execute distance computation, and similarly measures other measuring points.

Other functions are the same as that of the twenty-third embodiment.

Accordingly, the twenty-fourth embodiment can compute a plurality of distances during a period of time of one frame, in addition to the advantages of the twenty-third embodiment.

Figure 46:
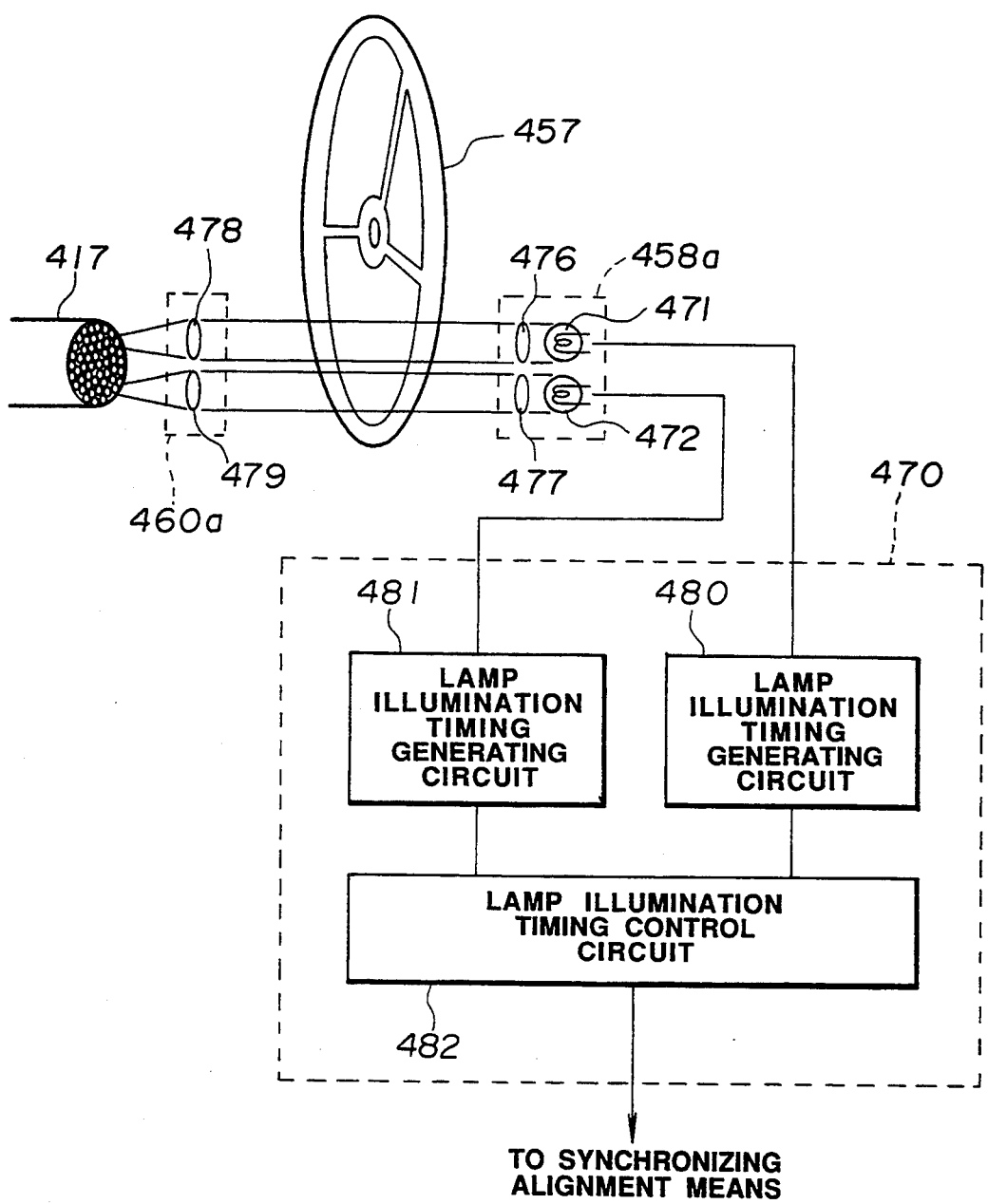

In connection with the above, the lamp-group control circuit 470 may be arranged as shown in FIG. 46. Specifically, the lamp-group control circuit 470 may be formed by a pair of lamp illumination-intensity timing generating circuits 480 and 481 for generating timing signals of the illumination of the lamps, and a lamp illumination timing control circuit 482 for controlling the lamp illumination timing generating circuits 480 and 481, in place of the lamp illumination-intensity strength circuits 473 and 474 illustrated in FIG. 45.

In the lamp-group control circuit 470 as shown in FIG. 46, the lamp illumination timing control circuit 482 uses the lamp illumination timing generating circuits 480 and 481 while taking synchronism with rotation of the motors 454 and 456, to change illuminating times of the lamps 471 and 472 for each of the colors of the RGB rotary disc 457.

Further, the lamp illumination-intensity control circuit 470 transmits illumination-time information in the lamps 471 and 472 for each of the colors of the RGB rotary disc 457 to the distance computing circuit 438 through the synchronizing alignment means 459.

The distance computing circuit 438 predicates the color information at the measuring point on the basis of the illumination-time information, extracts the falling-under measuring point to execute distance computation, and similarly measures other measuring points.

Accordingly, even if the lamp-group control circuit 470 as shown in FIG. 46 is used, there can be produced similar advantages.

An endoscope apparatus for three dimensional measurement, according to a twenty-fifth embodiment of the invention, will next be described.

Figure 47:
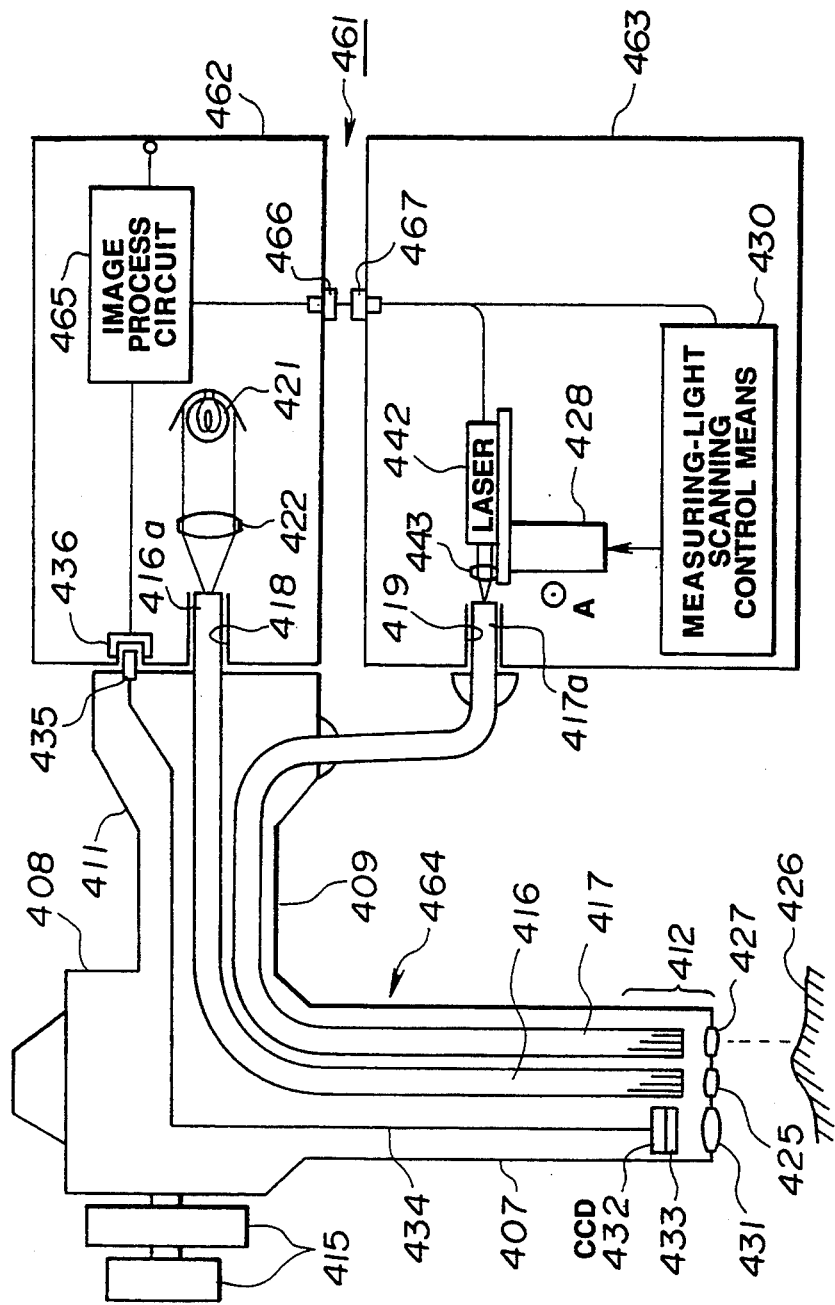
FIG. 47 is a view showing an arrangement of an endoscope apparatus for three dimensional measurement according to a twenty-fifth embodiment of the invention.

As shown in FIG. 47, the present embodiment is arranged such that a light-source.processing unit 405 of the twenty-second embodiment, for example, is formed by an ordinary inspection process unit 462 separated into two elements, and a measurement process unit 463.

Moreover, an electronic scope 464 of the present embodiment is arranged such that a connector 417a of an image guide 417 is formed in separation from a connector 416a of a light guide 416. Specifically, a hand-portion of the image guide 417 can extend to the outside from an overall connector 411, and the connector 417a at an end thereof can detachably be connected to a connector receptor 419 of the measurement process unit 463.

Furthermore, an image process circuit 465 within the measurement process unit 462 is so arranged as to be capable of being connected to measuring-light scanning control means 430 within the measurement process unit 463, through the connecting connectors 466 and 467. The image process circuit 465 in the present embodiment represents the image forming circuit 437, the distance computing circuit 438, the phase control circuit 444 and the mouse 439 in FIG. 42. The present embodiment has advantages similar to those of the twenty-second embodiment.

An endoscope apparatus for three dimensional measurement, according to a twenty-sixth embodiment of the invention, will next be described.

Figure 48:
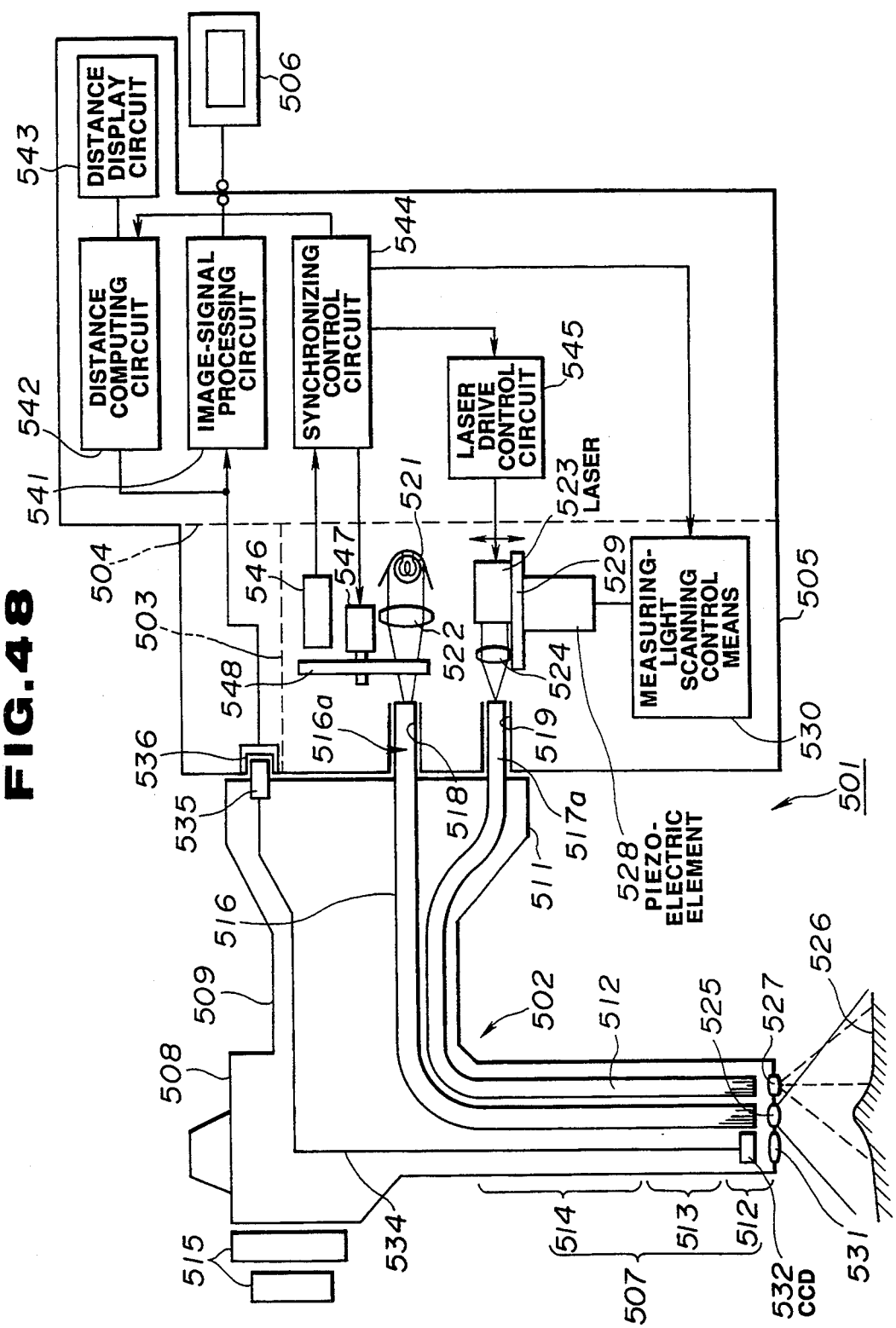

As shown in FIG. 48, an endoscope apparatus 501 for three dimensional measurement, according to the twenty-sixth embodiment, comprises an electronic scope 502 building therein image pickup means, a light processing unit 505 building therein ordinary illuminating-light supply means for supplying an ordinary illuminating light to the electronic scope 502, measuring-light light-source means 503 and signal processing means 504 for executing signal processing and distance computation, and a color monitor 506 for displaying a standard image signal generated in signal processing by the signal processing means 504.

The electronic scope 502 has an inserting section 507 which is elongated and which has flexibility so as to be insertable into a body cavity or the like, an operating section 508 which is wide in width and which is connected to a rearward end of the inserting section 507, and a universal cable 509 extending from a side of the operating section 508. An overall connector 511 mounted on the end of the universal cable 509 can detachably be connected to the light-source.processing unit 505.

The inserting section 507 has, from its forward end, a hard forward end portion 512, a curving portion 513 capable of being curved, and a flexible tube portion 514 which is flexible. A pair of curving knobs 515 mounted on a side surface of the operating section 508 are operated whereby the curving portion 513 can be curved.

A light guide 516 for transmitting an ordinary illuminating light and an image guide 517 serving as measuring-light transmitting means for transmitting a measuring light are inserted in the inserting section 507. The light guide 516 and the image guide 517 are inserted also in the universal cable 509. A light guide connector 516a and an image guide connector 517a at respective ends are integrally fixed to each other by the overall connector 511.

The light-source.processing unit 505 is provided, within the light-source.processing unit 505, with a light guide connector receptor 518 and an image guide connector receptor 519 to which the light guide connector 516a and the image guide connector 517a are detachably connected, respectively. Arranged within the light-source.processing unit 505 is a lamp 521 for generating a white light at a location in rear of the light guide connector receptor 518, a condenser lens 522 for condensing a white illuminating light from the lamp 521, and an RGB rotary disc 548, for example, rotatively driven by a motor 547, which separates the illuminating light condensed by the condenser lens 522 and irradiated to the light guide connector 516a, to an RGB light.

Furthermore, a semiconductor laser 523 for generating a laser light and a condenser lens 524 are arranged in rear of the image guide connector receptor 519, within the light-source.processing unit 505. The arrangement is such that the laser light capable of being condensed due to the semiconductor laser 523, that is, a measuring light is condensed by the for condenser lens 524, and the measuring light for executing scanning in a straight-line manner as shown, for example, in FIG. 50(a) is irradiated to an end surface of the fiber bundle forming the image guide connector 517a.

As shown in FIG. 51, the RGB rotary disc 548 is arranged as follows. That is, the RGB rotary disc 548 is provided with filters R, G and B corresponding respectively to RGB. Filter start marks 550a, 550b and 550c and a one-revolution start mark 551 are provided between the filters R, G and B. These marks are read out by a mark readout circuit 546 in FIG. 48. There can be produced rotary-position information of the RGB rotary disc 548 which is rotated by the motor 547.

The illuminating light supplied to the light guide connector 516a is transmitted by the light guide 516, and is further emanated toward a subject 526 through an illuminating lens 525 from an end surface adjacent to the outgoing side which is fixed to the forward end portion 512, to illuminate a location adjacent to the subject 526 in a wide area manner. The illuminating lens 525 is mounted at a distance different from a focal distance of the illuminating lens 525 from the end surface of the light guide 516 adjacent to the outgoing side.

Moreover, the measuring light irradiated to the image guide connector 517a is transmitted by the fibers to which the measuring light in the image guide 517 is irradiated. The measuring light is emanated toward the subject 526 further through a projecting (light projecting) lens 527 from the end surface adjacent to the outgoing side fixed to the forward end portion 512, to form a minute optical spot onto the surface of the subject 526. The projecting lens 527 is mounted at a focal distance of the projecting lens 527 from the end surface of the image guide 517 adjacent to the outgoing side. The measuring light emanated from the fibers at the end surface adjacent to the outgoing side can form a minute optical spot on the surface of the subject 526, without substantial spreading.

The semiconductor laser 523 and the condenser lens 524 are mounted on a table 529 which is driven by a piezo-electric element 528 in a vibratory manner. A drive signal from measuring-light scanning control means 530 is applied to the piezo-electric element 528, whereby the piezo-electric element 528 is caused to vibrate in a vertical direction as indicated for example, by an arrow in FIG. 48. By this vibratory movement, the semiconductor laser 523 is also similarly vibrated so that the measuring light scans the side of the subject 526 in a straight-line manner through the projecting lens 527.

The piezo-electric element 528 is driven by, for example, a drive signal in the form of a stepwise wave from the measuring-light scanning control means 530. By this driving, the measuring light irradiated to the fiber bundle of the image guide connector 517a is successively irradiated every fibers spaced a predetermined or constant interval away from each other, and scans the region of substantially a diameter of the fiber bundle in a stepwise manner and in a straight-line manner, as illustrated in FIG. 50(a).

The subject 526 illuminated by the illuminating light in a wide area manner is imaged onto an image pickup surface of a CCD 532 serving as an image pickup element arranged at a focal surface of an objective lens 531, by the objective lens 531 which is mounted on an observation window in the forward end portion 512.

The CCD 532 is connected to a signal connector 535 in the connector 511 through a signal cable 534, and is connected to an image signal processing circuit 541 and a distance computing circuit 542 through a signal connector receptor 536 to which the signal connector 535 is connected. The image signal processing circuit 541 generates a standard image signal by the image pickup signal from the CCD 532, and outputs the standard image signal to the monitor 506. Furthermore, the distance computing circuit 542 is so arranged as to compute a distance to the subject 526 on the basis of the image pickup signal due to the measuring light, and outputs a value of the distance to a distance display circuit 543 so that a distance can be displayed by the distance display circuit 543.

Moreover, a synchronizing control circuit 544 controls the image signal processing circuit 541, and the measuring-light scanning control means 530, the motor 547 and a laser driving control circuit 545 for controlling light emitting of the semiconductor laser 523, on the basis of the positional information of the RGB rotary disc 548 produced by a mark readout circuit 546, and selectively separates the image pickup signal due to the measuring light with respect to the distance computing circuit 542 correspondingly to light emission of the semiconductor laser 523.

In the present embodiment, the objective lens 531 and the projecting lens 527 are provided on the forward end portion 512 in adjacent relation to each other as illustrated, for example, in FIG. 49, and the illuminating lens 525 is provided on one side or both sides thereof, as indicated by the broken line.

Furthermore, in the present embodiment, as shown in FIG. 48, in a case where the table 529 is vibrated vertically, the laser light scans the fiber bundle vertically at a location adjacent to the incident end surface of the image guide 517. By this scanning, the laser light corresponds to a condition in which scanning is made horizontally in FIG. 48 at a location adjacent to the outgoing end surface. The measuring light projected toward the subject 526 through the projecting lens 527 is emanated radially by the projecting lens 527 within a plane m including an optical axis of the objective lens 531 and the optical axis of the projecting lens 527 as illustrated in FIG. 46.

The endoscope apparatus 501 for three dimensional measurement arranged in this manner radiates the semiconductor laser 523 when, for example, the illuminating light is interrupted between the filters R, G and B, on the basis of the positional information of the RGB rotary disc 548 which is produced by the mark readout circuit 546. As described above, the synchronizing control circuit 544 selectively separates the image pickup signal due to the measuring light with respect to the distance computing circuit 542, correspondingly to the light emission of the semiconductor laser 523 on the basis of the positional information of the RGB rotary disc 548, and the table 529 is scanned in a stepwise manner. Accordingly, in a case, for example, where the surface of the subject 526 is planar and the measuring light is scanned under a condition that the end surface of the forward end portion 512 is confronted vertically against the surface, spot rows s having almost constant intervals appear on the image pickup surface of the CCD 532, correspondingly to stepwise scanning as illustrated in FIG. 50(b). The intervals of the spot rows s vary depending upon the distance between the forward end surface of the scope 502 and the subject 526, and it is possible to compute a distance between the actual spots on the basis of the principle of triangulation. The numbers of the spot rows s or pitches in the form of a stepwise wave are set equal to or more than numbers or pitches capable of recognizing in separation the spots on the basis of the output signal from the CCD 532, during a period of time of one field or one frame.

On the other hand, in a case where the surface of the subject 526 is irregular, the spot rows having no constant intervals appear in a straight-line manner in accordance with the irregular surface. Also in this case, it is possible to compute the distance to the spot position actually formed on the surface of the subject 526, from the positional information of the spots on the CCD 532, by the use of the principle of triangulation. Computation of this distance is executed by the distance computing circuit 538.

The principle on the basis of which the spot position (X, Y, Z) is found in a case where scanning is executed in a plane connecting the optical axis of the projecting lens 527 and the optical axis of the objective lens 531 to each other is the same as that in FIG. 16 showing the ninth embodiment and, accordingly, the description thereof will be omitted.

In connection with the above, since there is a case where the spots on the surface of the subject 526 are piled up each other in a portion large in irregularity amount, size or dimension of the pitches in the form of a stepwise wave can be set variably in accordance with the using conditions. The distance computing circuit 538 separates in color the output signal from the CCD 532, extracts a signal component of the wavelength of the laser light, for example, and subtracts an envelope detection signal or a low-pass signal of the signal component from the same to detect a spot, thereby finding the spot position on the surface of the CCD 532.

Here, the semiconductor laser on the basis of the positional information of the RGB rotary disc 548 produced by the mark readout circuit 546 is irradiated three times during one revolution of the RGB rotary disc 548. The measuring light due to the irradiation of three times per revolution is also scanned so that there are produced three spots. Thus, measurement of three points is executed during one revolution of the RGB rotary disc 548, that is, during image pickup time of one frame.

Accordingly, the endoscope apparatus 501 for three dimensional measurement, according to the twenty-sixth embodiment, is arranged such that the image pickup signal due to the measuring light is produced in separation from the image pickup signal from the CCD 532 correspondingly to the timing of the irradiation, by the fact that the measuring light is irradiated during a period of time of interruption of the illuminating lights including R, G and B. Accordingly, it is possible to prevent halation or the like due to the illuminating light from being affected or influenced upon. Thus, it is ensured that three dimensional measurement is executed. Further, since three dimensional measurement of three points can be executed during image pickup time of one frame, it is possible to execute effective measurement.

An endoscope apparatus for three dimensional measurement, according to a twenty-seventh embodiment of the invention, will next be described.

The endoscope apparatus for three dimensional measurement, according to the twenty-seventh embodiment, is substantially the same as that according to the twenty-sixth embodiment and, accordingly, only different arrangements will be described, but the same reference numerals or characters are applied to the same arrangement and the description thereof will be omitted.

Figure 52:
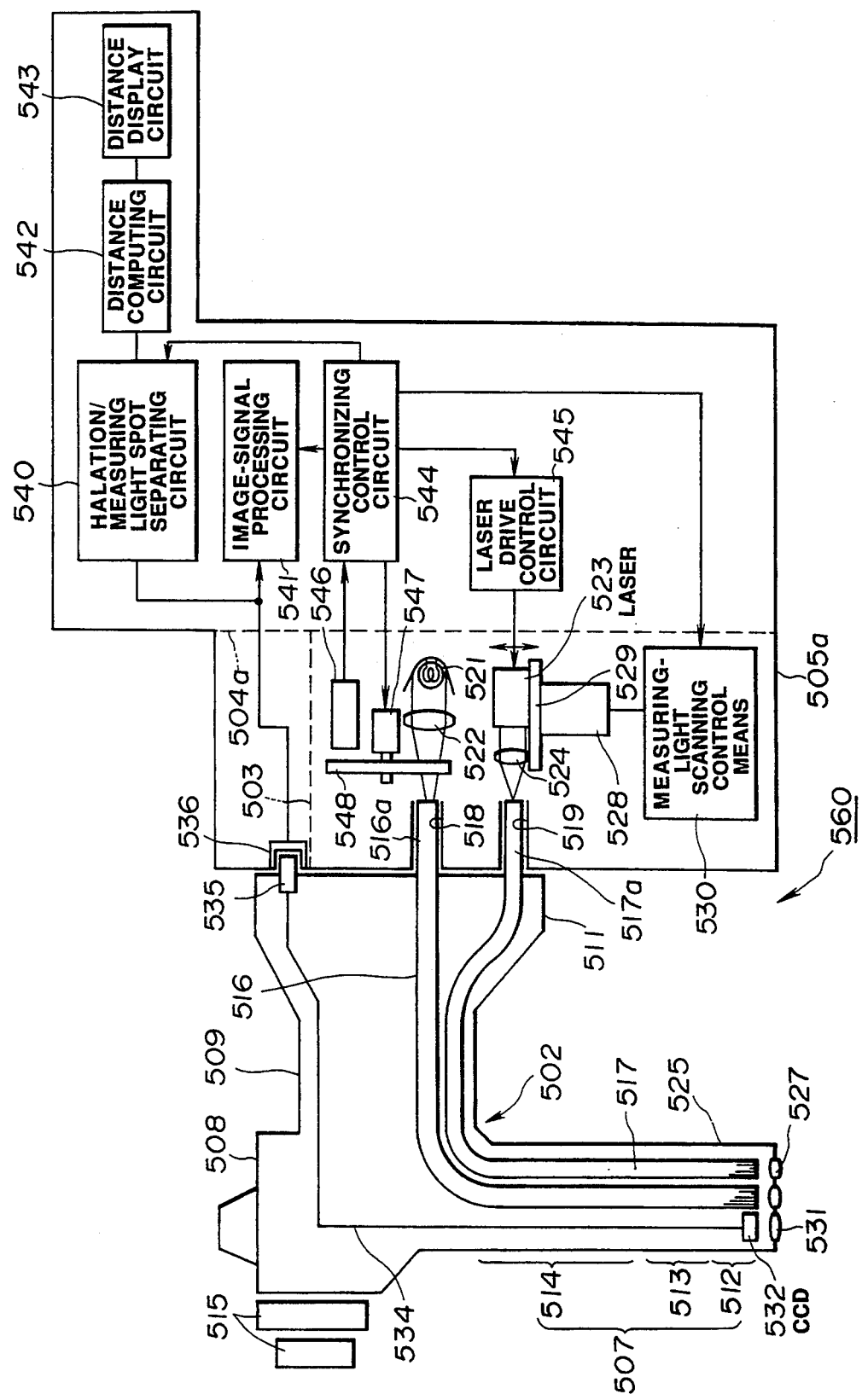

As shown in FIG. 52, in an endoscope apparatus 560 for three dimensional measurement, according to the twenty-seventh embodiment, signal processing means 504a of a light-source.processing unit 505a is controlled by a synchronizing control circuit 544, and a halation/-measuring-light spot separating circuit 540 is provided for outputting halation and a measuring-light spot to a distance computing circuit 542 in separation from an image pickup signal from a CCD 532.

As shown in FIG. 53, the halation/measuring-light spot separating circuit 540 has an R-frame memory 540a for storing therein the image pickup signal from the CCD 532 of R irradiated from an RGB rotary disc 548, for example, on the basis of the control signal from the synchronizing control circuit 544, and a subtracter 540b for subtracting an image pickup signal of R stored in the R-frame memory 540a from the image pickup signal from the CCD 532 of G of the subsequent stage or step, by the synchronizing signal from the synchronizing control circuit 544, as illustrated in FIG. 53, for example. An output (G-R) from the subtracter 540b is outputted to the distance computing circuit 542 as a spot-light detecting signal. Here, timing of illumination of the measuring light is different from that in the twenty-sixth embodiment, and is executed in synchronism with timing of irradiation of the illuminating light of the RGB.

Other arrangements are the same as that of the twenty-sixth embodiment.

The halation/measuring-spot separation circuit 540 arranged in this manner is arranged such that, in a halation area 552, both an R-image pickup signal and a G-image pickup signal of the subsequent step stored in the R-frame memory 540a are brought to a saturated condition, for example, by the control signal from the synchronizing control circuit 544, and take maximum values, as illustrated in FIG. 54(a) and FIG. 54(b). Accordingly, a signal (G-R) subtracted by the subtracter 540b is extinguished or reduced in the halation area 552 as illustrated in FIG. 54(c).

Moreover, the optical spot due to the measuring light is brought to a saturated condition only at G-illumination in the spot area, if, when the illuminating light executes R-illumination, the optical spot is not irradiated, as shown, for example, in FIG. 55(a), and if, when illumination is executed at the time the illumination light executes G-illumination, the optical spot is irradiated as illustrated in FIG. 55(b). The CCD 582 generates a signal of the maximum value within the area. Accordingly, the signal (G-R) subtracted by the subtracter 540b is detected as a spot-light signal in the spot area as illustrated in FIG. 55(c), and is outputted to the distance computing circuit 542 of the subsequent stage.

Other functions are the same as that of the twenty-sixth embodiment.

Figure 58:
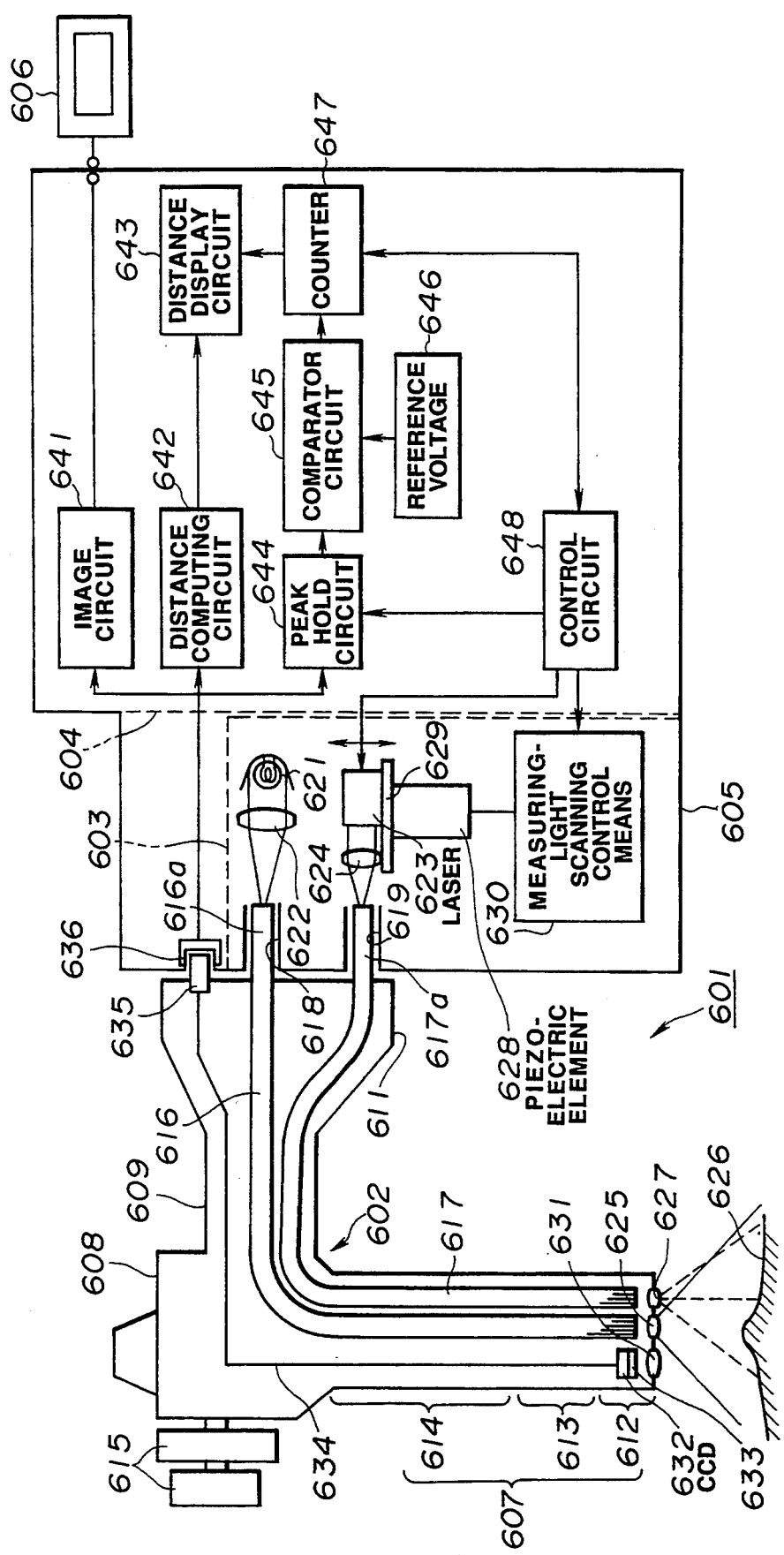

In connection with the above, the halation/measuring-spot separation circuit 540 has been arranged as illustrated in FIG. 58. However, the halation/measuring-spot separation circuit 540 should not be limited to this specific one. For example, as shown in FIG. 56, the halation/measuring-spot separation circuit 540 may be one which comprises a frame memory 540c for storing therein an image pickup signal from the CCD 532, a maximum-value region area computing circuit 540d for computing the maximum value of the image pickup signal stored in the frame memory 540i, that is, an area of the saturated region, and an area judging circuit 540e for comparing a predetermined value with an area of the maximum-value range computed by the maximum-value range area computing circuit 540d to output a signal as a spot-light detecting signal in a case where the area of the maximum-value region is smaller than a predetermined value.

In this manner, the endoscope apparatus 560 for three dimensional measurement, according to the twenty-seventh embodiment, is provided with the halation/-measuring-light spot separation circuit 540 arranged as described above, which produces in separation the image pickup signal due to the measuring light from the image pickup signal from the CCD 532. Accordingly, it is ensured that the endoscope apparatus 560 can execute three dimensional measurement due to the measuring light without being influenced upon by the halation and the like even under observation due to the illuminating light.

An endoscope apparatus for three dimensional measurement, according to a twenty-eighth embodiment of the invention will next be described.

The endoscope apparatus for three dimensional measurement, according to the twenty-eighth embodiment, is substantially the same as that of the twenty-sixth embodiment. Accordingly, only a different arrangement is described. The same or identical reference numerals are applied to the same or identical elements and components, and the description thereof will be omitted.

Figure 57:
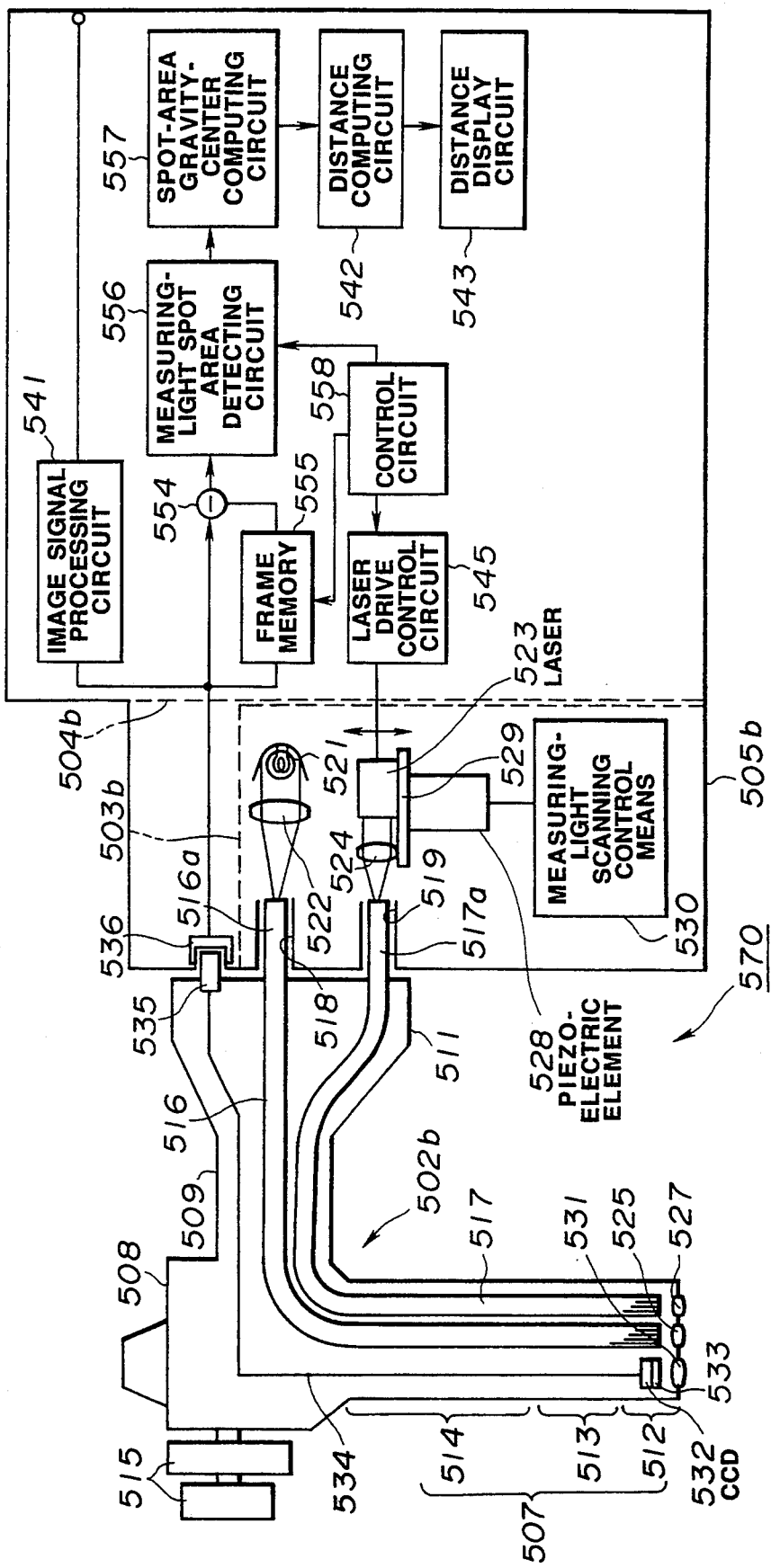
FIG. 57 is a view showing an entire arrangement of an endoscope apparatus for three dimensional measurement according to a twenty-eighth embodiment of the invention.

As shown in FIG. 57, an endoscope apparatus 570 for three dimensional measurement is so arranged as to condense a white illuminating light irradiated from a lamp 521 by a condenser lens 522 to supply an illuminating light directly to a light guide connector 516a, in ordinary illuminating-light supply means and measuring-light light-source means 503b. Further, in an electronic scope 502b, a mosaic color filter 533, for example, is mounted in front of an imaging surface of a CCD 532 for image-picking up a subject by the illuminating light, in the electronic scope 502b, to execute color separation optically.

In signal processing means 504b, an image pickup signal from the CCD 532 is inputted to an image signal processing circuit 541 for generating an image-signal, and a frame memory 555 for storing therein the image pickup signal. The image-signal processing circuit 541 generates an image signal from the image pickup signal, and outputs the image signal to a monitor (not shown). Furthermore, the frame memory 555 controls a laser drive control circuit 545, for example, by a control circuit 558, thereby storing therein an image pickup signal of only the illuminating light when the measuring light is not irradiated, and subtracts the image pickup signal stored in the frame memory 555 from the image pickup signal consisting of the illuminating light and the measuring light when the measuring light is irradiated in the subsequent step, by a subtracter 554, thereby removing affection or influence of halation and the like, similarly to the twenty-seventh embodiment.

An output from the subtracter 554 is inputted to a measuring-light spot region detecting circuit 556 as a spot light signal. Generally, there is a case where the spot of the measuring light has an extension or spreading to a certain degree, and the measuring-light spot region detecting circuit 556 measures a region of the measuring-light spot. Here, control of the measuring-light spot region detecting circuit 556 is executed by the control circuit 558.

An output from the measuring-light spot region detecting circuit 556 finds the center of gravity of the region on the basis of an optical strength distribution and the like of the region of the detected measuring-light spot, thereby being inputted to a spot region gravity-center computing circuit 557 for defining the measuring point, and inputs the measuring point defined by the spot region gravity-center computing circuit 558 to a distance computing circuit 542, to execute three dimensional measurement.

In connection with the above, the center of gravity by the region of the measuring spot has been found from the light strength distribution or the like for defining the measuring point. However, the twenty-eighth embodiment should not be limited to this specific arrangement. The arrangement may be such that a geometrical center of the region of the measuring spot is simply found so that a center thereof is brought to a measuring point.

In this manner, the endoscope apparatus 570 for three dimensional measurement, according to the twenty-eighth embodiment is so arranged as to obtain in separation the image pickup signal due to the measuring light on the basis of the image pickup signal from the CCD 532, similarly to the twenty-sixth embodiment. Accordingly, it is possible to prevent the effects from halation or the like also under observation due to the illuminating light. The center of gravity of the region of the spot having extension is found to define the measuring point with respect also to the spot having extension, whereby it is possible to execute three dimensional measurement easily and exactly.

Other arrangements, functions and advantages are the same as those of the twenty-sixth embodiment.

An endoscope apparatus for three dimensional measurement, according to a twenty-ninth embodiment of the invention, will next be described.

As shown in FIG. 58, an endoscope apparatus 601 for three dimensional measurement, according to the twenty-ninth embodiment, comprises an electronic scope 602 building therein image pickup means, a light-source.processing unit 605 building therein ordinary illuminating light supply means and measuring-light light source means 603 for supplying an ordinary illuminating light to the electronic scope 602 and signal processing means 604 for executing signal processing and distance computing, and a color monitor 606 for displaying a standard image signal generated in signal processing by the signal processing means 604.

The electronic scope 602 has an inserting section 607 which is elongated and which has elasticity so as to be insertable in a body cavity or the like, an operating section 608 having great width and which is connected to a rearward end of the inserting section 607, and a universal cable 609 extending from a side of the operating section 608. An overall connector 611 mounted on an end of the universal cable 609 can detachably be connected to the light-source.processing unit 605.

The inserting section 607 has, from its forward end, a hard forward end portion 612, a curving portion 613 capable of being curved, and a flexible tube portion 614 having flexibility. A pair of curving knobs 615 mounted on a side surface of the operating section 608 are operated whereby the curving portion 613 can be curved.

A light guide 616 for transmitting an ordinary illuminating light, and an image guide 617 serving as measuring-light transmitting means for transmitting the measuring light are inserted in the inserting section 607. The light guide 616 and the image guide 617 are inserted also In the universal cable 609. A light guide connector 616a and an image guide connector 617a at respective ends are integrally fixed to each other by the overall connector 611.

The light-source.processing unit 605 is provided with a light guide connector receptor 618 and an image guide connector receptor 619 to which the light guide connector 616a and the image guide connector 617a can detachably connected, respectively. A lamp 621 for generating a white light to a location in rear of the light guide connector receptor 618, and a condenser lens 622 are arranged within the light-source.processing unit 605. The arrangement is such that the white illuminating light from the lamp 621 can be condensed by the lens 622 so as to be supplied to the light guide connector 616a.

Moreover, a semiconductor laser 623 for generating a laser light and a condenser lens 624 are arranged at a location in rear of the image guide connector receptor 619. A condensable laser light due to the semiconductor laser 623, that is, a measuring light is condensed by the condenser lens 624, and a measuring light executing scanning in a straight-line manner as shown, for example, in FIG. 60(a) is irradiated to an end surface of the fiber bundle which forms the image guide connector 617a.

The illuminating light supplied to the light guide connector 616a is transmitted by the light guide 616, and is emanated toward a subject 626 further through an illuminating lens 625 from the end surface adjacent to the outgoing side fixed to the forward end portion 612, to illuminate a location adjacent to the subject 626 in a wide area manner. The illuminating lens 625 is mounted at a distance different from a focal distance of the illuminating lens 625 from the end surface of the light guide 616 adjacent to the outgoing side.

Furthermore, the measuring light irradiated to the image guide connector 617a is transmitted by fibers through which the measuring light in the image guide 617 is irradiated, and is further emanated toward the subject 626 through a projecting (light projecting) lens 627 from the end surface adjacent the outgoing side fixed to the forward end portion 612, thereby forming a minute optical spot on the surface of the subject 626. The projecting lens 627 is mounted at a focal distance of the projecting lens 627 from the end surface of the image guide 617 adjacent the outgoing side. The measuring light emanating from the fibers at the end surface adjacent to the outgoing side can form a minute optical spot on a surface of the subject 626, without substantial extension or spreading.

The semiconductor laser 623 and the condenser lens 624 are mounted on a table 629 which is driven by a piezo-electric element 628 in a vibratory manner. A drive signal is applied to the piezo-electric element 628 from measuring-light scanning control means 630, whereby the piezo-electric element 628 is vibrated vertically as indicated by an arrow, for example, in FIG. 58. By the vibratory movement in the vertical direction, the semiconductor laser 623 is similarly caused to vibrate. Thus, the measuring light executes scanning toward the subject 626 through the projecting lens 627 in a straight-line manner.

The piezo-electric element 628 is driven by a drive signal in the form of a stepwise wave, for example, from the measuring-light scanning control means 630. By this driving, the measuring light irradiated to the fiber bundle of the image guide connector 617a is irradiated successively every fibers spaced constant or predetermined intervals away from each other, to scan the range of substantially the diameter of the fiber bundle in a stepwise manner and in a straight-line manner, as shown in FIG. 60(a).

The subject 626 illuminated by the illuminating light in a wide area manner is imaged on an image pickup surface of a CCD 632 serving as an image pickup element arranged at a focal surface of an objective lens 631 by The objective lens 631 which is mounted on an observing window in the forward end portion 612.

A mosaic color filter 633, for example, is mounted in front of the image pickup surface, to execute color separation optically. The CCD 632 is connected to a signal connector 635 of the connector 611 through a signal cable 634, and is connected to an image circuit 641, a distance computing circuit 642 and a peak hold circuit 644 through a signal connector receptor 636 to which the signal connector 635 is connected. The image circuit 641 is so arranged as to generate a standard image signal on the basis of the image pickup signal from the CCD 632, to output the image signal to the monitor 606. Furthermore, the distance computing circuit 642 is as arranged as to compute a distance from the image pickup signal due to the measuring light to the subject 626, to output a value of the distance to a distance display circuit 643. Thus, the distance can be displayed by the distance display circuit 643.

The peak hold circuit 644 holds a peak value of the image pickup signal from the CCD 632. The held peak value is compared with a predetermined reference voltage 646 by a comparator circuit 645. In a case where the peak value of the image pickup signal from the CCD 632 is smaller than the reference voltage 646, that is, in a case where the reflecting light from the subject 626 with respect to the measuring light is small, counting is executed by a counter 647. If a predetermined counting value is reached, error information such as, for example, "measurement incapability" and the like is displayed on the distance display circuit 643.

Moreover, the signal processing means 604 is provided with a control circuit 648 which resets the peak hold circuit 644 and the counter 647, and which stops scanning of the measuring-light scanning control means 630 and light emission of the semiconductor laser 623 when the counter 647 reaches a predetermined count number.

In the present embodiment, the objective lens 631 and the projecting lens 627 are arranged on the forward end portion 612 in adjacent relation to each other as illustrated in FIG. 59, for example. The illuminating lens 625 is provided on either one or both sides thereof as indicated by a broken line.

Further, the present embodiment is arranged as follows. That is, as shown in FIG. 58, in a case where the table 629 is vibrated vertically, the laser light scans the fiber bundle vertically at a location adjacent to the incident end surface of the image guide 617. By the scanning, adjacent to the outgoing end surface, the scanning corresponds to a state or condition in FIG. 58 in which scanning is executed horizontally. The measuring light projected toward the subject 626 through the projecting lens 627 is emanated radially by the projecting lens 627 in a plane m including the optical axis of the objective lens 631 and the optical axis of the projecting lens 627, as shown in FIG. 59.

In the endoscope apparatus 601 for three dimensional measurement, arranged in this manner, the table 629 is scanned in a stepwise manner as described above. Accordingly, in a case where the surface of the subject 626 is planar, for example, and the measuring light is scanned under a condition in which the end surface of the forward end portion 612 is confronted against the surface vertically, spot rows s having almost constant intervals appear correspondingly to the stepwise scanning as shown in FIG. 60(b), on the image pickup surface of the CCD 632. The intervals of the spot rows s vary depending upon the distance between the forward end surface of the scope 602 and the subject 626. Thus, it is possible to compute the distance of the actual spot on the basis of the principle of triangulation. The numbers of spot rows s or the pitches of the stepwise wave are set within the numbers or equal to or above the pitches capable of recognizing in separation the spots from the output signal from the CCD 632 during a period of time of one field or one frame.

On the other hand, in a case where the surface of the subject 626 is irregular, spot rows having no constant intervals appear in a straight-line manner in accordance with the irregular surface. Also in this case, it is possible to compute the distance to the spot position actually formed on the surface of the subject 626, by the use of the principle of triangulation from the positional information of the spots on the CCD 632. The distance computing circuit 642 executes computation of the distance.

The principle on the basis of which the spot position (X, Y, Z) is found in a case where scanning is made in a plane in which the optical axis of the projecting lens 627 and the optical axis of the objective lens 631 are connected to each other is the same as that in FIG. 16 of the ninth embodiment and, accordingly, the description thereof will be omitted.

In connection with the above, since the spots on the surface of the subject 626 in a portion where the amount of irregularity is large are piled up upon each other, the magnitude or size of the pitches of the stepwise wave can be set variably in accordance with a using condition or state of affairs. The distance computing circuit 642 separates in color the output signal from the CCD 632, extracts, for example, a signal component of the wavelength of the laser light, and subtracts an envelope detection signal or a low-pass signal of the signal component from the signal component to detect the spot, thereby finding the spot position on the surface of the CCD 632.

Further, the peak hold circuit 644 holds a peak value of the image pickup signal from the CCD 632. The held peak value is compared with predetermined reference voltage 646 by the comparator circuit 645. In a case where the peak value of the image pickup signal from the CCD 632 is smaller than the reference voltage 646, that is, in a case where the reflecting light from the subject 626 is small with respect to the measuring light, counting is executed by the counter 647. When a predetermined counting number is reached, error information such as, for example, "measurement incapability or the like" is displayed on the distance display circuit 643. The control circuit 648 resets the peak hold circuit 644 and the counter 647. When the counter 647 reaches a predetermined number of counting, both the scanning of the measuring-light scanning control means 630 and light emission of the semiconductor laser 623 are stopped.

Accordingly, the endoscope apparatus 601 for three dimensional measurement, according to the twenty-ninth embodiment, is arranged as follows. That is, in a case where the reflecting light from the subject 626 with respect to the measuring light is small so that the measurement errors increase, and distance measurement is impossible, error information is displayed on the distance display circuit 643. Scanning of the measuring-light scanning control means 630 and light emission of the semiconductor laser 623 are stopped by the control circuit 648. An operator is quickly informed that three dimensional measurement is impossible. Measurement is halted. Accordingly, the operator executes adjustment or regulation, alteration or changing, or the like, of a measuring system, whereby it is possible to execute reliably and efficiently three dimensional measurement by the projected measurement system by which a desirable measuring strength if produced.

An endoscope apparatus for three dimensional measurement, according to a thirtieth embodiment of the invention will next be described.

The endoscope apparatus for three dimensional measurement, according to the thirtieth embodiment, is substantially the same as that according to the twenty-ninth embodiment, only a different arrangement will be described. The same or identical reference numerals are applied to the same or identical components and parts, and the description thereof will be omitted.

Figure 61:
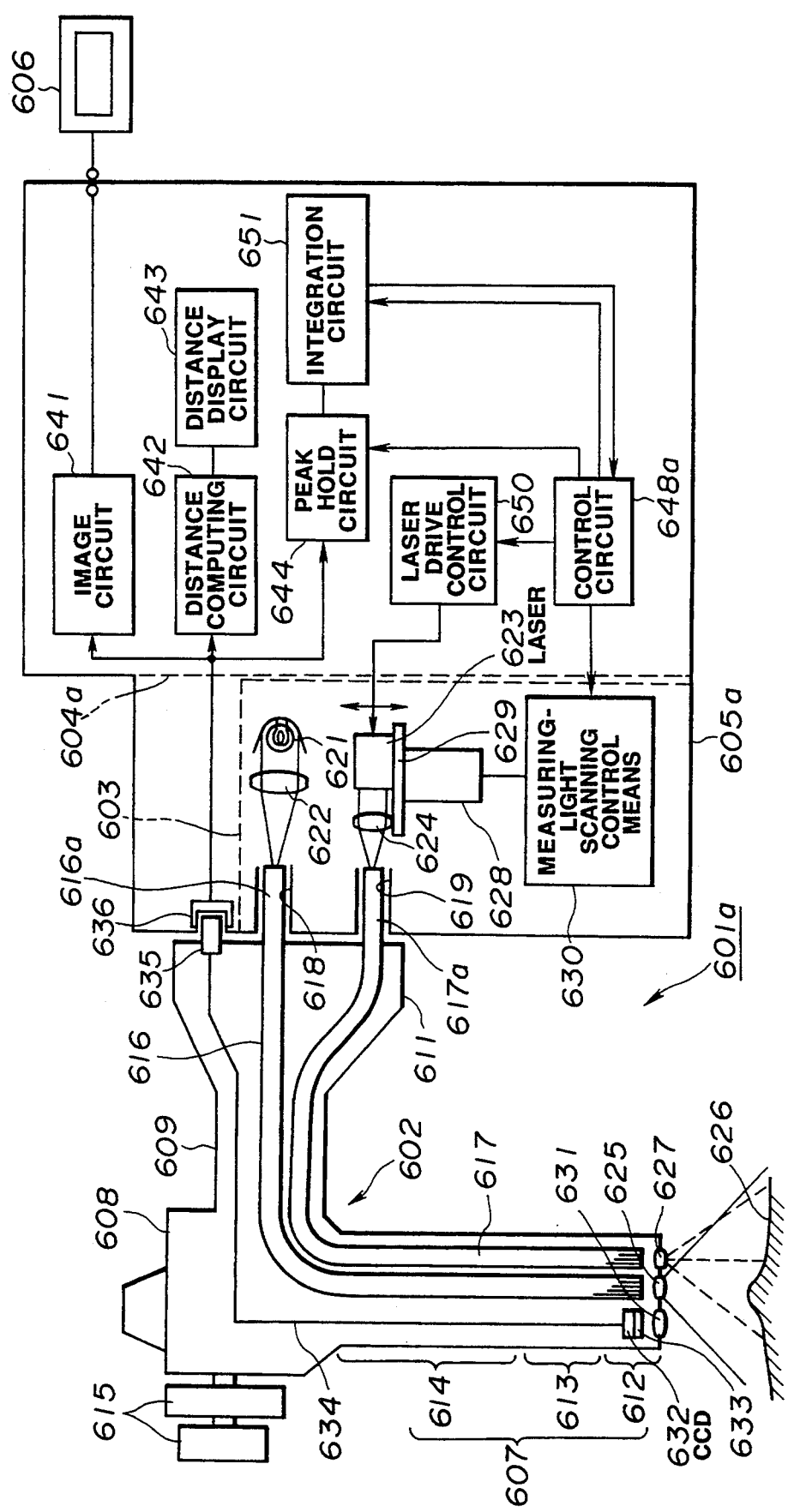
FIG. 61 is a view showing an entire arrangement of an endoscope apparatus for three dimensional measurement according to thirtieth embodiment of the invention.

As shown in FIG. 61, in an endoscope apparatus 601a for three dimensional measurement, according to the thirtieth embodiment, signal processing means 604a of a light-source.processing unit 605a comprises an integrating circuit 651 for integrating a peak value of an image pickup signal from a CCD 632 held by a peak hold circuit 644, a laser drive control circuit 650 for controlling an irradiation strength of a semiconductor laser, and a control circuit 648a for controlling the laser drive control circuit 650 and measuring-light scanning control means 630 on the basis of a value of the integrating circuit 651.

Other arrangements are the same as that of the twenty-ninth embodiment.

In the endoscope apparatus 601a for three dimensional measurement, arranged in this manner, peak values of the image pickup signals of the spots from the CCD 632 are integrated by the integrating circuit 651. The control circuit 648a controls the measuring-light scanning control means 630 in a case where the integrated value is smaller than the predetermined value or larger than the same, to irradiate the illuminating light to the fiber end surfaces corresponding respectively to the falling-under spot positions. The control circuit 648a controls the irradiation strength of the measuring light to obtain a proper or adequate measuring strength with respect to the laser drive control circuit 650. Further, in a case where an adequate measuring strength is not obtained by the laser drive control circuit 650 so that measurement is incapable of being executed, error information is displayed by a distance display circuit 643, similarly to the twenty-eighth embodiment, and scanning of the measuring-light scanning control means 630 and light emission of the semiconductor laser 623 are stopped.

Other functions are the same as that of the twenty-ninth embodiment.

Accordingly, the endoscope apparatus 601a for three dimensional measurement, according to the thirtieth embodiment, can produce a predetermined measuring strength in addition to the advantages of the twenty-ninth embodiment by the fact that, even in a case where the reflecting light from the subject 626 with respect to the measuring light is out of the range of the predetermined strength so that an error occurs in measurement, the illuminating strength of the measuring light is controlled.

An endoscope apparatus for three dimensional measurement, according to a thirty-first embodiment of the invention will next be described.

The endoscope apparatus for three dimensional measurement, according to the thirty-first embodiment, is substantially the same as that according to the twenty-ninth embodiment and, accordingly, only a different arrangement will be described. The same or identical reference numerals are applied to the same or identical arrangements and parts, and the description thereof will be omitted.

Figure 62:
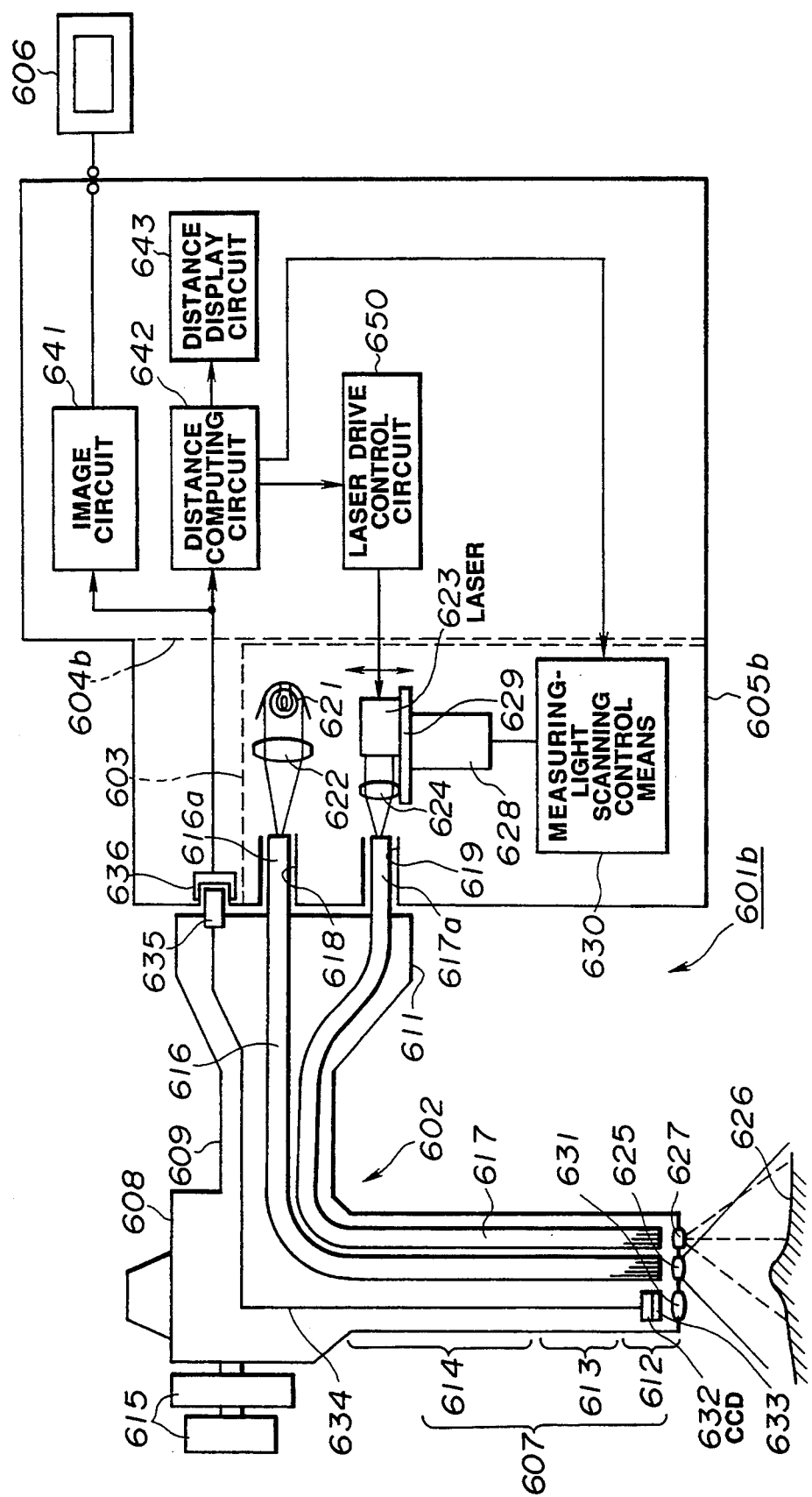
FIG. 62 is a view showing an entire arrangement of an endoscope apparatus for three dimensional measurement according to a thirty-first embodiment of the invention.

As shown in FIG. 62, an endoscope apparatus 601b for three dimensional measurement, according to the thirty-first embodiment, comprises a light-source.processing unit 605b whose signal processing means 604b has an image circuit 641, a distance computing circuit 642 and a distance display circuit 643, and a laser drive control circuit 650 for controlling an irradiating strength of a semiconductor laser 623 in accordance with a distance computed by the distance computing circuit 642. In a case where an adequate measuring strength is not produced by the laser drive control circuit 650 so that measurement is impossible, error information is displayed by the distance display circuit 643 similarly to the twenty-ninth embodiment, and scanning of a measuring-light scanning control means 630 and light emission of the semiconductor laser 623 are stopped. Other arrangements and functions are the same as those of the twenty-ninth embodiment.

The endoscope apparatus 601b for three dimensional measurement, according to the thirty-first embodiment, arranged in this manner, can control the irradiation strength of the semiconductor laser 623 in accordance with the distance computed by the distance computing circuit 642, in addition to the advantages of the twenty-ninth embodiment. Accordingly, three dimensional measurement can be executed always under the predetermined measuring strength.

An endoscope apparatus for three dimensional measurement, according to a thirty-second embodiment of the invention, will next be described.

Figure 63:
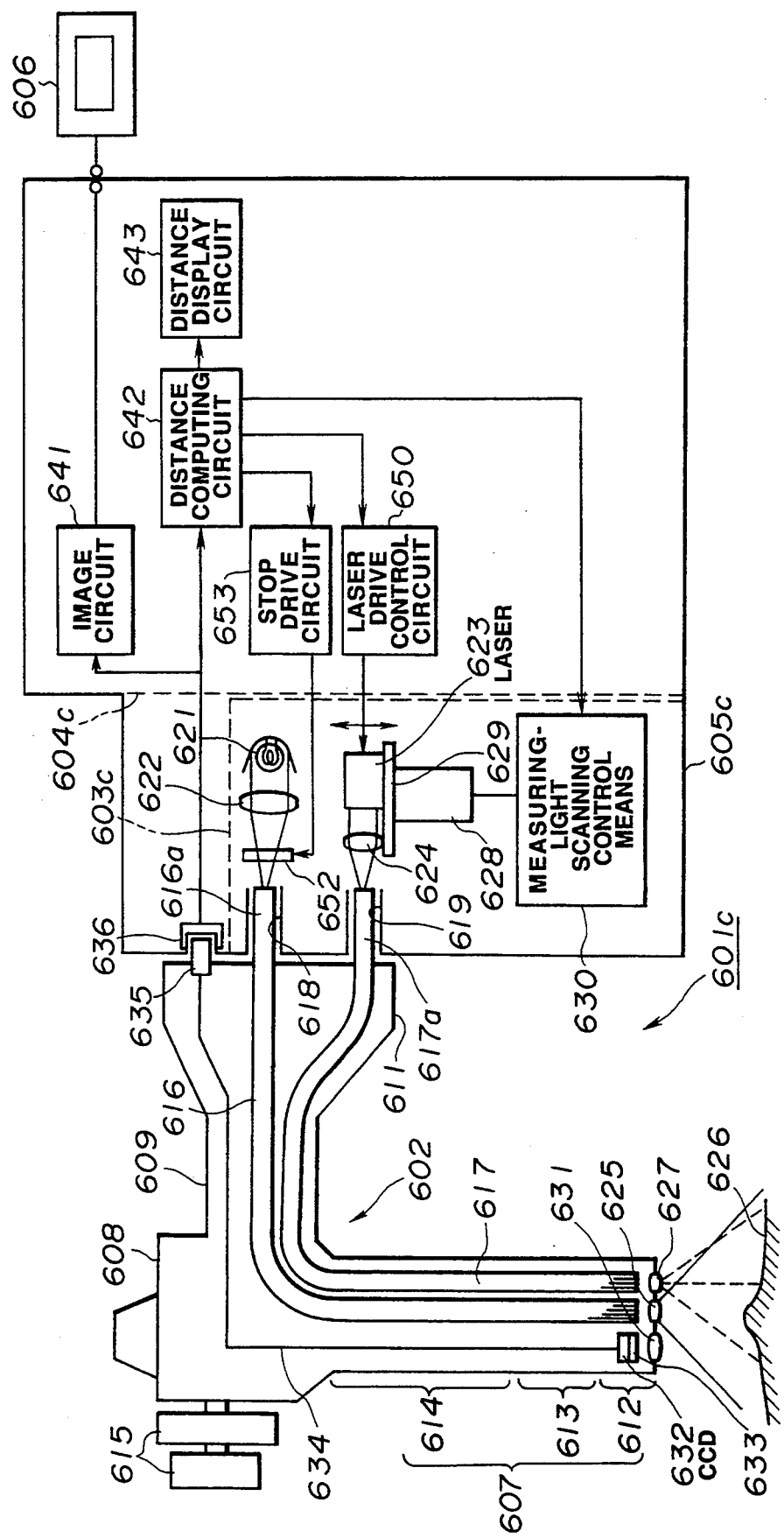
FIG. 63 is a view showing an entire arrangement of an endoscope apparatus for three dimensional measurement according to a thirty-second embodiment of the invention.

As shown in FIG. 63, an endoscope apparatus 601c for three dimensional measurement, according to the thirty-second embodiment, is substantially the same as that according to the thirty-first embodiment. Specifically, measuring-light light source means 603c of a light-source.processing unit 605c is provided with a stop or iris unit 652 for controlling a quantity of incident light of a white illuminating light from a lamp 621 which is incident upon an end surface of a light guide connector 616a, at a location between a condenser lens 622 and the light guide connector 616a. Signal processing means 604c is provided with an iris drive circuit 653 for controlling an iris quantity of the iris unit 652, in accordance with a distance computed by a distance computing circuit 642. Other arrangements are the same as that of the thirty-first embodiment.

The endoscope apparatus 601c for three dimensional measurement, according to the thirty-second embodiment, arranged in this manner, has advantages that, since the iris quantity of the iris unit 652 is controlled in accordance with the distance by the iris drive circuit 653, a subject 626 can be observed always under an adequate illuminating light, in addition to advantages of the thirtieth embodiment.

An endoscope apparatus for three dimensional measurement according to a thirty-third embodiment of the invention will next be described.

Figure 64:
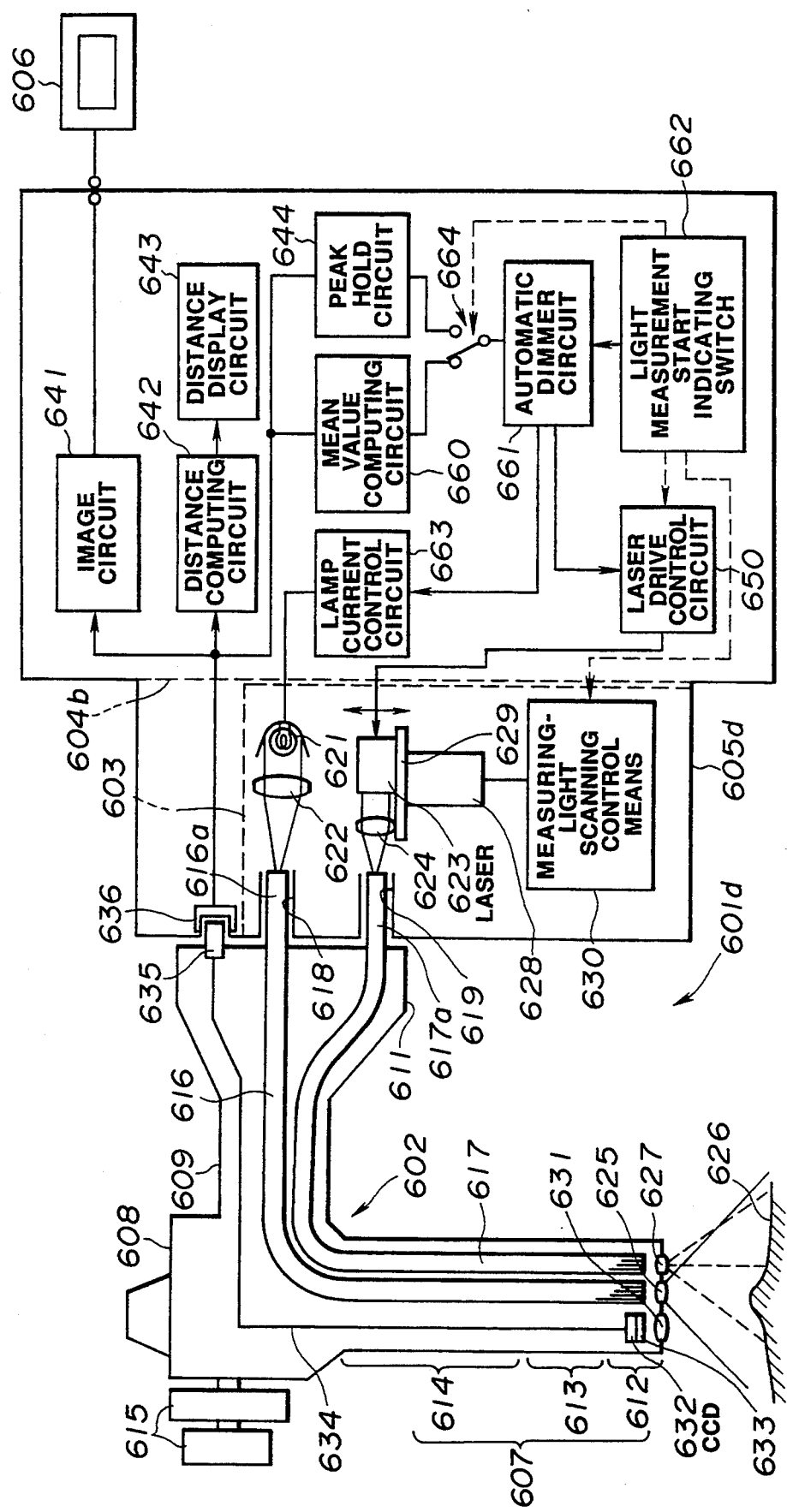
FIG. 64 is a view showing an entire arrangement of an endoscope apparatus for three dimensional measurement according to a thirty-third embodiment of the invention.

As shown in FIG. 64, an endoscope apparatus 601d for three dimensional measurement, according to the thirty-third embodiment, is substantially the same as that of the thirty-first embodiment. Specifically, in the endoscope apparatus 601d for three dimensional measurement, according to the thirty-third embodiment, a light-source.processing unit 605d is provided with a lamp-current control circuit 663 for controlling lamp current passing through a lamp 621, a mean-value computing circuit 660 for computing a mean value of a quantity of illuminating light at observation, from an image pickup signal from a CCD 632, an automatic dimmer circuit 661 for controlling the lamp-current control circuit 663 so that a predetermined quantity of illuminating light is produced on the basis of a mean value of the quantity of illuminating light from the mean-value computing circuit 660, a peak hold circuit 644 for holding a peak value of the image pickup signal from the CCD 632, a change-over switch (hereinafter simply referred to as "SW") 664 for changing over the mean-value computing circuit 660, a laser drive control circuit 650 for controlling an irradiating strength of a semiconductor laser 623, and a light-measurement start indication SW 662 for issuing a light-measurement start indication to the automatic dimmer circuit 661 and the change-over SW 664. When the automatic dimmer circuit 661 receives a measurement start indication from the light-measurement start indicating SW 662, the automatic dimmer circuit 661 has inputted thereinto a mean value of an observing light computed by the mean-value computing circuit 660 through the change-over SW 664. The automatic dimmer circuit 661 controls the laser drive control circuit 650 on the basis of the peak value, to control the irradiation strength of the measuring light so as to produce an adequate measuring strength. In this connection, control of the laser drive control circuit 650 at the automatic dimmer circuit 661 may be executed by the use of the comparator as indicated in the twenty-ninth embodiment, for example, or by the use of the integrator, as shown in the thirtieth embodiment.

Other arrangements are the same as that of the thirty-first embodiment.

The endoscope apparatus 601d for three dimensional measurement, according to the thirty-third embodiment, arranged in this manner, has advantages that, since the lamp current passing through the lamp 621 is controlled on the basis of the mean value of the quantity of illuminating light so as to produce the predetermined quantity of illuminating light, at observation, by the mean-value computing circuit 660 and the automatic dimmer circuit 661, a subject 626 can be observed always under the adequate illuminating light, in addition to the advantages of the thirty-first embodiment.

An endoscope apparatus for three dimensional measurement, according to a thirty-fourth embodiment of the invention, will next be described.

Figure 65:
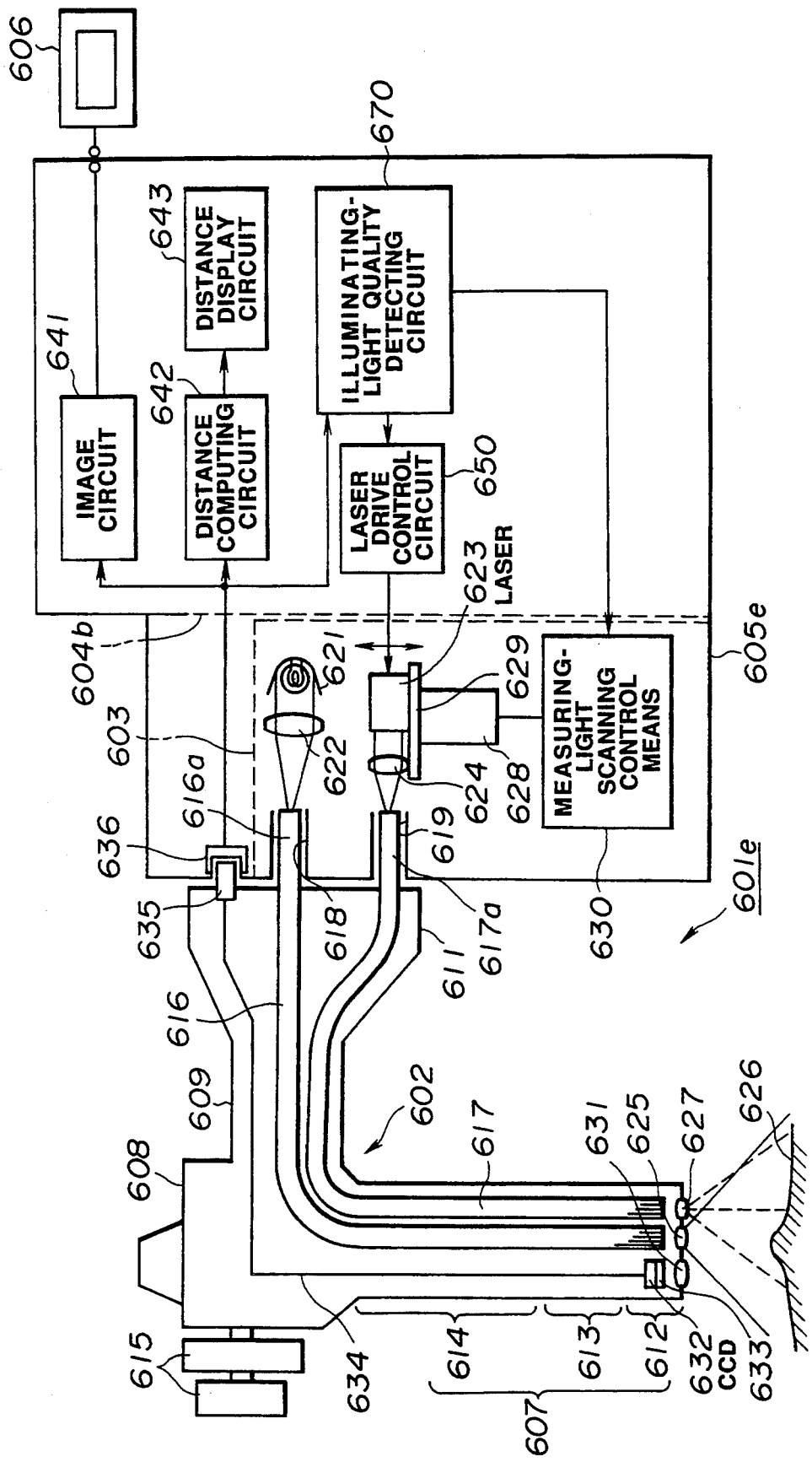
FIG. 65 is a view showing an entire arrangement of an endoscope apparatus for three dimensional measurement according to a thirty-fourth embodiment of the invention.

As shown in FIG. 65, an endoscope apparatus 601e for three dimensional measurement, according to the thirty-fourth embodiment, is substantially the same as that of the thirty-first embodiment. Specifically, the thirty-fourth embodiment comprises an illuminating-light quantity detecting circuit 670 for, for example, integrating an image pickup image for a constant or predetermined period of time to detect a quantity of illuminating light, thereby controlling a laser drive control circuit 650 on the basis of the detected quantity of illuminating light. Other arrangements are the same as the thirty-first embodiment.

In a case where a distance between the image pickup means and the subject 626 is long, a light quantity reflected from the subject 626 decreases. Accordingly, an image pickup signal produced by a CCD 633 that is the image pickup means is small so that its integrating value becomes also small. In this case, in the endoscope apparatus for three dimensional measurement, according to the thirty-fourth embodiment, the illuminating-light quantity detecting circuit 670 integrates the image pickup signal from the CCD 633 for a predetermined period of time to detect the quantity of illuminating light. Since the laser drive control circuit 650 controls a semiconductor laser 623 so as to strengthen the irradiation strength thereof, on the basis of the detected quantity of illuminating light, it is possible to stably maintain accuracy of the three dimensional measurement due to the laser light.

Moreover, in the reverse situation where a distance between the image pickup means and the subject is short, the illuminating-light quantity detecting circuit 670 integrates the image pickup signal from the CCD 633 for a predetermined period of time to detect the quantity of illuminating light. Since the laser drive control circuit 650 controls the irradiation strength of the semiconductor laser 623 to weaken the same, on the basis of the detected quantity of illuminating light, it is similarly possible to maintain the accuracy of the three dimensional measurement stably due to the laser light.

An endoscope apparatus for three dimensional measurement, according to a thirty-fifth embodiment of the invention, will next be described.

Figure 66:
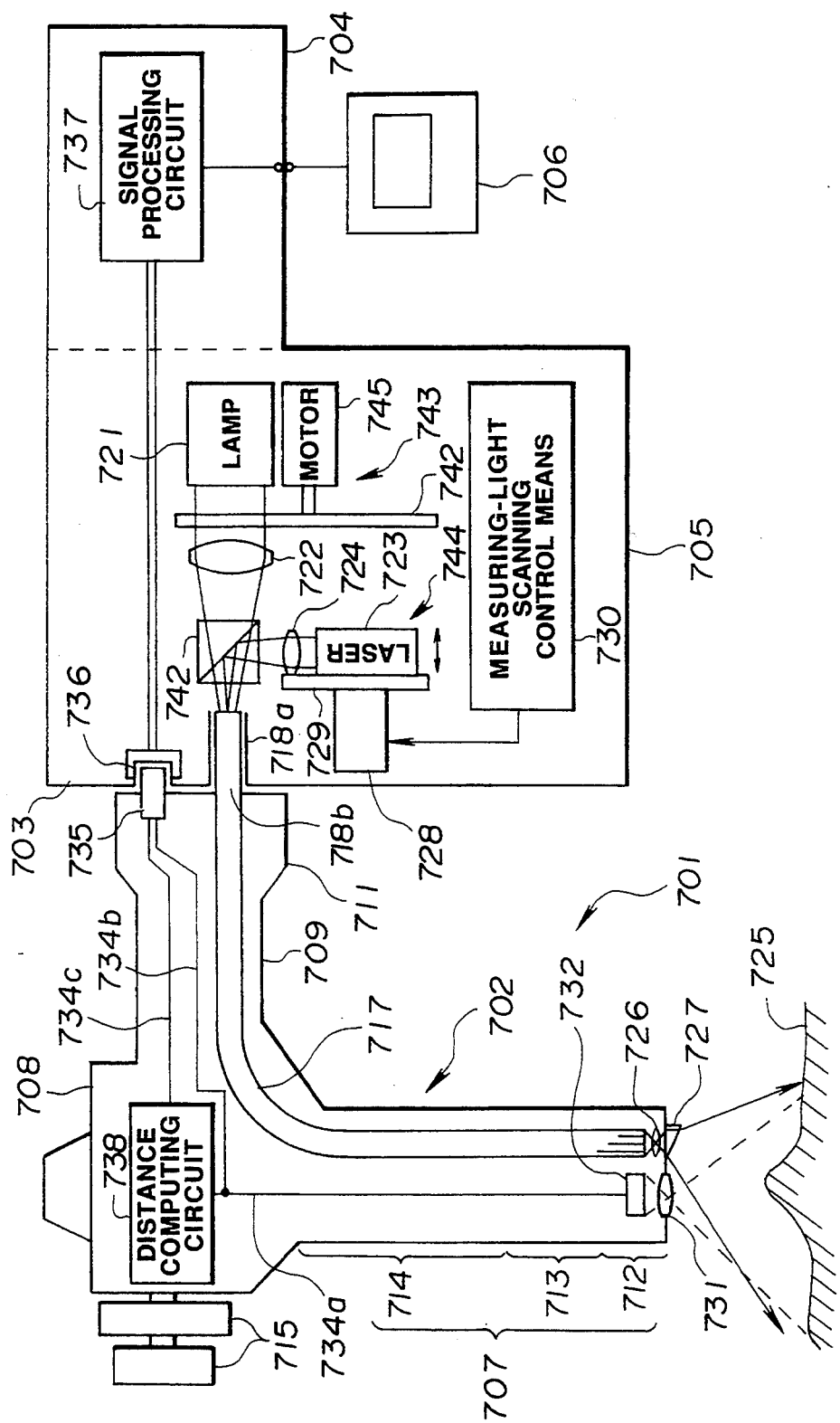

As shown in FIG. 66, an endoscope apparatus 701 for three dimensional measurement, according to the thirty-fifth embodiment, comprises an electronic scope 702 building therein image pickup means, a light-source.processing unit 705 building therein ordinary illuminating-light/measuring-light light source means 703 for supply an ordinary illuminating light to the electronic scope 702 and signal processing means 704 for executing signal processing, and a color monitor 706 for displaying a standard image signal generated in signal processing by the signal processing means 704.

The electronic scope 702 has an inserting section 707 which is elongated and which has flexibility so as to be capable of being inserted into a body cavity or the like, an operating section 708 which has a great width and which is connected to a rearward end of the inserting section 707, and a universal cable 709 extending from a side of the operating section 708. An overall connector 711 mounted on an end of the universal cable 709 can detachably be connected to the light-source.processing unit 705.

The inserting section 707 has, from its forward end, a hard forward end portion 712, a curving portion 713 capable of being curved, and a flexible tube portion 714 having flexibility. A pair of curved knobs 715 mounted on the side surface of the operating section 708 are operated whereby the curving portion 713 can be curved.

An image guide 717 serving as ordinary illuminating-light/measuring-light transmitting means for transmitting an ordinary illuminating light and a measuring light is inserted in the inserting section 707. The image guide 717 is inserted also into the universal cable 709, and an image guide connector 718b at an end thereof is integrally fixed by the overall connector 711.

The light-source.processing unit 705 is provided with an image guide connector receptor 718a to which the image guide connector 718b can detachably be connected. Furthermore, a half prism 742 is arranged within the light-source.processing unit 705 to be opposed against the image guide connector receptor 718a. Ordinary illuminating-light generating means 743 is arranged in opposed relation to one of a pair of branching surfaces of the half prism 742. Measuring-light generating mans 744 is arranged in opposed relation to the other branching surface.

A white illuminating light from a lamp 721 is irradiated to an RGB rotary disc 746, for example, serving as the ordinary illuminating-light generating means 748, rotatively driven by a motor 745. An RGB light generated through the RGB rotary disc 746 is condensed by a condenser lens 722 and is incident upon the one branching surface of the half prism 742. The RGB light is transmitted through the half prism 742 and is supplied to the image guide connector 718b.

Moreover, a semiconductor laser 728 for generating a laser light and a condenser lens 724, serving as the measuring-light generating means 744, are arranged in rear of the image guide connector receptor 718a. A laser light capable of being condensed, due to the semiconductor laser 728, that is, a measuring light is condensed by the condenser lens 724, is further reflected by the hold prism 742, and irradiates a measuring light which scans, in a linear or straight-line manner, an end surface of the fiber bundle forming the image guide connector 718b.

The illuminating light and the measuring light supplied to the image guide connector 718b are transmitted by the image guide 717, and are emanated further from the end surface fixed to the forward end portion 712, adjacent to the outgoing side, toward a subject 715 through a projecting lens 726 and a prism 727, to illuminate a location adjacent to a subject 725 in a wide area manner. The prism 727 is formed to widen an irradiating angle of the illuminating light and the measuring light so that the measuring light can be irradiated over an entire image pickup area of a CCD 732 serving as the image pickup element to be described subsequently. Moreover, the projecting lens 726 is mounted at a focal distance of the projecting lens 726 from the end surface of the image guide 717 adjacent to the outgoing side. In a case where the measuring light emanated from the fibers of the end surface adjacent to the outgoing side, the optical beam can form a minute optical spot on the surface of the subject 725 without being subject to substantial spreading.

The semiconductor laser 723 and the condenser lens 724 are mounted on a table 729 which is driven in a vibratory manner by a piezo-electric element 728. The drive signal in the form of a stepwise wave, for example, is applied to the piezo-electric element 728 from measuring-light scanning control means 730, whereby the piezo-electric element 728 is moved in vibration laterally as indicated by, for example, an arrow in FIG. 66. By the vibratory movement in the lateral direction, the semiconductor laser 723 is also moved in vibration. The measuring light irradiated to the fiber bundle of the image guide connector 718b is successively irradiated to every fiber-spaced constant or predetermined interval from each other, and is scanned in a straight-line manner toward the subject 725 through the projecting lens 726 and the prism 727.

The subject 725 illuminated by the illuminating light in a wide area manner is imaged onto an image pickup surface of a CCD 732 serving as an image pickup element arranged at a focal surface of an objective lens 731, by the objective lens 731 mounted on an observation window in the forward end portion 712. The CCD 732 is connected to a distance computing circuit 738 through a signal cable 734a. The distance computing circuit 738 is as arranged as to compute irregularities of the subject 725 by the principle of triangulation by the measuring light. An output from the distance computing circuit 738 is connected to a signal connector 735 in the connector 711 through a signal cable 734c. Furthermore, the CCD 732 is connected directly to the signal connector 732 of the connector 711 through a signal cable 734b, and is connected to a signal processing circuit 737 through a signal connector receptor 736 to which the signal connector 735 is connected.

Figure 67:
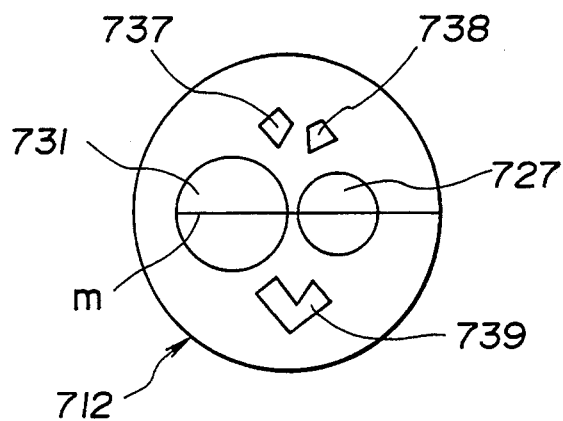

In the present embodiment, the objective lens 731 and the prism 727 are provided at the forward end portion 712, for example, as illustrated in FIG. 67 in adjacent relation to each other. One of the objective lens 731 and the prism 727 is provided with a pair of water feed ports 737 and 738, while the other is provided with a gas feed valve 739, so that the objective lens 731 and the prism 727 can be cleaned and the like.

Figure 68:
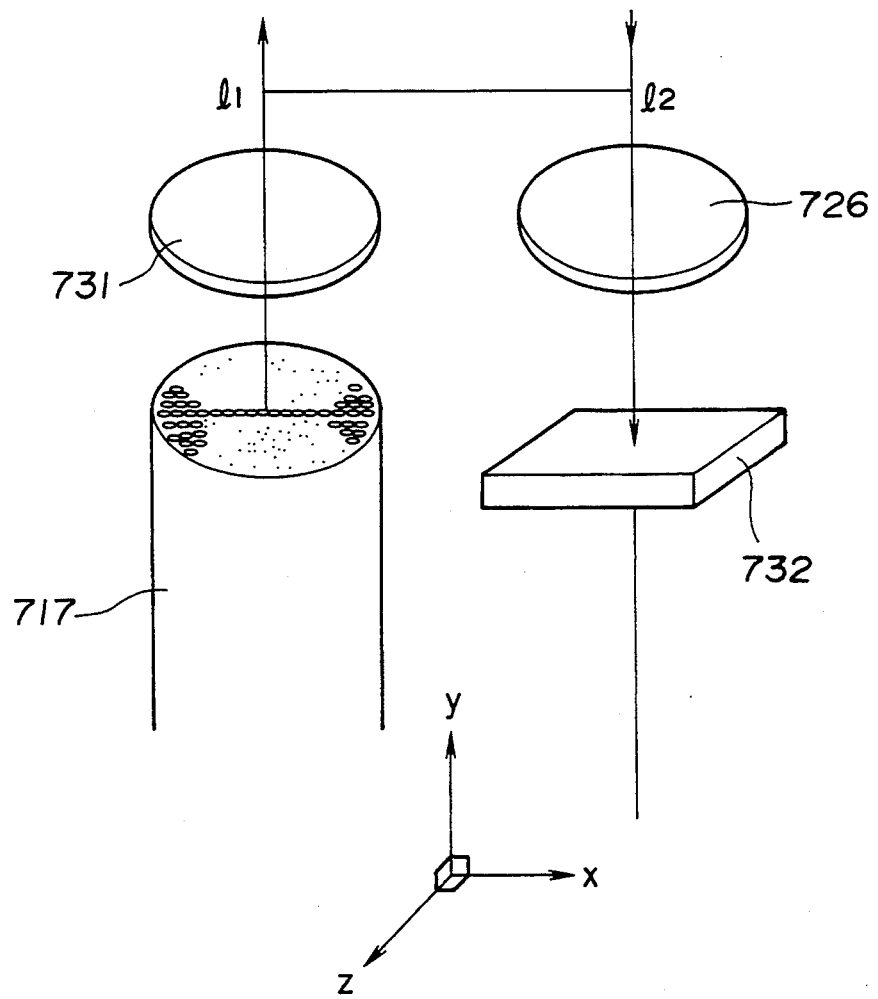

Further, in the present embodiment, as shown in FIG. 66, in a case where the table 729 is vibrated laterally, the laser light scans the fiber bundle laterally at a location adjacent to the incident end surface of the image guide 717. By this scanning, at a location adjacent to the outgoing end surface, the scanning corresponds to a condition in FIG. 66 that the laser light is scanned horizontally. The measuring light projected toward the subject 725 through the projecting lens 726 and the prism 727 is emanated radially by the projecting lens 726 in a direction of an x-axis in a plane m including the optical axis 711 of the projecting lens 726 and the optical axis 712 of the objective lens 731, for example, as illustrated in FIG. 68.

As described above, the table 729 is scanned in a stepwise manner, and the measuring light is irradiated over the entire image pickup area of the CCD 732 by the prism 727. Accordingly, as shown in FIG. 69(a), in a case where the measuring light is scanned in the plane m, and in a case, for example, where the surface of the subject 725 is planar and the measuring light is scanned under a condition that an end surface of the forward end portion 712 is confronted against the surface vertically, spot rows s having almost constant or predetermined intervals appear on the image pickup surface of the CCD 732, over the entire image pickup area, correspondingly to the stepwise scanning as shown in FIG. 69(b). The intervals of the spot rows s vary depending upon the distance between the forward end surface of the scope 702 and the subject 725. Thus, it is possible to compute an actual distance to the spot on the basis of the principle of triangulation.

The numbers of the spot rows s or pitches of the stepwise waves are set to a value equal to or more than the pitches which are recognizable in separation from the output signal from the CCD 732 by each spot during a period of time of one field or one frame.

On the other hand, in a case where the surface of the subject 725 is irregular, spot rows having no constant intervals appear in a straight-line manner in accordance with the irregular surface. Also in this case, it is possible to compute the distance to the spot position actually formed on the surface of the subject 725, by the use of the principle of triangulation, from the positional information of the spots on the CCD 732. Thus, the distance computing circuit 738 executes this computation of distance.

The principle on the basis of which a spot position (X, Y, Z) is found in a case where scanning is made in a plane connecting the optical axis of the projecting lens 726 and the optical axis of the objective lens 731 to each other is the same as that in FIG. 16 showing the ninth embodiment and, accordingly, the description thereof will be omitted.

In connection with the above, since there is a case where spots on the surface of the subject 725 are piled upon each other in a portion where an amount of irregularity is large, the magnitude or size of a pitch of the stepwise wave is so arranged as to be capable of being set variably in accordance with a using state of affairs. The distance computing circuit 738 separates in color the output signal from the CCD 732. The distance computing circuit 738 extracts a signal component of the wavelength of the laser light, for example, and subtracts an envelope detecting signal or a low-pass signal of the signal component, from the signal component to detect the spot. Thus, the spot position on the surface of the CCD 732 is found.

Furthermore, the distance computing circuit 738 further computes a distance-direction component connecting the subject 726 and the forward end surface of the scope 702 to each other, that is, the quantity of irregularity of the surface of the subject 725 in the height direction, subsequent to the computation of the distance. The distance computing circuit 738 outputs an irregular data signal to the signal processing circuit 737. The signal processing circuit 737 superimposes the irregular data signal onto the image signal representing the endoscope image, to output the superimposed signal to the monitor 706. As shown in FIG. 70, for example, the signal processing circuit 737 displays the computed irregularity data on a portion below the endoscope image display area 706a, over a scanning range h of the measuring spot in the monitor display screen.

As described above, the endoscope apparatus 701 for three dimensional measurement, according to the thirty-fifth embodiment, brings the irradiation angle of the measuring light at least to a wide angle, by the prism 727 that is wide-area irradiating means, and can irradiate the measuring light over the entire image pickup area of the CCD 732. Accordingly, the endoscope apparatus 701 for three dimensional measurement can efficiently measure the subject 725 in a three dimensional manner.

In connection with the above, it has been described that scanning of the measuring light is executed in the x-axis direction within the plane m including the optical axis 711 of the projecting lens 726 and the optical axis 712 of the objective lens 731. However, the invention should not be limited to this specific arrangement. As shown in FIG. 71(a), scanning may be executed in a z-axis direction which is perpendicularly intersected with the plane m in FIG. 68. At this time, the spot rows s as shown in FIG. 71(b) appear on the image pickup surface of the CCD 732 in the entire image pickup area. In a case where the surface of the subject 725 is irregular, spot rows s having no constant intervals appear substantially in a straight-line manner in accordance with the irregular surface. Specifically, the spot rows s can produce two dimensional information that is irregularity information in the scanning direction and irregularity information adjacent to a direction perpendicular to a scanning direction, in accordance with the surface of the subject 725.

Figures 72A, 72B:
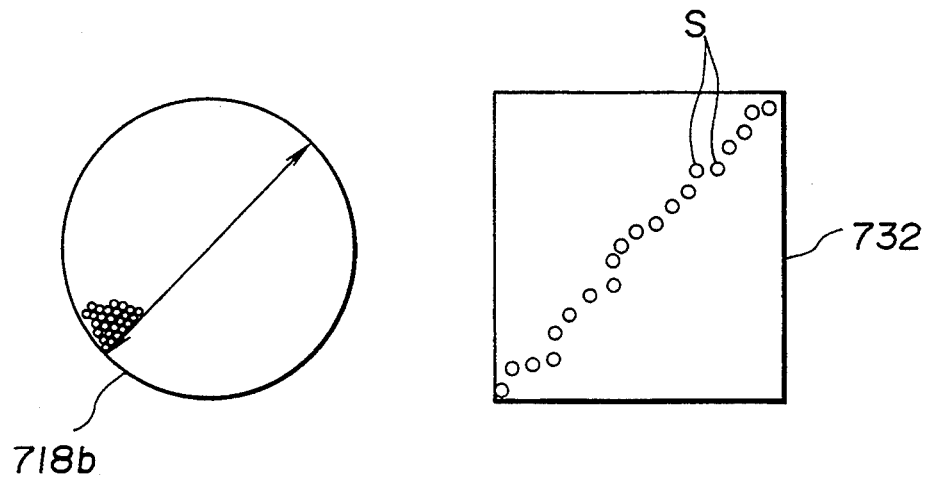

Moreover, as shown in FIG. 72(a), scanning may be executed in a straight-line direction indicated by x=z having an angle of 45°, for example, with respect to a plane y=0 extending perpendicularly to the plane m in FIG. 68. At this time, the spot rows s as shown in FIG. 72(b) appear on the image pickup surface of the CCD 732, over the entire image pickup area. In a case where the surface of the subject 725 is irregular, the spot rows s having no constant intervals appear substantially in a straight-line manner in accordance with the irregular surface. Specifically, the spot rows s can produce two dimensional information that is irregular information in the scanning direction and irregular information adjacent to a direction perpendicular to the scanning direction, in accordance with the surface of the subject 725. Here, although it has been assumed that the angle in the scanning direction is 45°, the invention should not be limited to this specific arrangement. Scanning may be executed at an optional angle in the plane y=0 extending perpendicularly to the plane m.

Further, the description has been made in which the distance computing circuit 738 is provided within the electronic scope 702, and uses the principle of triangulation to compute the distance to the spot position actually formed on the surface of the subject 725, from the positional information of the spots on the CCD 732. However, the invention should not be limited to this specific arrangement. The arrangement may be arranged such that the distance computing circuit 738 is brought to a circuit for correcting the image pickup signal of the measuring light in accordance with the electronic scope 702, and the above-described computation is executed by the signal processing circuit 737. Furthermore, the distance computing circuit 738 may be formed within the light-source processing circuit 705 as an integration with the signal processing circuit 737.

An endoscope apparatus for three dimensional measurement, according to a thirty-sixth embodiment of the invention, will next be described.

The endoscope apparatus for three dimensional measurement, according to the thirty-sixth embodiment, is substantially identical in arrangement with the thirty-fifth embodiment, and is such that the irradiation-angle wide-angle means is arranged without the use of the prism.

Figure 73:
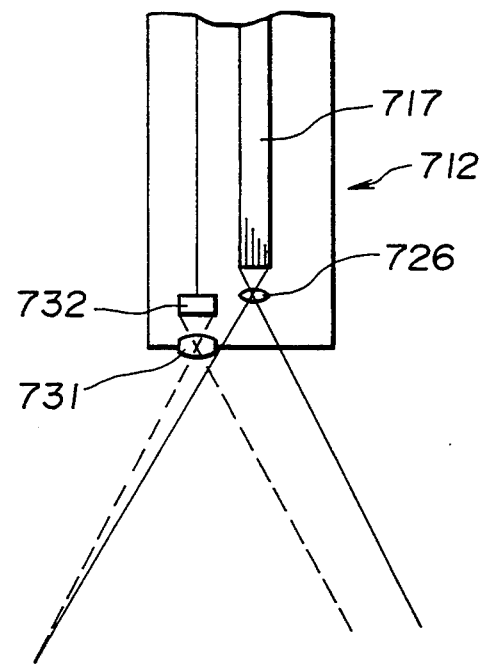
FIG. 73 is a cross-sectional view showing an arrangement of a forward end portion of an electronic scope according to a thirty-sixth embodiment of the invention.

As shown in FIG. 73, in a forward end portion 712 of an electronic scope in the thirty-sixth embodiment, an end surface of an image guide 717 and a projecting lens 726 are arranged rearwardly within the forward end portion 712 so that a measuring light can irradiate an entire image pickup area of a CCD 732 through the projecting lens 726.

Other arrangements and functions are the same as those of the thirty-fifth embodiment.

The endoscope apparatus for three dimensional measurement, according to the thirty-sixth embodiment, arranged in this manner can efficiently measure in three dimension a subject 725, because the end surface of the image guide 717 and the projecting lens 726 are arranged rearwardly within the forward end portion 712, whereby the irradiating area of the measuring light is widen, and the measuring light can be irradiated over the entire image pickup area of the CCD 732.

In connection with the above, a scanning direction may be an optional direction similarly to the thirty-fifth embodiment.

An endoscope apparatus for three dimensional measurement, according to a thirty-seventh embodiment of the invention, will next be described.

The endoscope apparatus for three dimensional measurement, according to the thirty-seventh embodiment, is substantially the same in arrangement as that according to the thirty-fifth embodiment, and is such that irradiation-angle wide area means is arranged without the use of a prism.

Figure 74:
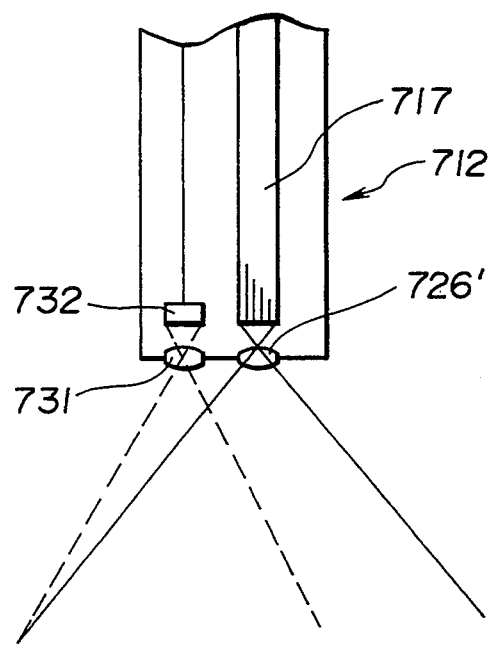
FIG. 74 is a cross-sectional view showing an arrangement of a forward end portion of an electronic scope according to a thirty-seventh embodiment of the invention.

As shown in FIG. 74, in a forward end portion 712 of an electronic scope according to the thirty-seventh embodiment, a wide-angle projecting lens 726' having an wide angle is arranged in place of the projecting lens 726, such that a measuring light can be irradiated to an entire image pickup area of a CCD 732.

Other arrangements and functions are identical with those of the thirty-fifth embodiment.

The endoscope apparatus for three dimensional measurement, according to the thirty-seventh embodiment, arranged in this manner can efficiently measure a subject 725, in a three dimensional manner, because an irradiating area of the measuring light is widen by the wide-angle projecting lens 726' so that the measuring light can be irradiated over the entire image pickup area of the CCD 732.

In connection with the above, the scanning direction may be an optional direction, similarly to the thirty-fifth embodiment.

An endoscope apparatus for three dimensional measurement, according to a thirty-eighth embodiment of the invention, will next be described.

The endoscope apparatus for three dimensional measurement, according to the thirty-eighth embodiment, is substantially the same in arrangement as that according to the thirty-fifth embodiment, and is such that irradiation-angle wide area means is arranged without the use of a prism.

Figure 75:
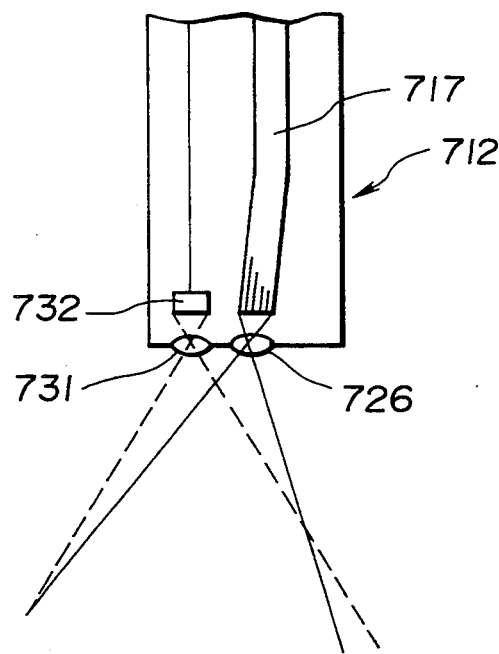
FIG. 75 is a cross-sectional view showing an arrangement of a forward end portion of an electronic scope according to a thirty-eighth embodiment of the invention.

As shown in FIG. 75, in a forward end portion 712 of an electronic scope according to the thirty-eighth embodiment, the arrangement is such that an illuminating light can be irradiated to an entire image pickup area of a CCD 732, a forward end portion of an image guide 717 is formed within the forward end portion 712 of the electronic scope such that, as shown in FIG. 68, an optical axis is maintained within a plane m so that the forward end portion of the image guide is so formed as to be directed or oriented inwardly within the forward end portion 712 of the electronic scope so as to be inclined in a direction of the optical axis of the CCD 732, and a projecting lens 726 is so arranged as to have an optical axis coincident with the optical axis of the image guide 717.

Other arrangements and functions are the same as those in the thirty-fifth embodiment.

The endoscope apparatus for three dimensional measurement, according to the thirty-eighth embodiment, arranged in this manner, can efficiently measure the subject 725 in three dimensional manner, because the forward end portion of the image guide 717 is so formed as to be directed inwardly, whereby the irradiating range of the measuring light is widen and the measuring light can be irradiated over the entire image pickup area of the CCD 732.

In connection with the above, the scanning direction may be an optional direction, similarly to the thirty-fifth embodiment.

An endoscope apparatus for three dimensional measurement, according to a thirty-ninth embodiment of the invention, will next be described.

The endoscope apparatus for three dimensional measurement, according to the thirty-ninth embodiment, is so arranged as to irradiate a plurality of measuring lights. Other arrangements are substantially the same as the endoscope apparatus for three dimensional measurement, according to the thirty-fifth embodiment and, accordingly, only a different arrangement will be described. The same or identical reference numerals are applied to the same or identical components and parts, and the description thereof will be omitted.

Figure 76:
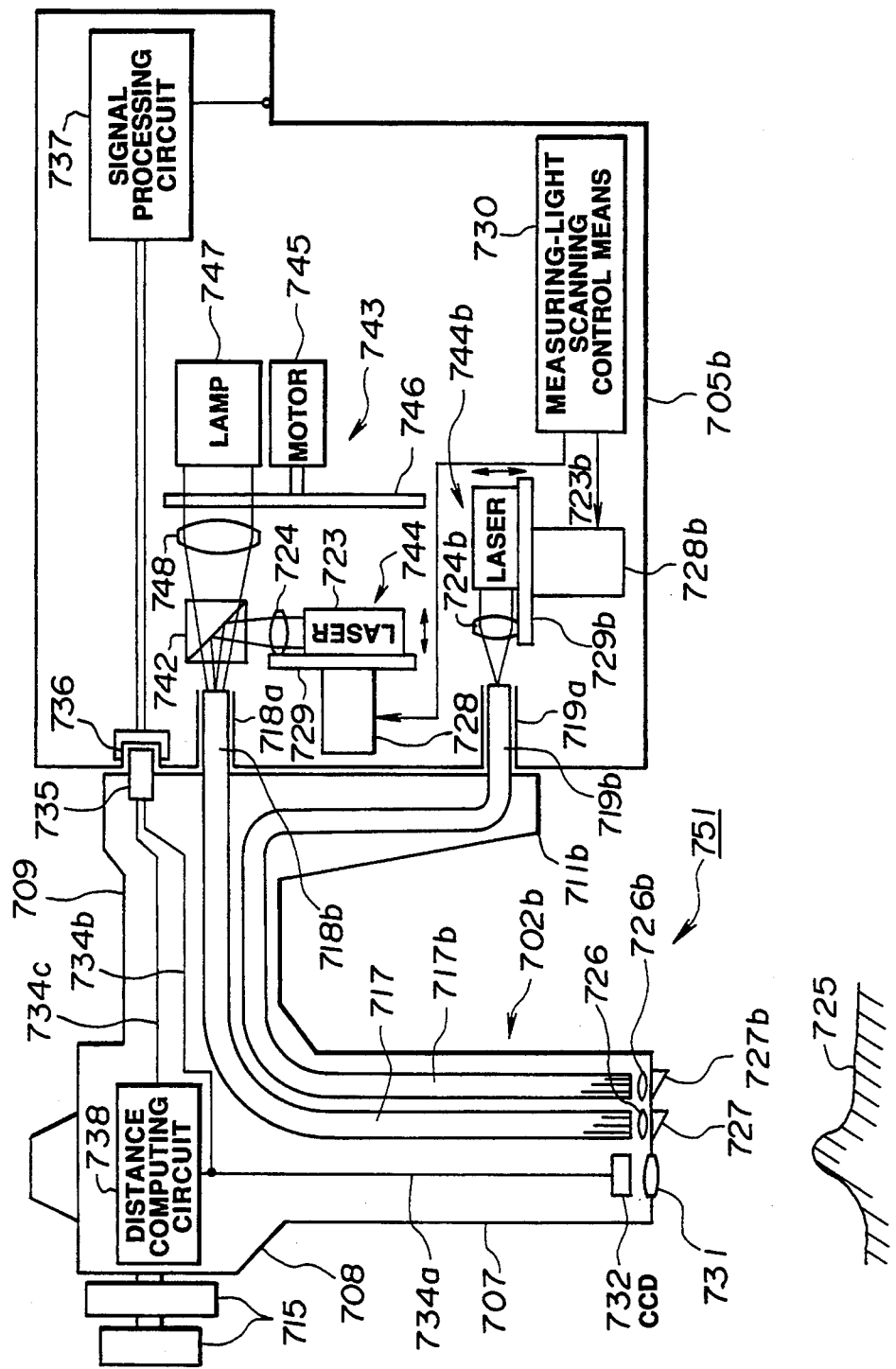

As shown in FIG. 76, an endoscope apparatus 751 for three dimensional measurement, according to the thirty-ninth embodiment, comprises an electronic scope 702b for building therein image pickup means, a light-source.processing unit 705b for building therein ordinary illuminating-light/measuring-light light source means for supplying an ordinary illuminating light to the electronic scope 702b and signal processing means for executing signal processing, and a color monitor (not shown) for displaying a standard image pickup signal which is generated in signal processing by the light-source.processing unit 705b.

The electronic scope 702b is arranged such that a second image guide 717b serving as second measuring-light transmitting means for transmitting a second measuring light is inserted in an inserting section 707 similarly to an image guide 717, the second image guide 717b is inserted also in a universal cable 709, and an image connector 719b at an end is integrally fixed by an overall connector 711b.

The light-source.processing unit 705b is provided with an image guide connector receptor 719a to which the image guide connector 719b is detachably connectable. Furthermore, measuring-light generating means 744b is arranged within the light-source.processing unit 705b, in opposed relation to the image guide connector receptor 719a.

A semiconductor laser 723b for generating a laser light and a condenser lens 724b are arranged in rear of the image guide connector receptor 719a, as the measuring-light generating means 744b. The arrangement is such that a laser light capable of being condensed due to the semiconductor laser 723b, that is, the measuring light is condensed by the condenser lens 724b, and the measuring light executing scanning in a straight-line manner is irradiated to an end surface of the fiber bundle forming the image guide connector 719b.

The second measuring light supplied to the image guide connector 719b is transmitted by the second image guide 717b, and is emanated toward a subject 725 through a projecting lens 726b and a prism 727b further from an end surface fixed to a forward end portion 712 adjacent the outgoing side, to illuminate a location adjacent to the subject 725 in a wide area manner. The prism 727b is so formed as to widen an irradiating angle of the measuring light so that the measuring light can be irradiated over an entire image pickup area of a CCD 732. Furthermore, the projecting lens 726b is mounted at a focal distance of the projecting lens 726b from the end surface of the second image guide 717b adjacent to the outgoing side. In a case of a measuring light emanated from the fiber of the end surface adjacent to the outgoing side, the optical beam can form a minute optical spot on the surface of the subject 725 without being subject to substantial spreading.

A semiconductor laser 723 and a condenser lens 724 are mounted on a table 729 which is driven in a vibratory manner by a piezo-electric element 728. A drive signal of a stepwise wave, for example, is applied to the piezo-electric element 728 from the measuring-light scanning control means 730, whereby the piezo-electric element 728 is moved in a vibratory manner in a vertical direction as indicated by an arrow, for example, in FIG. 76. By the movement in a vibratory manner in the vertical direction, the semiconductor laser 723 is also moved in a vibratory manner. The measuring light irradiated to the fiber bundle of the image guide connector 719b is successively irradiated every fiber-spaced predetermined or constant interval from each other, and is scanned in a straight-line manner toward the subject 725 through the projecting lens 726b and the prism 727b.

In this embodiment, as shown in FIG. 77, the prism 727b is arranged at a location different from a optical-axis plane of the prism 727 and the objective lens 731 which is arranged at the forward end portion 712 adjacent to the prism 727b.

Other arrangements and functions are the same as those of the thirty-fifth embodiment.

In connection with the above, the scan direction may be optional, similar to the thirty-fifth embodiment.

The endoscope apparatus 751 for three-dimensional measurement, according to the thirty-ninth embodiment, arranged in this manner, can measure irregularities which includes a shadow and which cannot be measured in a case of the measuring light due to the second image guide 717, by measurement due to the measuring light by the second image guide 717b having the optical axis different from the measuring light due to the image guide 717, in a case where, when the subject 725 is measured by the measuring light due to the image guide 717, locations occur to which the measuring light is not applied because of irregularities of the subject. Further, the endoscope apparatus 751 for three dimensional measurement can execute three dimensional measurement to the details.

Other advantages are the same as those of the thirty-fifth embodiment.

By the way, there is a case where detailed three dimensional measurement of a subject has conventionally been desired. In this case, as shown in FIG. 78, narrow-area irradiating means is provided for irradiating a measuring light from a measuring-light projecting optical system, only to a desired measurement area by a condensing lens 760 and the like, of an image pickup area of an image pickup means, whereby measurement at a measuring area L of the spot rows s of the conventional measuring pitch as shown in FIG. 79(a), is measured at the measuring area 1 of the spot rows s' of a narrower measuring pitch as shown in FIG. 79(b), whereby three dimensional measurement at the measuring area 1 can be executed with high resolution without changing the numbers of the spots. Thus, a demand such as detailed three dimensional measurement of the subject can be satisfied.

An endoscope apparatus for three dimensional measurement according to a fortieth embodiment of the invention will next be described.

Figure 81:
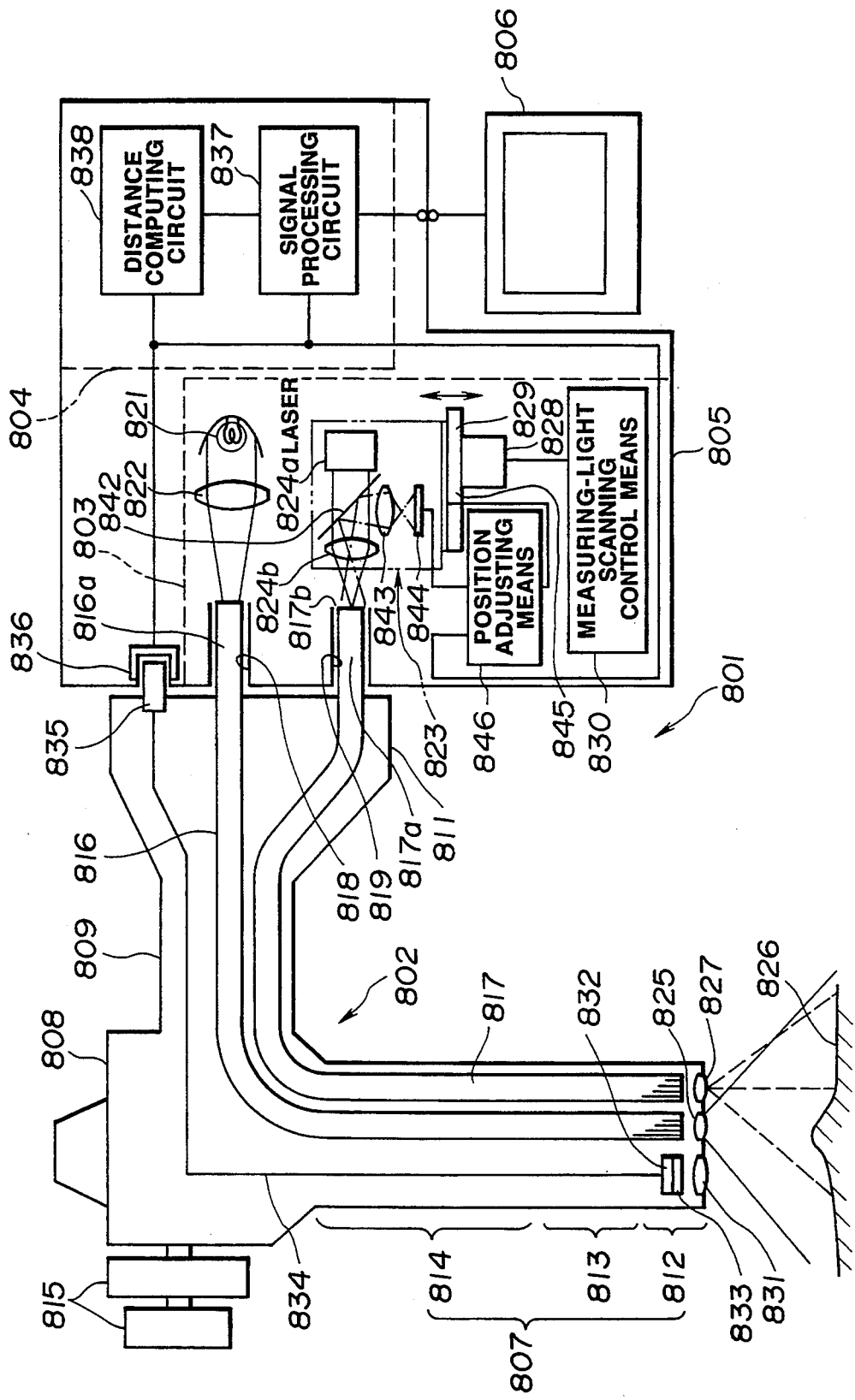

As shown in FIG. 81, an endoscope apparatus 801 for three dimensional measurement, according to the fortieth embodiment, comprises an electronic scope 802 building therein image pickup means, a light-source.-processing unit 805 building therein ordinary-illuminating-light supply means for supplying an ordinary illuminating light to the electronic scope 802, measuring-light source means 803 and signal processing means 804 for executing signal processing and distance computation, and a color monitor 806 for displaying a standard image signal generated in signal processing by the signal processing means 804.

The electronic scope 802 has an inserting section 807 which is elongated and which has flexibility so as to be capable of being inserted into a body cavity or the like, an operating section 808 which is wide in width and which is connected to a rearward end of the inserting section 807, and a universal cable 809 extending from a side of the operating section 808. The overall connector 811 mounted on an end of the universal cable 809 can detachably be connected to the light-source.processing unit 805.

The inserting section 807 has, from its forward end, a hard forward end portion 812, a curving portion 813 capable of being curved, and a flexible tube portion 814 having flexibility. A pair of curved knobs 815 mounted on a side surface of the operating section 808 are operated, whereby the curving portion 813 can be curved.

A light guide 816 for transmitting an ordinary illuminating light, and an image guide serving as measuring-light transmitting means for transmitting the measuring light are inserted in the inserting section 807. The light guide 816 and the image guide 817 are inserted also in the universal cable 809. A light guide connector 816a for holding the respective ends and an image guide connector 817a are integrally fixed by the overall connector 811.

The light-source.processing unit 805 is provided with a light guide connector receptor 818 and an image guide connector receptor 819 to which the light guide connector 816a and the image guide connector 817a can detachably be connected, respectively. A lamp 821 for generating a white light in the rear of the light guide connector receptor 818 and a condenser lens 822 are arranged within the light-source.processing unit 805. A white illuminating light from the lamp 821 can be condensed by the condenser lens 822, and can be supplied to an incident end surface of the light guide 816.

Furthermore, measuring-light supply optical means 823 is arranged in rear of the image guide connecter receptor 819. A semiconductor laser 814a for generating a laser light and a condenser lens 814b are arranged at the measuring-light supply optical means 823. A laser light having the capability of condensation due to the semiconductor laser 814a, that is, a measuring light is condensed by the condenser lens 824b, to irradiate the measuring light which scans linearly an incident end surface 817b of a fiber bundle of the image guide 817 which is retained by the image guide connector 817a.

The illuminating light supplied to the incident end surface adjacent to the light guide connector 816a is transmitted by the light guide 816, and is emanated toward a subject 826 through an illuminating lens 825 further from the end surface adjacent to the outgoing side fixed to the forward end portion 812, thereby illuminating a location adjacent to the subject 826 in a wide area manner. The illuminating lens 825 is mounted at a distance differing from the focal distance of the illuminating lens 825 from the end surface of the light guide 816 adjacent to the outgoing side.

Moreover, the measuring light irradiated to the incident end surface 817b adjacent to the image guide connector 817a is transmitted by the fibers in the image guide 817 to which the illuminating light is irradiated. The measuring light is emanated toward the subject 826 through a projecting (light projecting) lens 827 serving as a measuring-light projecting optical system, further from the end surface fixed to the forward end portion 812 adjacent to the outgoing side, thereby forming a minute optical spot on the surface of the subject 826. The projecting lens 827 is mounted at a focal distance of the projecting lens 827 from the end surface of the image guide 817 adjacent to the outgoing side. The illuminating light emanated from the fibers of the end surface adjacent to the outgoing side can form a minute optical spot on the surface of the subject 826 without being subject to substantial spreading.

Figure 80:
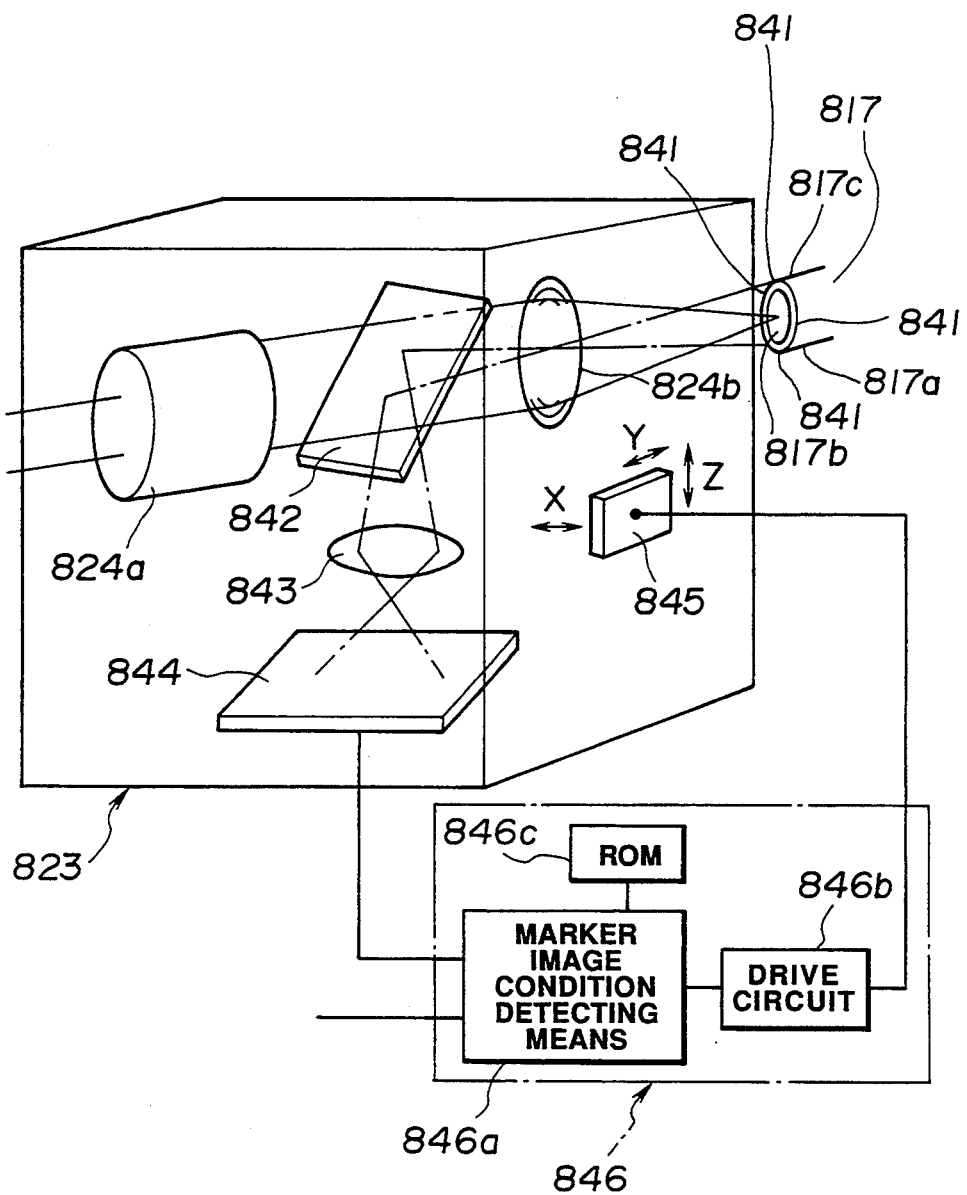
FIGS. 80 through 83 are views showing a fortieth embodiment of the invention, FIG. 80 being a schematic view of a principal portion of a measuring light-source unit for a measuring endoscope, FIG. 81 being a view showing an entire arrangement of an endoscope apparatus for three dimensional measurement, and FIGS. 82 and 83 being perspective views showing a modification.

Further, as shown in FIG. 80, four (4) position markers 841 are arranged in equally spaced relation to each other at a base end surface 817c of the image guide connector 817a. Furthermore, referring back to FIG. 81, a half mirror 842 for reflecting the lights from the position markers 841 to a predetermined direction is interposed between the semiconductor laser 824a of the measuring-light supply optical means 823 and the condenser lens 824b. An image pickup element 844 is arranged in opposed relation in a reflecting direction of the half mirror 842 through an image pickup lens 843.

A drive unit 845 for moving the measuring-light supply optical means 823 in three dimensional directions (X, Y, Z directions in FIG. 80) is arranged in connecting form to the measuring-light supply optical means 823. The drive unit 845 is mounted on a table 829 which is driven in a vibratory manner by a piezo-electric element 828. A driving signal from measuring-light scanning control means 830 is applied to the piezo-electric element 828, whereby the piezo-electric element 828 is moved in a vibratory manner vertically as indicated by an arrow, for example, in FIG. 81. By the vertical vibratory movement, the semiconductor laser 824a is also similarly moved in a vibratory manner. The measuring light is scanned linearly through the projecting lens 827 toward the subject 826.

The piezo-electric element 828 is driven by a drive signal in the form of, for example, a stepwise wave from the measuring-light scanning control means 830. By this driving, the measuring light irradiated to the incident end surface 817b of the image guide 817 is successively irradiated every fiber-spaced constant or predetermined interval away from each other, and scans, in a stepwise and linear manner, the substantially the cross-sectional area of the fiber bundle.

On the other hand, the subject 826 illuminated by the illuminating light in a wide area manner is imaged onto an image pickup surface of a CCD 832 serving as an image pickup element arranged as a focal surface of an objecting lens 831, by the objective lens 831 which is mounted on an observation window in the forward end portion 812.

A mosaic color filter 833, for example, is mounted in front of the image pickup surface, to execute optical color separation. The CCD 832 is connected to a signal connector 835 of an overall connector 811 through a signal cable 834, and is connected to a signal processing circuit 837, a distance computing circuit 838, and marker image pickup condition detecting means 846a of the position regulating means 846 as shown in FIG. 80 through a signal connector receptor 836 to which the signal connector 835 is connected.

Further, the image pickup element 844 provided on the measuring-light supply optical means 823 is connected to the marker image pickup condition detecting means 846a. Furthermore, the marker image pickup condition detecting means 846a is connected to the drive unit 845 through a drive circuit 846b.

In the present embodiment, the objective lens 831 and the projecting lens 827 are provided on the forward end portion 812 in adjacent relation to each other. The illuminating lens 825 is provided on one or each of both the objective lens 831 and the projecting lens 827.

Moreover, in the present embodiment, as shown in FIG. 81, in a case where the table 829 is vibrated vertically, the laser light scans the fiber bundle vertically on the side adjacent to the incident end surface 817b of the image guide 817. This scanning corresponds to a condition in which scanning is made horizontally in FIG. 81, on the side adjacent to the outgoing end surface 817b. The measuring light projected toward the subject 826 through the projecting lens 827 is emanated radially by the projecting lens 827, within the plane including the optical axis of the objective lens 831 and the optical axis of the projecting lens 827.

As described above, since the table 829 is scanned stepwise, in a case where the surface of the subject 826 is planar, for example, and the measuring light is scanned under a condition that the end surface of the forward end portion 812 is confronted vertically against the planar surface, spot rows spaced apart from each other substantially at constant intervals appear on the image pickup surface of the CCD 832 correspondingly to the stepwise scanning. The intervals between the spot rows vary depending upon the distance between the forward end surface of the scope 802 and the subject 826. Thus, it is possible to compute the actual spot distance on the basis of the triangulation.

On the other hand, in a case where the surface of the subject 286 is irregular, spot rows having no constant intervals appear linearly in accordance with the irregular surface. Also in this case, it is possible to compute a distance to the spot position actually formed on the surface of the subject 826, by the use of the principle of triangulation, on the basis of the positional information of each spot on the CCD 832. The distance computing circuit 838 executes computation of this distance.

In connection with the above, there is a case where the spots on the surface of the subject 826 are piled upon each other at a portion where the amount of irregularity is large. For this reason, the size or magnitude of the pitch of the stepwise wave can be variably set in accordance with the using state.

The distance computing circuit 838 separates in color the output signal from the CCD 832, and extracts, for example, signal components of the wavelength of the laser light. The distance computing circuit 838 subtracts an envelope detecting signal or a low-pass signal of the signal component from the latter, to detect the spot. In this manner, the distance computing circuit 838 finds the spot position on the surface of the CCD 832.

Furthermore, the distance computing circuit 838 further computes, subsequent to the computing of the distance, a distance-direction component connecting the subject 826 and the forward end surface of the scope 802 to each other, that is, an amount of irregularity in the height direction of the surface of the subject 826. An irregularity data signal is outputted to the signal processing circuit 837. The signal processing circuit 837 superimposes the irregularity data signal on the image signal representing the endoscope image, to output the superimposed signal to the monitor 806.

Operation of the embodiment arranged as described above will next be described below.

When the overall connector 811 provided at the end of the universal cable 809 is connected to the light-source.processing unit 805, the light guide connector 816a, the image guide connector 817a and the signal connector 835 fixed to the overall connector 811 are connected, respectively, to the connector receptors 818, 819 and 836 provided on the light-source.processing unit 5.

Then, the lights from the position markers 841 provided at the base end surface 817c of the image guide connector 817a are reflected by the half mirror 842 through the condenser lens 824b, and enters the image pickup lens 843 and, subsequently, is imaged onto the image pickup surface of the image pickup element 844.

In connection with the above, the lights from the position markers 841 may be any one of a natural light and a reflecting light. At the marker image pickup condition detecting means 846a of the position regulating means 846, the imaging position, on the image pickup surface, of the lights from the position markers 841 and reference position data beforehand stored in a ROM 846c are compared with each other on the basis of the output signal from the image pickup element 844. The reference position corresponds to the imaged positions of the lights from the position markers 841 when the incident end surface of the image guide 817 is properly or correctly connected to the measuring-light supply optical means 843, and is set every the numbers (four locations) of the position markers 841.

By backlash or rattle between the image guide connector 817a and the connector receptor 819, in a case where the relative position between the incident end surface 817b of the image guide 817 and the measuring-light supply means 823 are fixed while being shifted at assembling, a drive signal corresponding to a difference due to comparison with the reference-position data is outputted to the drive unit 845 through the drive circuit 846b because the imaging position of the image pickup element 844 on the image pickup surface is shifted (in either direction in the secondary plane). By this drive unit 845, the measuring-light supply optical means 823 is moved so that the relative position between the incident end surface 817b of the image guide 817 and the measuring-light supply optical means 823 is corrected, and controlling is executed such that the measuring light always scans the same location.

Furthermore, the measuring light is extracted from the endoscope image sent from the CCD 832 at the marker image pickup condition detecting means 846a. The drive signal is outputted to the drive unit 845 so that the area of the measuring light is minimized. In this manner, a light collecting condition of the measuring light emanated from the semiconductor laser 814a with respect to the incident end surface 817b of the image guide 817 is controlled.

As a result, correction is three-dimensionally executed such that the relative position between the incident end surface 817b of the image guide 817 and the measuring-light supply optical means 823 is made always constant. Thus, measuring accuracy is improved, and high measurement resolution is obtained.

Figure 82:
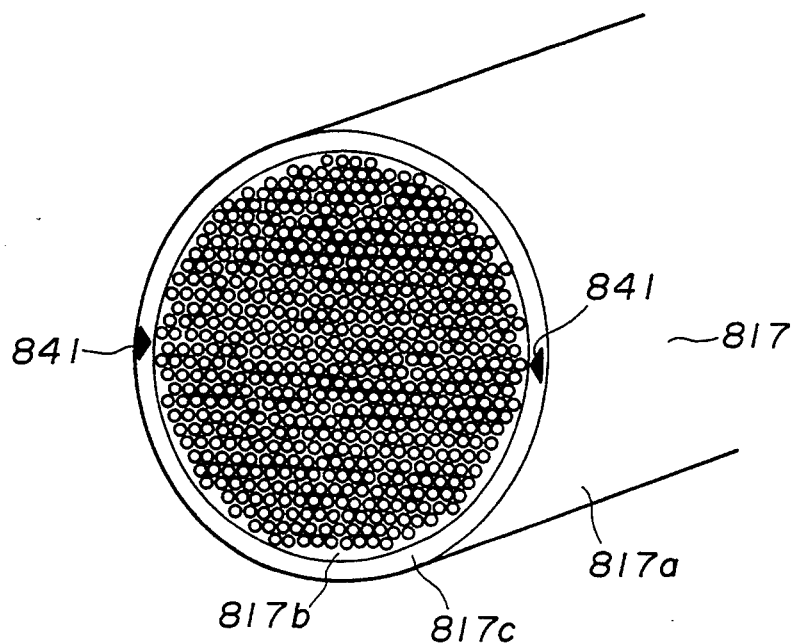

In connection with the above, as shown in FIG. 82, the position markers 841 may be two (2) which are provided on a diagonal line of the base end surface 817c, or may be more than five (5) which are provided on a diagonal line of the base end surface 817c.

Figure 83:
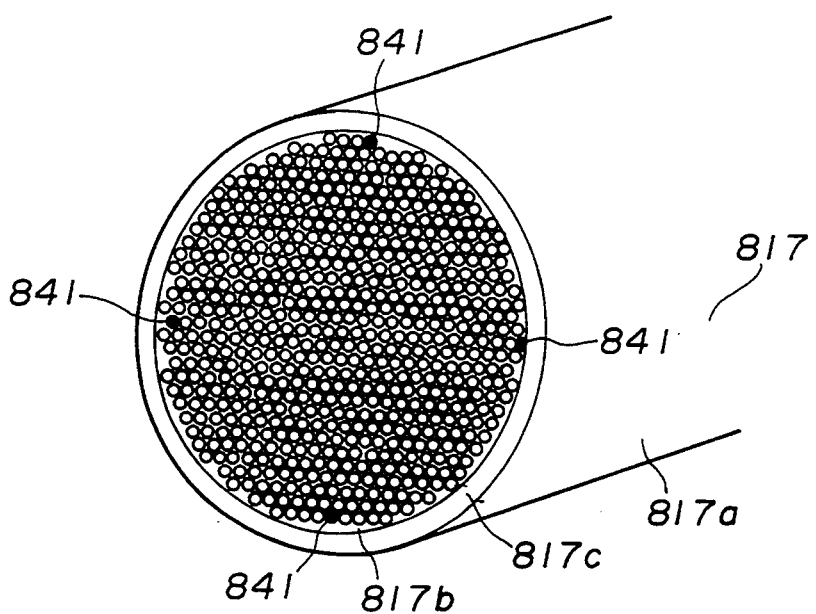

Moreover, as shown in FIG. 83, the position markers 841 may be ones which are arranged such that metal is vacuum-deposited on a specific fiber end surface.

Further, the position markers should not be limited to optical detection, but may be ones which execute magnetic detection. Furthermore, the arrangement may be such that a position of the image guide adjacent to the incident end surface thereof is moved, and the relative position between the incident end surface and the measuring-light supply optical means 823 is adjusted.

An endoscope apparatus for three dimensional measurement according to a forty-first embodiment of the invention will next be described.

The arrangement of the endoscope apparatus for three dimensional measurement may be any one of the arrangements of the respective embodiments described above. The forty-first embodiment is an embodiment in which a measuring-light spot is scanned a predetermined distance or a predetermined range of the end surface of an image guide within a single field.

First, a case will be described where a relative position between an image guide for transmission of a measuring light and a laser optical spot is moved continuously only through a distance the same as a diameter of an end surface of the image guide, within a single field. FIG. 84 is a view for explanation, illustrating this case.

When the relative position is moved only through the same distance as a diameter of an image guide end surface 917a as illustrated in FIG. 85 within a single field, the measuring light is transmitted only when the laser optical spot is located at a position where the laser optical spot can be incident upon the fibers in the image guide.

As a result, the spot rows are projected onto the subject. When, however, there are many fibers of the image guide for transmission of the measuring light, these spot rows are regarded approximately as a straight line. Accordingly, these spot rows are image-picked-up as if a slit light is projected onto the subject. This pseudo-slit light is arranged such that, since the imaging on the image pickup element is shifted due to the irregularity on tile subject, an irregularity on a portion which is scanned by the laser spot can be measured by a method similar to a so-called optical cutting method. Specifically, in this example, since it is possible to measure the irregularity on many points on the subject through one (1) field, three dimensional measurement can be executed efficiently more than a case where one or a plurality of spot lights is or are projected onto the subject through one (1) field.

Figures 86A, 86B:
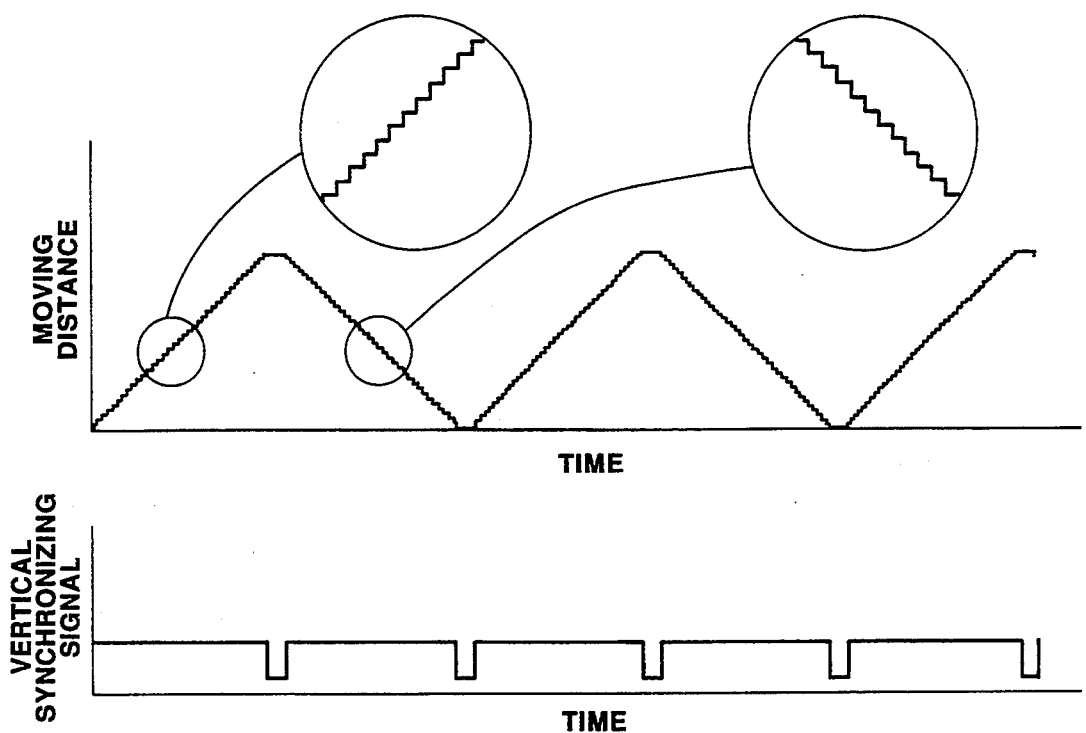

A case will next be described where the relative position between the image guide for transmission of the measuring light and the laser optical spot is moved stepwise through a distance the same as the diameter of the image guide end surface within one (1) field. Other is the same as the example illustrated in FIG. 84. FIG. 86 is a view for explanation, illustrating this case.

One (1) step is the same as a fiber pitch of the image guide for transmission of the measuring light. Accordingly, the measuring light is incident 100% upon the image guide for transmission of the measuring light, and it is possible to improve the transmission efficiency of the measuring light, more than the example illustrated in FIG. 84.

In connection with the above, in the example shown in FIGS. 84 and 86, a case has been described where the relative position between the image guide for transmission of the measuring light and the laser optical spot is moved through a distance the same as the diameter of the image guide end surface within one (1) field. However, the invention should not be limited to this specific situation. The relative position may be moved within one (1) frame, or may be repeated several times within one (1) field. Moreover, the amount of movement of the relative distance may be reduced less than the diameter of the image guide.

Further, as shown in FIG. 87, the arrangement may be such that a plurality of, for example, three laser-light generating means 901,902 and 903, and a plurality of lenses 904, 905 and 906 and a plurality of prisms 907 and 908 are used to execute driving by a piezo-electric actuator 908, for example, whereby a plurality of spot lights scan the end surface of the image guide 917 for transmission of the measuring light. Furthermore, the arrangement may be such that a single laser spot light is scanned at a high speed, whereby a plurality of pseudo-silt lights are projected to a subject through an imaging lens 909. In this connection, there are three laser-light generating means. However, the invention should not be limited to this specific arrangement. The Invention may be formed such that a plurality of laser-light generating means are provided.

Figure 88:
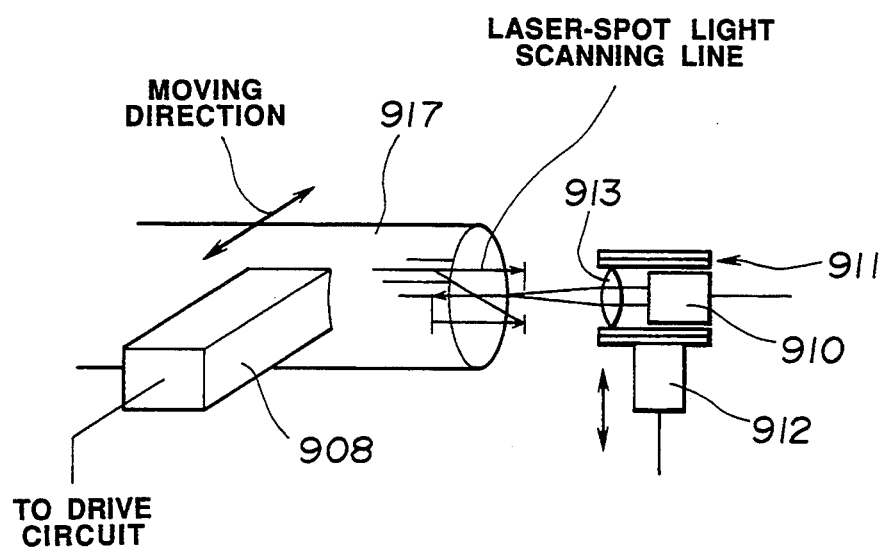

Moreover, the arrangement may be such that the scanning line of the scanning laser spot light at the end surface of the image guide for transmission of the measuring light is shifted vertically with respect to the scanning direction every scanning, whereby the irregularity on the entire subject can be measured. In order to shift the scanning-line position vertically with respect to the scanning direction, as shown in FIG. 88, the arrangement may be such that the laser generating means 911 is driven by the piezo-electric actuator 908, whereby the laser generating means 911 having mounted thereon the laser generating means 910 is moved vertically with respect to the scanning direction by the piezo-electric actuator 912, with respect to the end surface of the image guide 917 for transmission of the measuring light, which is moved in a scanning direction.

In connection with the above, in each of the above-described embodiments, the electronic scope is arranged such that the illuminating light and the measuring light are irradiated in separation by the half prism by the use of a single image guide. The embodiments should not be limited to this specific arrangement. The electronic scope may be one which is provided with a separate light guide which is inserted in the inserting section or the like, as illuminating-light transmitting means.

Further, in each of the above-described embodiments, in order to produce the color image, the illuminating-light generating means uses the surface successive system in which the white illuminating light of the lamp is irradiated to the RGB rotary plate which is rotatively driven by the motor, and the RGB light generated through the RGB rotary disc is irradiated. However, the embodiments should not be limited to this specific arrangement. The arrangement may be a color separation system in which the white illuminating light of the lamp is irradiated, and a mosaic color filter, for example, is mounted in front of the CCD image pickup surface, to execute color separation optically.

Conversely, in each of the above-described embodiments, in order to produce the color image, the illuminating-light generating means uses a color separation system in which the white illuminating light of the lamp is irradiated, and the mosaic color filter is mounted in front of the CCD image pickup surface, to execute color separation optically. However, the invention should not be limited to these specific embodiments. For example, each of the embodiments may be a surface successive system in which the white illuminating light of the lamp is irradiated to the RGB rotary disc rotatively driven by the motor, and the RGB light generated through the. RGB rotary disc is irradiated.

Furthermore, in each of the above-described embodiments, the illuminating-light generating means is arranged such that the RGB rotary disc rotatively driven by the motor is arranged between the lamp and the condenser lens. However, the invention should not be limited to these specific embodiments. The invention may be arranged such that the RGB rotary disc is arranged between the condenser lens and the incident end surface of the image guide connector, for example.

Moreover, in each of the above-described embodiments, a lens of refractive-index distribution type, or a relay lens system may be used in place of the image guide which is used to transmit at least the measuring light, or a light guide may be used which is provided with means for executing correlation with respect to an arrangement in which the arrangement of the fibers at one end surface and the other end surface has no regulation like the light guide.

Further, each of the above-described embodiments is arranged such that the measuring light is scanned on the side adjacent to the light source unit, i.e., for example, scanning is made mechanically by the piezo-electric element, to change the incident position to one end surface of the image transmitting means. However, the arrangement may be such that an optical element such as KDP or the like is used to control an optical characteristic with respect to the electric signal of the element, in place of the piezo-electric element, to have a similar function, and to have an equivalent function. Furthermore, the arrangement may be such that scanning is not executed mechanically or the like, but a plurality of LEDs are arranged in a line manner or the like at predetermined or constant intervals or the like in opposed relation to one end surface of the image transmitting means, and are simultaneously turned on (or are selectively driven).

Moreover, the case has been described where the measuring-light spot is formed along a straight line. However, the invention should not be limited to this specific arrangement. The measuring-spot may be formed so as to have two-dimensional extension or spreading such as, for example, in a square lattice or the like. Further, the arrangement may be such that, in a case where the measuring-light spot is formed in a two-dimensional manner, the distance between the measuring-light spots is computed and the irregular configuration of the surface of the subject is displayed in a three-dimensional manner. In this case, the arrangement may be such that, as occasion demands, interpolation is executed to find an irregular configuration other than the measuring point.

In connection with the above, the invention should not be limited to a case of the electronic scope. It will be apparent, however, that the invention can similarly be applied to an arrangement in which a TV camera building therein image pickup means such as a CCD or the like is mounted on an optical endoscope such as a fiber scope or the like. Furthermore, each of the above-described embodiments is an embodiment in which image pickup means for normal or ordinary observation and image pickup means for detection of a measuring light are used as both image pickup means. However, the image pickup means for ordinary observation and the image pickup means for detection of a measuring light may be provided or arranged separately. Moreover, the image pickup means provided in use both as the image pickup means for ordinary observation and the image pickup means for detection of a measuring light may be used in time sharing. Further, the arrangement may be such that two image pickup means are provided, and one or both of the image pickup means, for example, is or are used to detection of a distance or the like, or is or are also used as stereophonic observation. Also in this case, the arrangement may be used in time sharing.

In connection with the above, phases may be changed every scanning, as a method of forming the measuring light. Furthermore, scanning of the measuring light may be one which uses a flying spot tube, an LCD, a plasma or the like. Moreover, the arrangement may be such that a line light is projected, and is scanned to obtain a two-dimensional image. Further, the arrangement may be such that a lattice pattern is projected and is scanned. Furthermore, the arrangement may be such that computation such as a plurality of distances or the like is executed by one (1) frame. Moreover, a shade may be projected. Further, if fibers on the scanning line are broken, adjacent fibers may be used or the like.

Furthermore, the arrangement may be such that in a case where the measuring spot is formed in a two dimensional manner, a distance between the measuring spots is computed, and an irregular configuration on the surface of the subject is displayed in three dimensional manner. In this case, as occasion demands, interpolation may be executed to find an irregular configuration other than the measuring point.

Moreover, each of the above-described embodiments is arranged such that, in order for that the measuring-light spot is scanned on the surface of the subject, the laser light or the like irradiated toward the incident end surface of the image transmitting means is scanned. However, the invention should not be limited to this specific arrangement. The arrangement may be such that a portion of the end surface of the image guide, for example, adjacent to the outgoing side is vibrated in a direction extending perpendicularly to the optical axis of the projecting lens, or the projecting lens is vibrated in a direction extending perpendicularly to the optical axis of the projecting lens, so that the measuring-light spot projected toward the subject through the projecting lens is scanned.

On the other hand, a method in which the spot light is scanned should not be limited to one disclosed in each of the above-described embodiments. The laser light may be scanned by a galvanomirror or a polygon mirror, or a flying spot scanner may be utilized to scan the spot light.

Further, the invention should not be limited to a use for a medical, but may be applied to measurement of flaws and deformation of a water pipe, a gas pipe, an engine for an aircraft and the like, and advantages of the invention are great.

Furthermore, the arrangement may be such that the measuring light is not projected only on a single glass fiber forming the image guide, but the measuring light is projected onto a plurality of adjacent glass fibers. In this case, a spatial resolution of measurement is reduced, but an amount of light of the measuring light increases, and this is effective in a case of a dark subject. Moreover, if the forward end of the endoscope and the subject are close to each other, reduction of the resolution can be resolved to a certain degree.

Further, the wavelength of the measuring light may be within a visible optical area or region, and may be out of the visible optical area. Furthermore, the above-described embodiments may partially combined with each other to form different embodiments.

It will be apparent that, in this invention, various different embodiments within a broad scope can be formed on the basis of the present invention, without departure from the spirit of the invention and the scope thereof. The present invention is limited by appended claims, but should not be limited by other specific embodiments.

What is claimed is:

1. An endoscope apparatus for three dimensional measurement, comprising:
   an endoscope having an inserting section inserted into a body cavity;
   a light-source unit having measuring spot-light supply means for supplying at least one measuring spot light for three dimensional measurement, and illuminating-light supply means for supplying an illuminating light irradiated over a wide area;
   optical transmitting means having an incident end and an outgoing end, said optical transmitting means being inserted in said inserting section for transmitting said measuring light and said illuminating light from said light-source unit to said outgoing end to irradiate said measuring light and said illuminating light to a subject;
   scanning means provided adjacent to said incident end of said optical transmitting means, for producing a scanning pattern of a scanning spot light within a plane extending perpendicularly to an optical axis of said measuring spot light without moving said outgoing end of said optical transmitting means according to the scanning pattern;
   image pickup means for image-picking-up return lights of said measuring spot light and said illuminating light, irradiated to said subject returned from said subject; and
   distance computing means for image-picking-up the return light of said measuring spot light by said image pickup means to compute a distance to said subject.

2. An endoscope apparatus for three dimensional measurement, according to claim 1, wherein said scanning means scans said measuring spot light for a predetermined range within the plane extending perpendicularly to the optical axis of said measuring spot light, within an image pickup period of time of a single field of said image pickup means.

3. An endoscope apparatus for three dimensional measurement, according to claim 1, comprising wide-area irradiating means for irradiating said measuring light to an entire image pickup area of at least said image pickup means.

4. An endoscope apparatus for three dimensional measurement, according to claim 3, wherein said wide-area illuminating means is a prism for bringing an outgoing angle to a wide angle, provided at the outgoing end surface of said optical transmitting means.

5. An endoscope apparatus for three dimensional measurement, according to claim 1, wherein said optical transmitting means includes a measuring spot light transmitting element for transmitting said measuring spot light and an illuminating-light transmitting element for transmitting said illuminating light.

6. An endoscope apparatus for three dimensional measurement, according to claim 5, wherein said measuring spot light transmitting element is an image guide for transmitting an image formed by a plurality of optical fibers.

7. An endoscope apparatus for three dimensional measurement, according to claim 1, wherein said optical transmitting means has a single optical transmitting element for transmitting said measuring spot light and said illuminating light.

8. An endoscope apparatus for three dimensional measurement, according to claim 7, wherein said optical transmitting element is an image guide for transmitting an image formed by a plurality of optical fibers.

9. An endoscope apparatus for three dimensional measurement according to claim 1, wherein said image pickup means comprises at least two solid state imaging devices located a predetermined distance from one another in a distal end of said inserting section.

10. An endoscope apparatus for three dimensional measurement according to claim 9, wherein each said solid state imaging device comprises a charge-coupled device.

11. An endoscope apparatus for three dimensional measurement according to claim 1, wherein said scanning means provides a reciprocating movement to said incident end of said optical transmitting means to produce the scanning of said scanning spot light.

12. An endoscope apparatus for three dimensional measurement according to claim 11, wherein the reciprocating movement is in said plane extending perpendicularly to the optical axis of said measuring spot light.

13. An endoscope apparatus for three dimensional measurement, according to claim 1, wherein said scanning means is provided with scanning-range control means for varying a scanning range of said measuring spot light.

14. An endoscope apparatus for three dimensional measurement, according to claim 13, wherein said scanning-range control means changes a scanning range of said measuring spot light on the basis of the image pickup signal from said image pickup means.

15. An endoscope apparatus for three dimensional measurement, according to claim 13, including:
display means for generating an image signal on the basis of the image pickup signal from said image pickup means obtained by said illuminating light, to display an image of the subject; and
indicating means for indicating a scanning range of said measuring spot light, on the basis of the image of said subject displayed on said display means,
wherein said scanning-range control means changes a scanning range of said measuring spot light, on the basis of an indicating signal from said indicating means.

16. An endoscope apparatus for three dimensional measurement, according to claim 1, comprising:
a plurality of position markers provided on the incident end surface of said optical transmitting means or at a position adjacent to said incident end surface;
position-marker detecting means for detecting said position markers; and
position regulating means for regulating a relative position between the incident end surface of said optical transmitting means and said measuring-light supply means such that said position markers detected by said position marker detecting means are within a reference position set beforehand.

17. An endoscope apparatus for three dimensional measurement, according to claim 16, wherein said position marker detecting means image-pickups the light from said position markers to detect the position markers.

18. An endoscope apparatus for three dimensional measurement, according to claim 17,
wherein said position markers are reflecting elements reflecting said measuring spot light or said illuminating light, and
wherein said position marker detecting means detects the lights from said reflecting elements.

19. An endoscope apparatus for three dimensional measurement, according to claim 17,
wherein said position markers are light emitting elements; and
wherein said position marker detecting means detects a light from said light emitting elements.

20. An endoscope apparatus for three dimensional measurement, according to claim 1, wherein said optical transmitting means is connected to said light source unit by one connector provided adjacent to said incident end.

21. An endoscope apparatus for three dimensional measurement, according to claim 20, wherein said optical transmitting means has a measuring spot light transmitting element for transmitting said measuring spot light, and an illuminating-light transmitting element for transmitting said illuminating light.

22. An endoscope apparatus for three dimensional measurement, according to claim 20, wherein said optical transmitting means has a single optical transmitting element for transmitting said measuring spot light and said illuminating light.

23. An endoscope apparatus for three dimensional measurement, according to claim 21 or 22, including focal-position control means for variably controlling a focal position of said measuring spot light emanating from said optical transmitting means.

24. An endoscope apparatus for three dimensional measurement, according to claim 22, including supplied-light separating means for separating said measuring light and said illuminating light supplied to said optical transmitting element.

25. An endoscope apparatus for three dimensional measurement, according to claim 1, comprising irradiating-strength control means for controlling an irradiating strength of at least said measuring spot light, on the basis of an image pickup signal produced by said image pickup means.

26. An endoscope apparatus for three dimensional measurement, according to claim 25, including illuminating-strength control means for controlling an illuminating strength of said illuminating light, by the image pickup signal produced by said image pickup means.

27. An endoscope apparatus for three dimensional measurement, according to claim 26, wherein said illuminating-strength control means controls the illuminating strength of said measuring spot light, on the basis of the image pickup signal of said illuminating light produced by said image pickup means.

28. An endoscope apparatus for three dimensional measurement, according to claim 26, wherein said illuminating-strength control means controls the illuminating strength of said measuring spot light, on the basis of the image pickup signal of said measuring spot light produced by said image pickup means.

29. An endoscope apparatus for three dimensional measurement, according to claim 26, wherein said illuminating-strength control means is provided with peak hold means for holding a peak of the image pickup signal obtained by said image pickup means, and measuring-light supply control means for controlling said measuring-light supply means, on the basis of an output from said peak hold means.

30. An endoscope apparatus for three dimensional measurement, according to claim 26, wherein said measuring-light supply control means is provided with comparator means for comparing the output from said peak hold means with a predetermined value, and control-signal generating means for generating a control signal for controlling said measuring-light supply means, on the basis of an output from said comparator means.

31. An endoscope apparatus for three dimensional measurement, according to claim 1, comprising separating means for separating an image pickup signal due to said measuring spot light, from an image pickup signal obtained by said image pickup means.

32. An endoscope apparatus for three dimensional measurement, according to claim 31,
wherein said measuring-light supply means is provided with characteristic changing means for supplying a plurality of measuring spot lights and for changing respective characteristics of said plurality of measuring spot lights emanated from the outgoing end surface of said optical transmitting means, and
wherein said separating means separates image pickup signals due to said plurality of measuring spot lights, from the image pickup signal from said image pickup means, in accordance with the characteristics of said plurality of measuring spot lights due to said characteristic changing means.

33. An endoscope apparatus for three dimensional measurement, according to claim 31,
wherein said illuminating-light supply means supplies intermittently the illuminating light to said optical transmitting means,
wherein said measuring spot light supply means supplies said measuring spot light to said optical transmitting means during a period of time said illuminating light is not supplied, and
wherein said separating means separates the image pickup signal due to said measuring spot light, from the image pickup signal produced by said image pickup means, on the basis of timing at which said measuring light spot is irradiated.

34. An endoscope apparatus for three dimensional measurement, according to claim 31,
wherein said illuminating-light supply means supplies the illuminating light continuously to said optical transmitting means,
wherein said measuring spot light supply means supplies the measuring light intermittently to said optical transmitting means, and
wherein said separating means subtracts an image pickup signal except for the illuminating period of time of the measuring spot light, from the image pickup signal during the illuminating period of time of said measuring light spot, thereby separating said image pickup signal due to said measuring spot light, from the image pickup signal produced by said image pickup means.

35. An endoscope apparatus for three dimensional measurement, according to claim 31,
wherein said measuring spot light supply means supplies a plurality of measuring spot lights,
wherein said endoscope apparatus comprises characteristic changing means for changing characteristics of said plurality of measuring spot lights supplied from said measuring spot light supply means, and
wherein said separating means separates said plurality of measuring spot lights from the image pickup signal produced by said image pickup means, in accordance with the characteristics of said plurality of measuring spot lights due to said characteristic changing means.

36. An endoscope apparatus for three dimensional measurement, according to claim 31,
wherein said illuminating-light supply means supplies a plurality of illuminating lights different in wavelength from each other, intermittently to said optical transmitting means,
wherein said measuring spot light supply means supplies said measuring spot light to said optical transmitting means, during the fact that the plurality of illuminating lights different in wavelength from each other are not supplied, and
wherein said separating means separates the image pickup signal due to said measuring spot light, from the image pickup signal produced by said image pickup means, on the basis of timing at which said measuring spot light is irradiated.

37. An endoscope apparatus for three dimensional measurement, according to claim 36, wherein the plurality of illuminating lights different in wavelength from each other, supplied by said illuminating separating means are R, G and B illuminating lights.

38. An endoscope apparatus for three dimensional measurement, according to claim 31,
wherein said illuminating-light supply means supplies a plurality of illuminating lights different in wavelength from each other, to said optical transmitting means,
wherein said measuring spot light supply means supplies said measuring spot light having a predetermined light quantity, to said optical transmitting means, every illuminating period of time corresponding to each of the plurality of illuminating lights different in wavelength from each other, and
wherein said separating means separates image pickup signals due to said plurality of measuring spot lights different in wavelength from each other, and the image pickup signal due to said measuring spot lights having the predetermined light quantity from the image pickup signal produced by said image pickup means.

39. An endoscope apparatus for three dimensional measurement, according to claim 38, wherein said plurality of illuminating lights different in wavelength from each other, supplied by said illuminating separating means, are R, G and B illuminating lights, wherein said measuring spot light supply means supplies said measuring spot light to said optical transmitting means, except for an illuminating period of time corresponding to not more than two of said R, G and B illuminating lights, and wherein said separating means subtracts an image pickup signal having a color to which said measuring spot light is not supplied to said optical transmitting means, of said R, G and B illuminating lights, from the image pickup signal having a color in which the measuring spot light is supplied to said optical transmitting means, of said R, G and B illuminating lights, thereby separating said image pickup signal due to said measuring spot light, from the image pickup signal produced by said image pickup means.

40. An endoscope apparatus for three dimensional measurement, comprising:

an endoscope having an inserting section inserted into a body cavity;

a light source unit having measuring-light supply means for supplying a measuring light for three dimensional measurement, and illuminating-light supply means for supplying an illuminating light irradiated in a wide area manner;

optical transmitting means having an incident end and an outgoing end, said optical transmitting means being inserted in said inserting section for transmitting said measuring light and said illuminating light from said light source unit to said outgoing end to irradiate said measuring light and said illuminating light to a subject;

scanning means provided adjacent to said incident end of said optical transmitting means to cause scanning movement in a predetermined pattern of a spot light of said measuring light within a plane extending perpendicularly to an optical axis of said measuring spot light without moving said outgoing end of said optical transmitting means according to the predetermined pattern;

image pickup means for image-picking-up return lights of said measuring light and said illuminating light irradiated to said subject, from said subject; and distance computing means for image-picking-up the return light of said measuring light by said image pickup means to compute a distance to said subject.

41. An endoscope apparatus for three dimensional measurement, according to claim 40, including irradiation-strength control means for controlling an illuminating strength of said illuminating light, on the basis of the image pickup signal produced by said image pickup means.

42. An endoscope apparatus for three dimensional measurement, according to claim 41, wherein said irradiation-strength control means controls an irradiation strength of said measuring spot light, by an image pickup signal of said measuring illuminating light obtained by said image pickup means.

43. An endoscope apparatus for three dimensional measurement, according to claim 41, wherein said irradiation-strength control means controls the irradiation strength of said measuring spot light, by an image pickup signal of said measuring spot light obtained by said image pickup means.

44. An endoscope apparatus for three dimensional measurement, according to claim 41, wherein said irradiation-strength control means is provided with peak hold means for holding a peak of the image pickup signal obtained by said image pickup means, and measuring-light supply control means for controlling said measuring-light supply means, on the basis of an output from said peak hold means.

45. An endoscope apparatus for three dimensional measurement, according to claim 44, wherein said measuring-light supply control means is provided with comparator means for comparing the output from said peak hold means with a predetermined value, and control-signal generating means for generating a control signal for controlling said measuring-light supply means, on the basis of an output from said comparator means.

* * * * *